US012559485B2

(12) United States Patent
Yang et al.

(10) Patent No.: US 12,559,485 B2
(45) Date of Patent: Feb. 24, 2026

(54) CDK6/DYRK2 DUAL-TARGET INHIBITOR, AND PREPARATION METHOD THEREFOR AND USE THEREOF

(71) Applicant: JIANGSU TASLY DIYI PHARMACEUTICAL CO., LTD., Huai'an (CN)

(72) Inventors: Peng Yang, Nanjing (CN); Haiping Hao, Nanjing (CN); Yibei Xiao, Nanjing (CN); Kai Yuan, Nanjing (CN); Xiao Wang, Nanjing (CN); Wenbin Kuang, Nanjing (CN)

(73) Assignee: JIANGSU TASLY DIYI PHARMACEUTICAL CO. , LTD., Huai'an (CN)

( * ) Notice: Subject to any disclaimer, the term of this patent is extended or adjusted under 35 U.S.C. 154(b) by 516 days.

(21) Appl. No.: 18/014,242

(22) PCT Filed: Mar. 19, 2021

(86) PCT No.: PCT/CN2021/081717
§ 371 (c)(1),
(2) Date: Jan. 3, 2023

(87) PCT Pub. No.: WO2022/156059
PCT Pub. Date: Jul. 28, 2022

(65) Prior Publication Data

US 2023/0303553 A1 Sep. 28, 2023

(30) Foreign Application Priority Data

Jan. 19, 2021 (CN) ........................ 202110066746.2

(51) Int. Cl.
*A61P 35/00* (2006.01)
*C07D 417/14* (2006.01)

(52) U.S. Cl.
CPC ............ *C07D 417/14* (2013.01); *A61P 35/00* (2018.01)

(58) Field of Classification Search
CPC ............................... C07D 417/14; A61P 35/00
See application file for complete search history.

(56) References Cited

FOREIGN PATENT DOCUMENTS

CN 102264725 A 11/2011
CN 105294683 A 2/2016
(Continued)

OTHER PUBLICATIONS

Saal et al.; Pharmaceutical salts: A summary on doses of salt formers from the Orange Book; Eur. J. Pharm. Sci., 49, 2013, 614-623. (Year: 2013).*
(Continued)

*Primary Examiner* — Kortney L. Klinkel
*Assistant Examiner* — Jackson J Hernandez
(74) *Attorney, Agent, or Firm* — Dilworth & Barrese, LLP

(57) ABSTRACT

The invention discloses a compound represented by the following general formula (I) or a pharmaceutically acceptable salt thereof. The invention also discloses a preparation method of the compound and use thereof in preventing and/or treating cancer or tumor-related diseases, in particular diseases such as breast cancer, prostate cancer, lung cancer, multiple myeloma, leukemia, gastric cancer, ovarian cancer, colon cancer, liver cancer, pancreatic cancer, human glioma and the like. The compound of the invention is expected to be developed into a new generation of anticancer drugs.
(Continued)

(I)

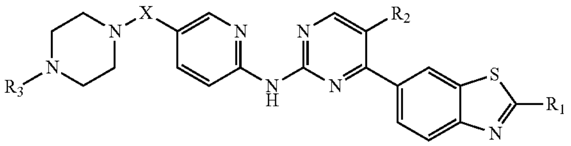

7 Claims, 2 Drawing Sheets

(56) References Cited

FOREIGN PATENT DOCUMENTS

| | | | |
|---|---|---|---|
| CN | 107266421 A | | 10/2017 |
| CN | 112390793 A | | 2/2021 |
| CN | 113149978 A | | 7/2021 |
| WO | WO 2018/045957 A1 | * | 3/2018 |

OTHER PUBLICATIONS

Fares Jawad et al:; "Landscape of combination therapy trials in breast cancer brain metastasis"; International Journal of Cancer, vol. 147, No. 7; Oct. 1, 2020, pp. 1939-1952; XP055832145.
Extended European Search Report dated Nov. 22, 2024.

* cited by examiner

CDK6/DYRK2 DUAL-TARGET INHIBITOR, AND PREPARATION METHOD THEREFOR AND USE THEREOF

TECHNICAL FIELD

The invention is related to the field of pharmaceutical chemistry, specifically a CDK6/DYRK2 dual-target inhibitor and preparation method therefor and use thereof.

BACKGROUND ART

Cyclin-dependent kinase 6 (CDK6) is a serine/tyrosine kinase that regulates the transition of the cell cycle from G1 to S. In the early G1 phase of the cell cycle, cyclin D binds to and activates CDK6, and the formed cyclin D-CDK6 complex promotes the phosphorylation of retinoblastoma protein (Rb). The phosphorylation of Rb leads to the release of transcription factor E2F, which accelerates the progression of the cell cycle from G1 to S. Up-regulation of the proto-oncogene CDK6 leads to an accelerated progression of the cell cycle from G1 to S, leading to an accelerated cell cycle and cell proliferation. Uncontrolled proliferation of cells is the main feature of cancer. Therefore, inhibition of CDK6 can slow the process of cell cycle transition from G1 phase to S phase, producing anti-proliferation and anti-cancer effects. However, the currently marketed CDK6 inhibitors, Palbociclib, Ribociclib and Abemaciclib, are highly toxic and have developed resistance.

Dual specificity tyrosine phosphorylation-regulated kinases (DYRK) and CDK belong to the CMGC family and play important regulatory roles in cell cycle and cell proliferation. DYRK2 regulates the phosphorylation of cell cycle-dependent Rpt3-T25, and promotes the degradation of CDK inhibitors such as p21 and p27, as well as the progression of cell cycle from G1 to S. The inhibition of DYRK2 can also slow the process of cell cycle transition from G1 phase to S phase, resulting in anti-proliferation and anti-cancer effects. Only a few DYRK2 inhibitors have been reported so far: the acridine compound LDN192960 was originally found to be a Haspin kinase inhibitor with some therapeutic effects on triple-negative breast cancer and multiple myeloma. Another drug curcumin, also confirmed to act on DYRK2 and DYRK3, can produce certain anti-multiple myeloma effect when combined with carfilzomib. However, the anticancer activity and target selectivity of the existing DYRK2 inhibitors still need to be optimized, and especially the drug-forming property needs to be further improved.

Targeted drugs exhibit the characteristics of strong drug efficacy and good safety. However, due to the complexity and integrity of cancer, when a single target drug inhibits one pathway of cancer, the related pathways will be activated to make up for the inhibited pathways, resulting in drug resistance.

SUMMARY OF THE INVENTION

Purpose of the invention: in order to solve the problem of drug resistance generated by the existing drugs in the single target treatment, the invention utilize the synergistic effect of CDK6 and DYRK2 and provides a compound or a pharmaceutically acceptable salt thereof which can be simultaneously targeted to CDK6 and DYRK2, wherein the compound is a CDK6/DYRK2 dual-target inhibitor; and by inhibiting DYRK2 and blocking a compensatory pathway of CDK6 at the same time, the anticancer activity of the compound is improved, and the drug resistance easily generated by a CDK6 single target drug is reduced. The invention also provides a specific preparation method of the compound and a medicament for preventing and/or treating cancer or tumor-related diseases, in particular diseases including breast cancer, prostate cancer, lung cancer, multiple myeloma, leukemia, gastric cancer, ovarian cancer, colon cancer, liver cancer, pancreatic cancer, human glioma and the like, and is expected to be developed into a new generation anticancer medicament.

Technical solution: the invention is related to a compound represented by the general formula (I) or a pharmaceutically acceptable salt thereof:

(I)

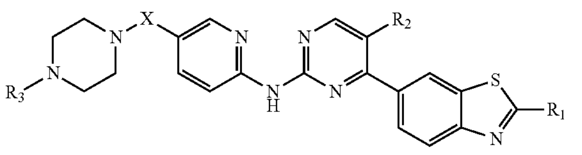

wherein,

X is selected from O, $(CH_2)_n$, C(O), NH or $S(O)_2$, n is 0 or 1;

$R_1$ is selected from hydrogen, deuterium, halogen, hydroxy group, mercapto group, cyano group, nitro group, $C_1$-$C_8$ alkyl group, halo-$C_1$-$C_8$ alkyl group, $C_1$-$C_8$ alkoxy group, $C_3$-$C_8$ cycloalkyl group, $C_6$-$C_{10}$ aryl group, $C_3$-$C_{10}$ heteroaryl group, $C_4$-$C_8$ heterocyclic group, —$C_{0\text{-}8}$—$NR_4R_5$;

$R_2$ is selected from hydrogen, deuterium, halogen, hydroxy group, mercapto group, cyano group, nitro group, $C_1$-$C_8$ alkyl group, $C_3$-$C_8$ cycloalkyl group;

$R_3$ is selected from hydrogen, deuterium, $C_1$-$C_8$ alkyl group, halo-$C_1$-$C_8$ alkyl group, $C_1$-$C_8$ alkoxy group, $C_3$-$C_8$ cycloalkyl group, —$C_{0\text{-}8}$—$S(O)_2R_6$, —$C_{0\text{-}8}$—C(O)$OR_7$;

$R_4$, $R_5$ are each independently selected from hydrogen, deuterium, $C_1$-$C_8$ alkyl group, halo-$C_1$-$C_8$ alkyl group, $C_1$-$C_8$ alkoxy group, $C_3$-$C_8$ cycloalkyl group;

$R_6$, $R_7$ are each independently selected from hydrogen, $C_1$-$C_8$ alkyl group, halo-$C_1$-$C_8$alkyl group, $C_3$-$C_8$ cycloalkyl group.

Preferably:

said X is C(O) or $(CH_2)_n$; n is 0 or 1;

said $R_1$ is hydrogen, $C_1$-$C_8$ alkyl group or —$C_{0\text{-}8}$—$NR_4R_5$, wherein, $R_4$, $R_5$ is selected from hydrogen, $C_1$-$C_8$ alkyl group or $C_3$-$C_8$ cycloalkyl group;

$R_2$ is hydrogen or halogen;

$R_3$ is hydrogen, $C_1$-$C_8$ alkyl group, —$C_{0\text{-}8}$—$S(O)_2R_6$ or —$C_{0\text{-}8}$—C(O)$OR_7$, wherein, $R_6$, $R_7$ is selected from $C_1$-$C_8$ alkyl group.

Preferably:

said X is C(O) or $(CH_2)_n$; n is 0 or 1;

said $R_1$ is hydrogen, $C_1$-$C_3$ alkyl group or —$NR_4R_5$, wherein, $R_4$, $R_5$ is selected from hydrogen, $C_1$-$C_3$ alkyl group, cyclopentane or cyclohexane;

$R_2$ is hydrogen or F;

$R_3$ is hydrogen, $C_1$-$C_4$ alkyl group, —$S(O)_2R_6$ or —C(O)$OR_7$, wherein, $R_6$, $R_7$ is selected from $C_1$-$C_4$ alkyl group.

Preferably:

said X is selected from $(CH_2)_n$ or C(O), n is 0 or 1;

said $R_1$ is selected from hydrogen, methyl group or —$NR_4R_5$, wherein, $R_4$, $R_5$ is selected from hydrogen, methyl group, ethyl group or cyclopentane;

said $R_2$ is F;

said $R_3$ is selected from hydrogen, ethyl group, isopropyl group, $-S(O)_2R_6$ or $-C(O)OR_7$, $R_6$ is methyl group, $R_7$ is selected from tert-butyl group or ethyl group.

Preferably:

said X is selected from $(CH_2)_n$ or C(O), n is 0 or 1;

said $R_1$ is selected from hydrogen, methyl group or $-NR_4R_5$, wherein, $R_4$, $R_5$ is selected from hydrogen, methyl group, ethyl group or cyclopentane;

said $R_2$ is F;

said $R_3$ is selected from hydrogen, ethyl group, isopropyl group or $-C(O)OR_7$, $R_7$ is selected from tert-butyl group.

Preferably:

said X is selected from $(CH_2)_n$ or C(O), n is 0 or 1;

said $R_1$ is selected from hydrogen, methyl group or $-NR_4R_5$, wherein, $R_4$ is selected from hydrogen, methyl group, ethyl group, said $R_5$ is selected from hydrogen, methyl group, ethyl group or cyclopentane;

said $R_2$ is F;

said $R_3$ is selected from hydrogen, ethyl group, isopropyl group or $-C(O)OR_7$, $R_7$ is selected from tert-butyl group.

Preferably, the compound of the present application is selected from I-1 to I-53:

| Compound | Chemical Name | Structural Formula |
|---|---|---|
| I-1 | (6-((4-(benzothiazole-6-yl)-5-fluoropyrimidine-2-yl)amino)pyridine-3-yl)(4-ethylpiperazine-1-yl)ketone | 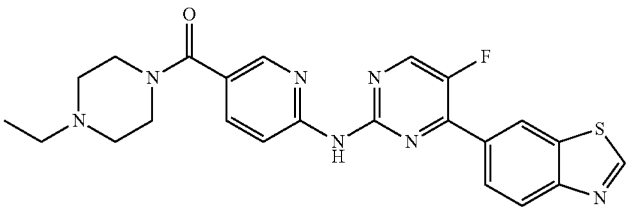 [SMILES: CCN1CCN(C(=O)c2ccc(Nc3ncc(F)c(-c4ccc5ncsc5c4)n3)nc2)CC1] |
| I-2 | 4-(benzothiazole-6-yl)-N-(5-((4-ethylpiperazine-1-yl)methyl)pyridine-2-yl)-5-fluoropyrimidine-2-amine | 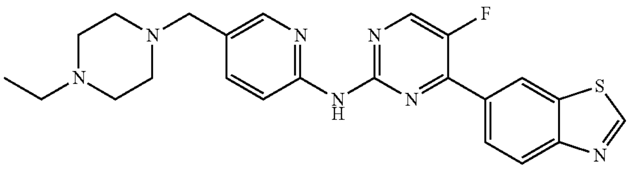 [SMILES: CCN1CCN(Cc2ccc(Nc3ncc(F)c(-c4ccc5ncsc5c4)n3)nc2)CC1] |
| I-3 | tert-butyl 4-((6-((4-(benzothiazole-6-yl)-5-fluoropyrimidine-2-yl)amino)pyridine-3-yl)methyl)piperazine-1-carboxylate | 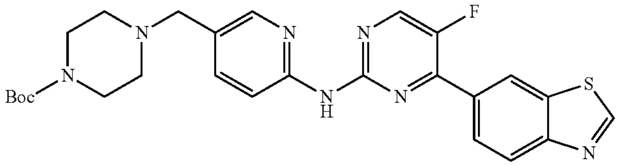 [SMILES: CC(C)(C)OC(=O)N1CCN(Cc2ccc(Nc3ncc(F)c(-c4ccc5ncsc5c4)n3)nc2)CC1] |
| I-4 | 4-(benzothiazole-6-yl)-5-fluoro-N-(5-(piperazine-1-ylmethyl)pyridine-2-yl)pyrimidine-2-amine hydrochloride | 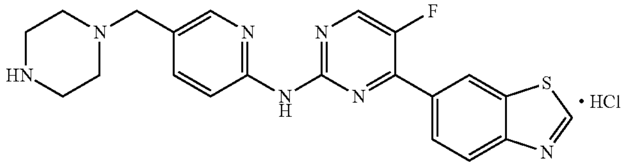 |
| I-5 | tert-butyl 4-(6-((4-(benzothiazole-6-yl)-5-fluoropyrimidine-2-yl)amino)nicotinoyl) piperazine-1-carboxylate | 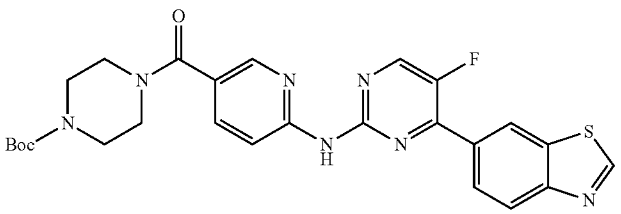 [SMILES: CC(C)(C)OC(=O)N1CCN(C(=O)c2ccc(Nc3ncc(F)c(-c4ccc5ncsc5c4)n3)nc2)CC1] |
| I-6 | 6-((4-(benzothiazole-6-yl)-5-fluoropyrimidine-2-yl)amino)pyridine-3-yl)(piperazine-1-yl)ketone hydrochloride | 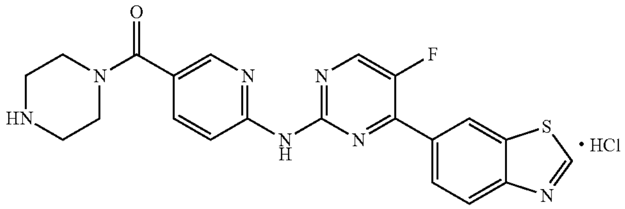 |

-continued

| Compound | Chemical Name | Structural Formula |
|---|---|---|
| I-7 | tert-butyl 4-(6-((4-(benzothiazole-6-yl)-5-fluoropyrimidine-2-yl)amino)pyridine-3-yl)piperazine-1-carboxylate | 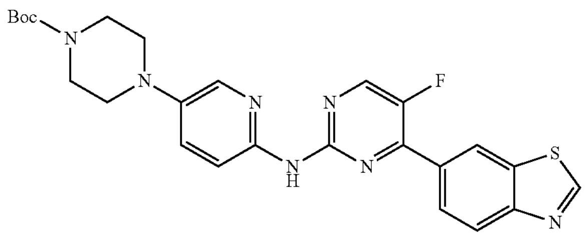 [SMILES: CC(C)(C)OC(=O)N1CCN(c2ccc(Nc3ncc(F)c(-c4ccc5ncsc5c4)n3)nc2)CC1] |
| I-8 | 4-(benzothiazole-6-yl)-5-fluoro-N-(5-(piperazine-1-yl)pyridine-2-yl)pyrimidine-2-amine hydrochloride | 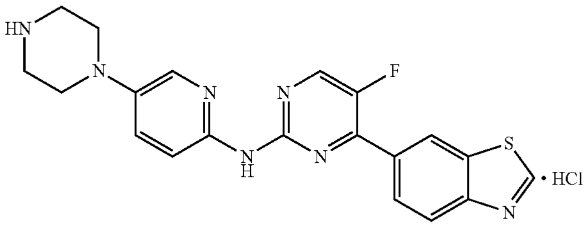 |
| I-9 | 4-(benzothiazole-6-yl)-5-fluoro-N-(5-((4-(methanesulfonyl) piperazine-1-yl)methyl)pyridine-2-yl)pyrimidine-2-amine | 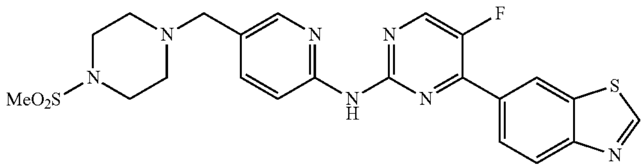 [SMILES: CS(=O)(=O)N1CCN(Cc2ccc(Nc3ncc(F)c(-c4ccc5ncsc5c4)n3)nc2)CC1] |
| I-10 | ethyl 4-((6-((4-(benzothiazole-6-yl)-5-fluoropyrimidine-2-yl)amino)pyridine-3-yl)methyl)piperazine-1-carboxylate | 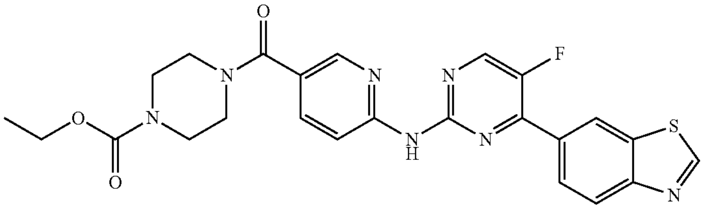 [SMILES: CCOC(=O)N1CCN(C(=O)c2ccc(Nc3ncc(F)c(-c4ccc5ncsc5c4)n3)nc2)CC1] |
| I-11 | 4-(benzothiazole-6-yl)-5-fluoro-N-(5-((4-isopropylpiperazine-1-yl)methyl)pyridine-2-yl)pyrimidine-2-amine | 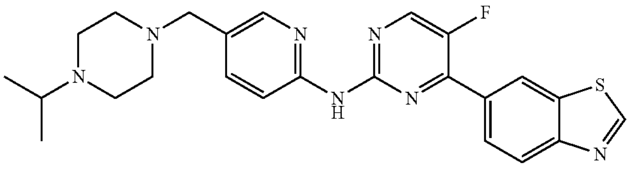 [SMILES: CC(C)N1CCN(Cc2ccc(Nc3ncc(F)c(-c4ccc5ncsc5c4)n3)nc2)CC1] |
| I-12 | (4-ethylpiperazine-1-yl)(6-((5-fluoro-4-(2-methylbenzothiazole-6-yl)pyrimidine-2-yl)amino)pyridine-3-yl)ketone | 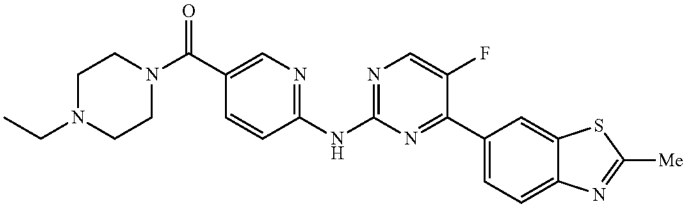 [SMILES: CCN1CCN(C(=O)c2ccc(Nc3ncc(F)c(-c4ccc5nc(C)sc5c4)n3)nc2)CC1] |
| I-13 | N-(5-((4-ethylpiperazine-1-yl)methyl)pyridine-2-yl)-5-fluoro-4-(2-methylbenzothiazole-6-yl)pyrimidine-2-amine | 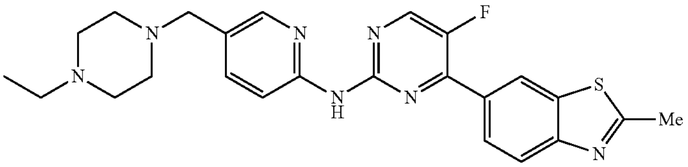 [SMILES: CCN1CCN(Cc2ccc(Nc3ncc(F)c(-c4ccc5nc(C)sc5c4)n3)nc2)CC1] |

-continued

| Compound | Chemical Name | Structural Formula |
|---|---|---|
| I-14 | tert-butyl 4-((6-((5-fluoro-4-(2-methylbenzothiazole-6-yl)pyrimidine-2-yl)amino)pyridine-3-yl)methyl)piperazine-1-carboxylate | 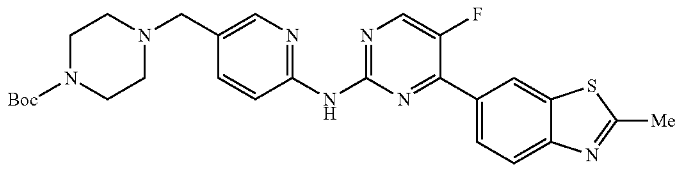 [SMILES: Cc1nc2ccc(-c3nc(Nc4ccc(CN5CCN(C(=O)OC(C)(C)C)CC5)cn4)ncc3F)cc2s1] |
| I-15 | 5-fluoro-4-(2-methylbenzothiazole-6-yl)-N-(5-(piperazine-1-ylmethyl)pyridine-2-yl)pyrimidine-2-amine hydrochloride | 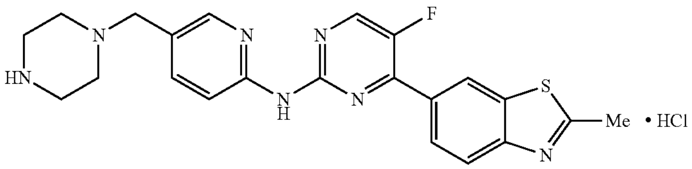 [SMILES: Cc1nc2ccc(-c3nc(Nc4ccc(CN5CCNCC5)cn4)ncc3F)cc2s1 ; "· HCl"] |
| I-16 | tert-butyl 4-(6-((5-fluoro-4-(2-methylbenzothiazole-6-yl)pyrimidine-2-yl)amino)nicotinoyl)piperazine-1-carboxylate | 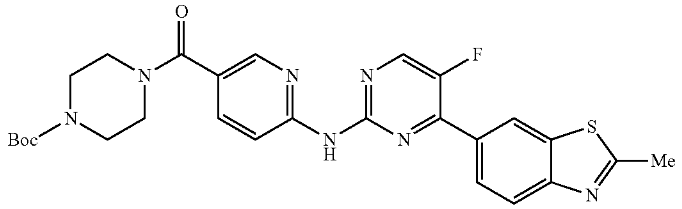 [SMILES: Cc1nc2ccc(-c3nc(Nc4ccc(C(=O)N5CCN(C(=O)OC(C)(C)C)CC5)cn4)ncc3F)cc2s1] |
| I-17 | (6-((5-fluoro-4-(2-methylbenzothiazole-6-yl)pyrimidine-2-yl)amino)pyridine-3-yl)(piperazine-1-yl)ketone hydrochloride | 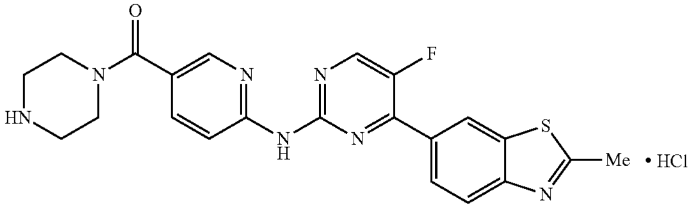 [SMILES: Cc1nc2ccc(-c3nc(Nc4ccc(C(=O)N5CCNCC5)cn4)ncc3F)cc2s1 ; "· HCl"] |
| I-18 | (6-((4-(2-(cyclopentylamino)benzothiazole-6-yl)-5-fluoropyrimidine-2-yl)amino)pyridine-3-yl)(4-ethylpiperazine-1-yl)ketone | 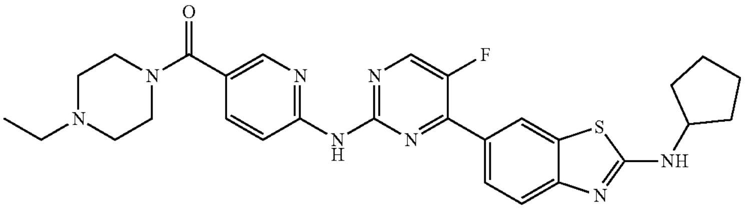 [SMILES: CCN1CCN(C(=O)c2ccc(Nc3ncc(F)c(-c4ccc5nc(NC6CCCC6)sc5c4)n3)nc2)CC1] |
| I-19 | N-cyclopentyl-6-(2-((5-((4-ethylpiperazine-1-yl)methyl)pyridine-2-yl)amino)-5-fluoropyrimidine-4-yl)benzothiazole-2-amine | 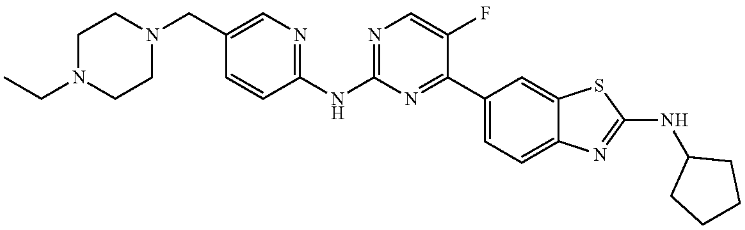 [SMILES: CCN1CCN(Cc2ccc(Nc3ncc(F)c(-c4ccc5nc(NC6CCCC6)sc5c4)n3)nc2)CC1] |
| I-20 | tert-butyl 4-((6-((4-(2-(cyclopentylamino)benzothiazole-6-yl)-5-fluoropyrimidine-2-yl)amino)pyridine-3-yl)methyl)piperazine-1-carboxylate | 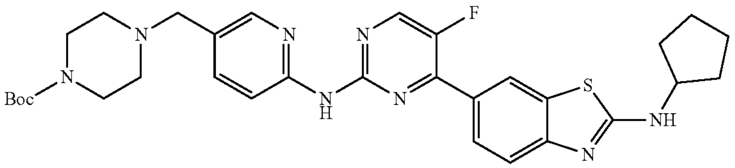 [SMILES: CC(C)(C)OC(=O)N1CCN(Cc2ccc(Nc3ncc(F)c(-c4ccc5nc(NC6CCCC6)sc5c4)n3)nc2)CC1] |

-continued

| Compound | Chemical Name | Structural Formula |
|---|---|---|
| I-21 | N-cyclopentyl-6-(5-fluoro-2-((5-(piperazine-1-ylmethyl)pyridine-2-yl)amino)pyrimidine-4-yl)benzothiazole-2-amine hydrochloride | 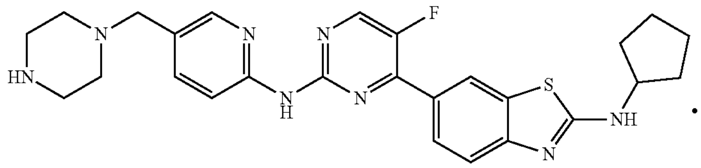 • HCl |
| I-22 | tert-butyl 4-(6-((4-(2-(cyclopentylamino) benzothiazole-6-yl)-5-fluoropyrimidine-2-yl)amino)nicotinoyl) piperazine-1-carboxylate | 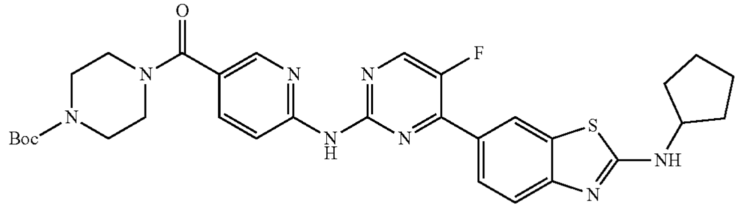 [SMILES: CC(C)(C)OC(=O)N1CCN(C(=O)c2ccc(Nc3ncc(F)c(-c4ccc5nc(NC6CCCC6)sc5c4)n3)nc2)CC1] |
| I-23 | (6-((4-(2-(cyclopentylamino) benzothiazole-6-yl)-5-fluoropyrimidine-2-yl)amino)pyridine-3-yl)(piperazine-1-yl) ketone hydrochloride | 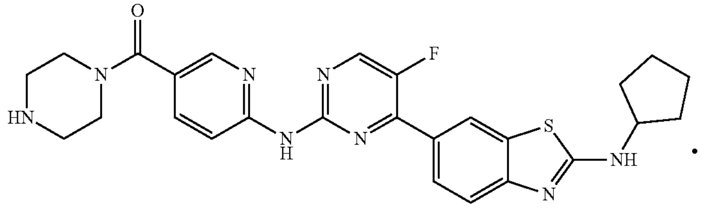 • HCl |
| I-24 | ethyl 4-((6-((4-(2-(cyclopentylamino) benzothiazole-6-yl)-5-fluoropyrimidine-2-yl)amino)pyridine-3-yl)methyl)piperazine-1-carboxylate | 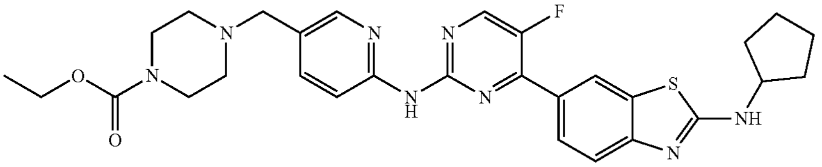 [SMILES: CCOC(=O)N1CCN(Cc2ccc(Nc3ncc(F)c(-c4ccc5nc(NC6CCCC6)sc5c4)n3)nc2)CC1] |
| I-25 | N-cyclopentyl-6-(5-fluoro-2-((5-((4-(methanesulfonyl) piperazine-1-yl)methyl)pyridine-2-yl)amino)pyrimidine-4-yl)benzothiazole-2-amine | 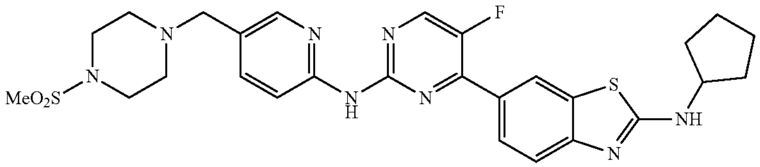 [SMILES: CS(=O)(=O)N1CCN(Cc2ccc(Nc3ncc(F)c(-c4ccc5nc(NC6CCCC6)sc5c4)n3)nc2)CC1] |
| I-26 | tert-butyl 4-(6-((4-(2-(cyclopentylamino) benzothiazole-6-yl)-5-fluoropyrimidine-2-yl)amino)pyridine-3-yl)piperazine-1-carboxylate | 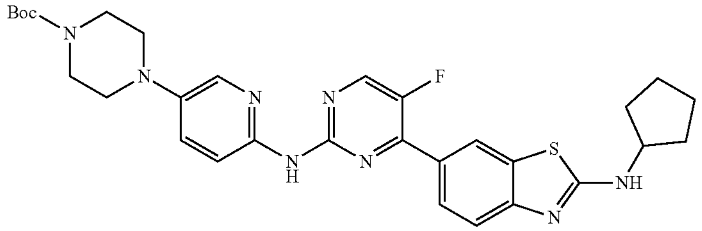 [SMILES: CC(C)(C)OC(=O)N1CCN(c2ccc(Nc3ncc(F)c(-c4ccc5nc(NC6CCCC6)sc5c4)n3)nc2)CC1] |
| I-27 | N-cyclopentyl-6-(5-fluoro-2-((5-(piperazine-1-yl)pyridine-2-yl)amino)pyrimidine-4-yl)benzothiazole-2-amine hydrochloride | 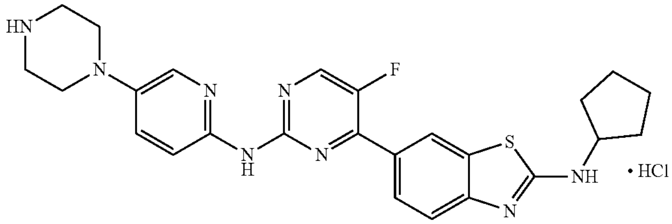 [SMILES: Fc1cnc(Nc2ccc(N3CCNCC3)cn2)nc1-c1ccc2nc(NC3CCCC3)sc2c1 ; "· HCl"] • HCl |

-continued

| Compound | Chemical Name | Structural Formula |
|---|---|---|
| I-28 | N-cyclopentyl-6-(5-fluoro-2-((5-((4-isopropylpiperazine-1-yl)methyl)pyridine-2-yl)amino)pyrimidine-4-yl)benzothiazole-2-amine | 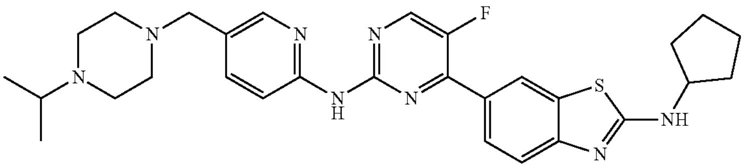 [SMILES: CC(C)N1CCN(Cc2ccc(Nc3ncc(F)c(-c4ccc5nc(NC6CCCC6)sc5c4)n3)nc2)CC1] |
| I-29 | (6-((4-(2-(cyclopentylamino)benzothiazole-6-yl)-5-fluoropyrimidine-2-yl)amino)pyridine-3-yl)(4-isopropylpiperazine-1-yl)ketone | 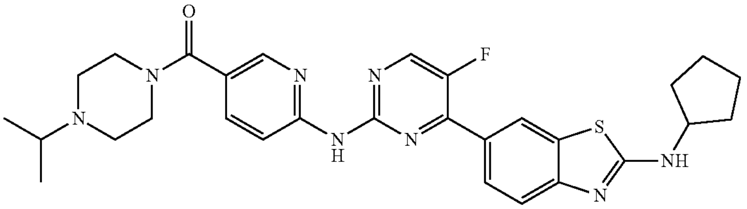 [SMILES: CC(C)N1CCN(C(=O)c2ccc(Nc3ncc(F)c(-c4ccc5nc(NC6CCCC6)sc5c4)n3)nc2)CC1] |
| I-30 | 6-(2-((5-((4-ethylpiperazine-1-yl)methyl)pyridine-2-yl)amino)-5-fluoropyrimidine-4-yl)-N,N-dimethylbenzothiazole-2-amine | 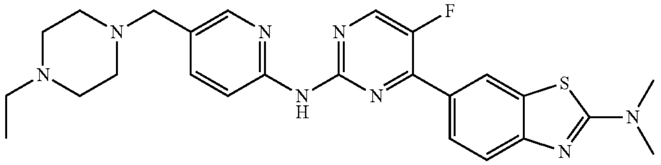 [SMILES: CCN1CCN(Cc2ccc(Nc3ncc(F)c(-c4ccc5nc(N(C)C)sc5c4)n3)nc2)CC1] |
| I-31 | (6-((4-(2-(dimethylamino)benzothiazole-6-yl)-5-fluoropyrimidine-2-yl)amino)pyridine-3-yl)(4-ethylpiperazine-1-yl)ketone | 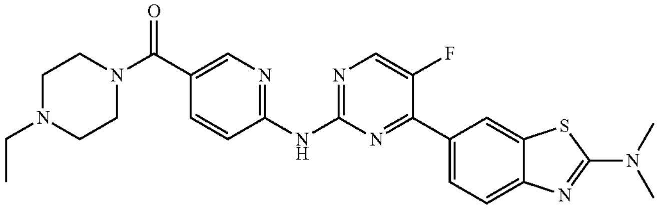 [SMILES: CCN1CCN(C(=O)c2ccc(Nc3ncc(F)c(-c4ccc5nc(N(C)C)sc5c4)n3)nc2)CC1] |
| I-32 | tert-butyl 4-((6-((4-(2-(dimethylamino)benzothiazole-6-yl)-5-fluoropyrimidine-2-yl)amino)pyridine-3-yl)methyl)piperazine-1-carboxylate | 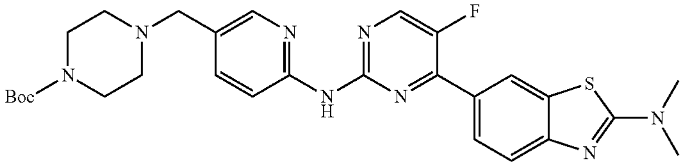 [SMILES: CN(C)c1nc2ccc(-c3nc(Nc4ccc(CN5CCN(C(=O)OC(C)(C)C)CC5)cn4)ncc3F)cc2s1] |
| I-33 | 6-(5-fluoro-2-((5-(piperazine-1-ylmethyl)pyridine-2-yl)amino)pyrimidine-4-yl)-N,N-dimethylbenzothiazole-2-amine hydrochloride | 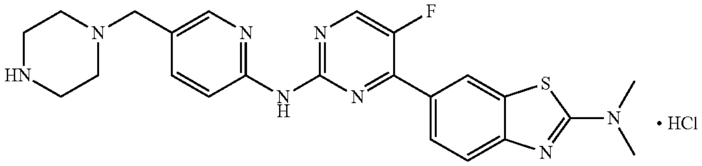 [SMILES: CN(C)c1nc2ccc(-c3nc(Nc4ccc(CN5CCNCC5)cn4)ncc3F)cc2s1 ; "· HCl"] |
| I-34 | tert-butyl 4-(6-((4-(2-(dimethylamino)benzothiazole-6-yl)-5-fluoropyrimidine-2-yl)amino)nicotinoyl)piperazine-1-carboxylate | 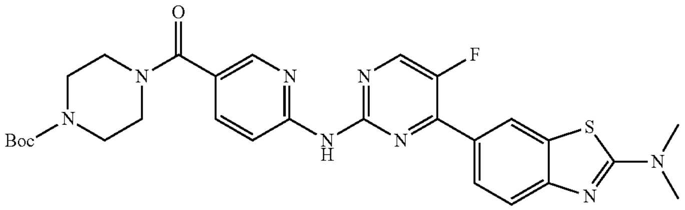 [SMILES: CN(C)c1nc2ccc(-c3nc(Nc4ccc(C(=O)N5CCN(C(=O)OC(C)(C)C)CC5)cn4)ncc3F)cc2s1] |
| I-35 | (6-((4-(2-(dimethylamino)benzothiazole-6-yl)-5-fluoropyrimidine-2-yl)amino)pyridine-3-yl)(piperazine-1-yl)ketone hydrochloride | 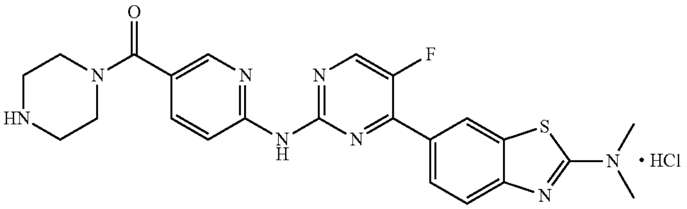 |

-continued

| Compound | Chemical Name | Structural Formula |
|---|---|---|
| I-36 | 6-(5-fluoro-2-((5-((4-isopropylpiperazine-1-yl)methyl)pyridine-2-yl)amino)pyrimidine-4-yl)-N,N-dimethylbenzothiazole-2-amine | 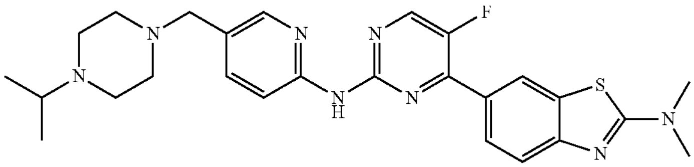 [SMILES: CC(C)N1CCN(Cc2ccc(Nc3ncc(F)c(-c4ccc5nc(N(C)C)sc5c4)n3)nc2)CC1] |
| I-37 | 6-(5-fluoro-2-((5-((4-(methanesulfonyl) piperazine-1-yl)methyl)pyridine-2-yl)amino)pyrimidine-4-yl)-N,N-dimethylbenzothiazole-2-amine | 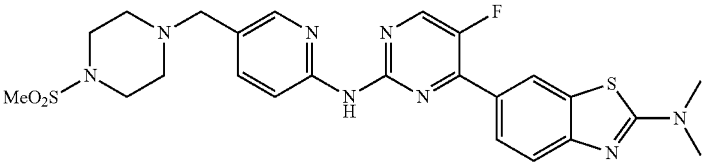 [SMILES: CN(C)c1nc2ccc(-c3nc(Nc4ccc(CN5CCN(S(C)(=O)=O)CC5)cn4)ncc3F)cc2s1] |
| I-38 | ethyl 4-((6-((4-(2-(dimethylamino) benzothiazole-6-yl)-5-fluoropyrimidine-2-yl)amino)pyridine-3-yl)methyl)piperazine-1-carboxylate | 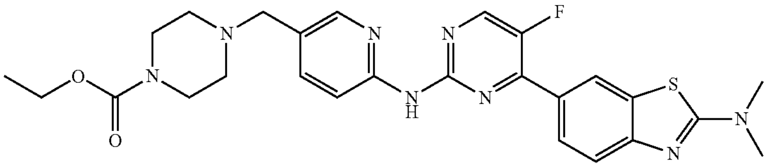 [SMILES: CCOC(=O)N1CCN(Cc2ccc(Nc3ncc(F)c(-c4ccc5nc(N(C)C)sc5c4)n3)nc2)CC1] |
| I-39 | (6-((4-(2-(dimethylamino) benzothiazole-6-yl)-5-fluoropyrimidine-2-yl)amino)pyridine-3-yl)(4-isopropylpiperazine-1-yl)ketone | 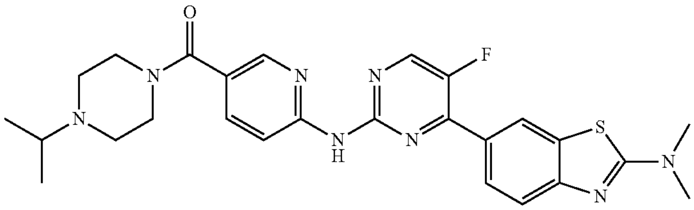 [SMILES: CC(C)N1CCN(C(=O)c2ccc(Nc3ncc(F)c(-c4ccc5nc(N(C)C)sc5c4)n3)nc2)CC1] |
| I-40 | tert-butyl 4-(6-((4-(2-(dimethylamino) benzothiazole-6-yl)-5-fluoropyrimidine-2-yl)amino)pyridine-3-yl)piperazine-1-carboxylate | 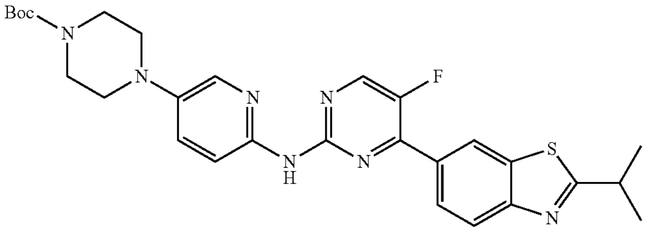 [SMILES: CC(C)c1nc2ccc(-c3nc(Nc4ccc(N5CCN(C(=O)OC(C)(C)C)CC5)cn4)ncc3F)cc2s1] |
| I-41 | 6-(5-fluoro-2-((5-(piperazine-1-yl)pyridine-2-yl)amino)pyrimidine-4-yl)-N,N-dimethylbenzothiazole-2-amine hydrochloride | 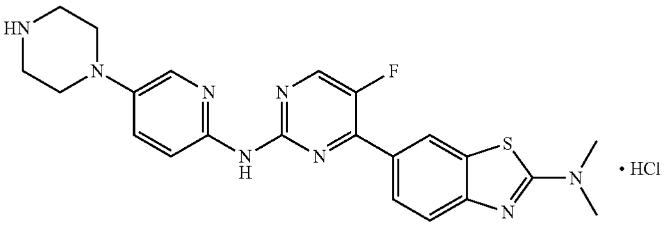 [SMILES: CN(C)c1nc2ccc(-c3nc(Nc4ccc(N5CCNCC5)cn4)ncc3F)cc2s1 ; "· HCl"] |
| I-42 | (6-((4-(2-(diethylamino) benzothiazole-6-yl)-5-fluoropyrimidine-2-yl)amino)pyridine-3-yl)(4-ethylpiperazine-1-yl)ketone | 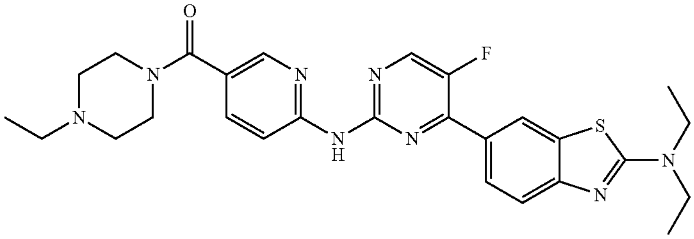 [SMILES: CCN1CCN(C(=O)c2ccc(Nc3ncc(F)c(-c4ccc5nc(N(CC)CC)sc5c4)n3)nc2)CC1] |

-continued

| Compound | Chemical Name | Structural Formula |
|---|---|---|
| I-43 | N,N-diethyl-6-(2-((5-((4-ethylpiperazine-1-yl)methyl)pyridine-2-yl)amino)-5-fluoropyrimidine-4-ylbenzothiazole-2-amine | 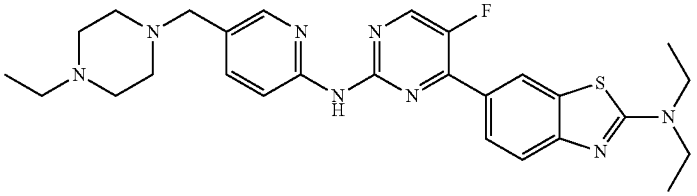 [SMILES: CCN1CCN(Cc2ccc(Nc3ncc(F)c(-c4ccc5nc(N(CC)CC)sc5c4)n3)nc2)CC1] |
| I-44 | tert-butyl 4-((6-((4-(2-(diethylamino) benzothiazole-6-yl)-5-fluoropyrimidine-2-yl)amino)pyridine-3-yl)methyl)piperazine-1-carboxylate | 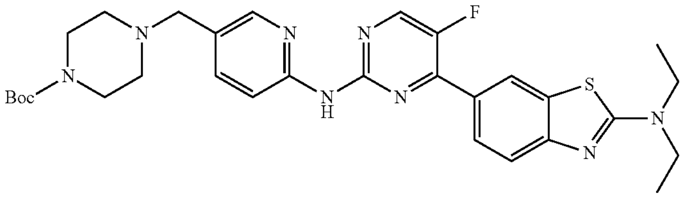 [SMILES: CCN(CC)c1nc2ccc(-c3nc(Nc4ccc(CN5CCN(C(=O)OC(C)(C)C)CC5)cn4)ncc3F)cc2s1] |
| I-45 | N,N-diethyl-6-(5-fluoro-2-((5-(piperazine-1-ylmethyl)pyridine-2-yl)amino)pyrimidine-4-yl)benzothiazole-2-amine hydrochloride | 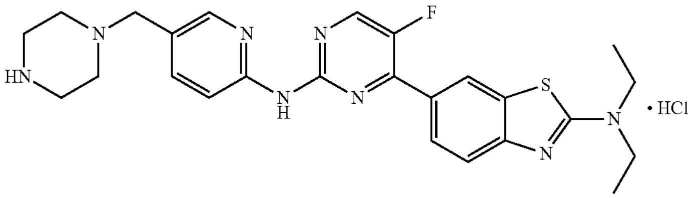 [SMILES: CCN(CC)c1nc2ccc(-c3nc(Nc4ccc(CN5CCNCC5)cn4)ncc3F)cc2s1 ; "· HCl"] |
| I-46 | tert-butyl 4-(6-((4-(2-(diethylamino) benzothiazole-6-yl)-5-fluoropyrimidine-2-yl)amino)nicotinoyl) piperazine-1-carboxylate | 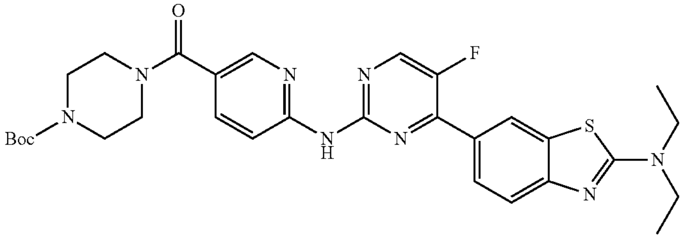 [SMILES: CCN(CC)c1nc2ccc(-c3nc(Nc4ccc(C(=O)N5CCN(C(=O)OC(C)(C)C)CC5)cn4)ncc3F)cc2s1] |
| I-47 | (6-((4-(2-(diethylamino) benzothiazole-6-yl)-5-fluoropyrimidine-2-yl)amino)pyridine-3-yl)(piperazine-1-yl)ketone hydrochloride | 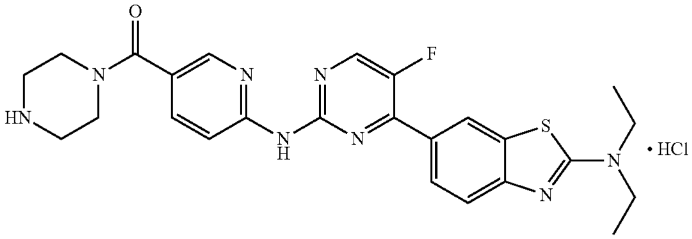 [SMILES: CCN(CC)c1nc2ccc(-c3nc(Nc4ccc(C(=O)N5CCNCC5)cn4)ncc3F)cc2s1 ; "· HCl"] |
| I-48 | N,N-diethyl-6-(5-fluoro-2-((5-((4-(methanesulfonyl) piperazine-1-yl)methyl)pyridine-2-yl)amino)pyrimidine-4-yl)benzothiazole-2-amine | 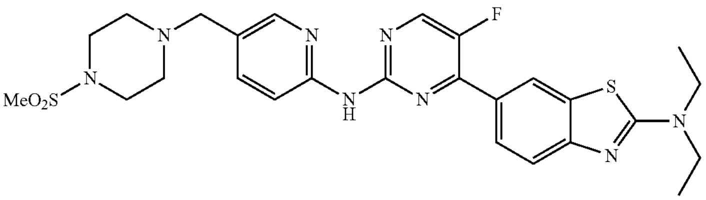 [SMILES: CCN(CC)c1nc2ccc(-c3nc(Nc4ccc(CN5CCN(S(C)(=O)=O)CC5)cn4)ncc3F)cc2s1] |
| I-49 | ethyl 4-((6-((4-(2-(diethylamino) benzothiazole-6-yl)-5-fluoropyrimidine-2-yl)amino)pyridine-3-yl)methyl)piperazine-1-carboxylate | 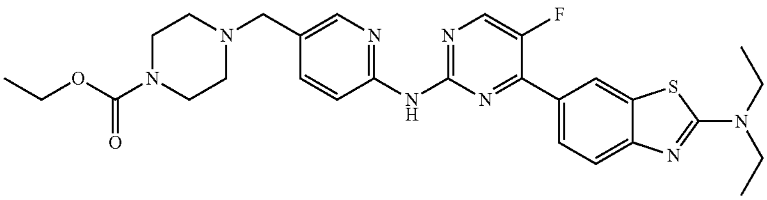 [SMILES: CCOC(=O)N1CCN(Cc2ccc(Nc3ncc(F)c(-c4ccc5nc(N(CC)CC)sc5c4)n3)nc2)CC1] |

-continued

| Compound | Chemical Name | Structural Formula |
|---|---|---|
| I-50 | N,N-diethyl-6-5-fluoro-2-((5-((4-isopropylpiperazine-1-yl)methyl)pyridine-2-yl)amino)pyrimidine-4-yl)benzothiazole-2-amine | 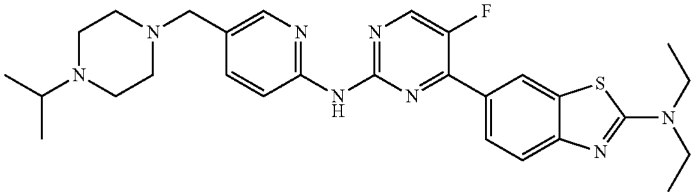 [SMILES: CCN(CC)c1nc2ccc(-c3nc(Nc4ccc(CN5CCN(C(C)C)CC5)cn4)ncc3F)cc2s1] |
| I-51 | (6-((4-(2-(diethylamino) benzothiazole-6-yl)-5-fluoropyrimidine-2-yl)amino)pyridine-3-yl) (4-isopropylpiperazine-1-yl)ketone | 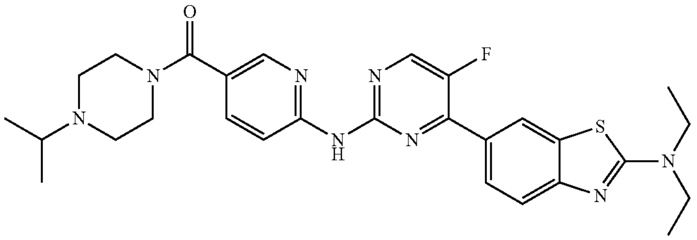 [SMILES: CCN(CC)c1nc2ccc(-c3nc(Nc4ccc(C(=O)N5CCN(C(C)C)CC5)cn4)ncc3F)cc2s1] |
| I-52 | tert-butyl 4-(6-((4-(2-(diethylamino) benzothiazole-6-yl)-5-fluoropyrimidine-2-yl) amino)pyridine-3-yl) piperazine-1-carboxylate | 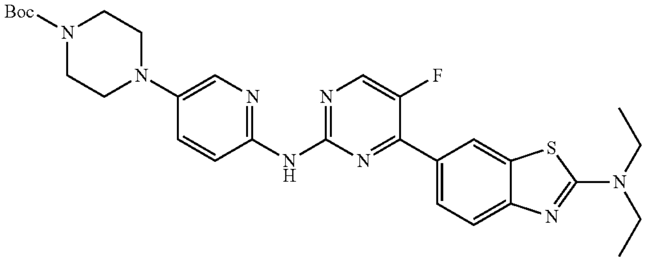 [SMILES: CCN(CC)c1nc2ccc(-c3nc(Nc4ccc(N5CCN(C(=O)OC(C)(C)C)CC5)cn4)ncc3F)cc2s1] |
| I-53 | N,N-diethyl-6-(5-fluoro-2-((5-(piperazine-1-yl) pyridine-2-yl)amino)pyrimidine-4-yl)benzothiazole-2-amine hydrochloride | 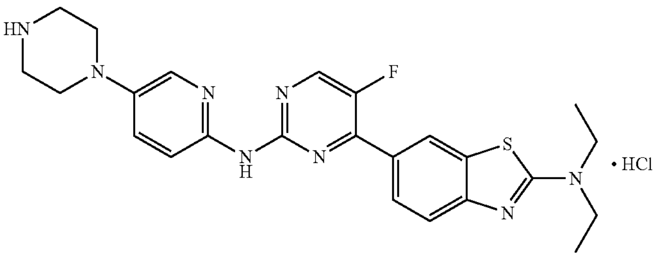 [SMILES: CCN(CC)c1nc2ccc(-c3nc(Nc4ccc(N5CCNCC5)cn4)ncc3F)cc2s1 ; "· HCl"] |

Preferably:

said X is selected from: $(CH_2)_n$ or C(O), 为0 or 1;

said $R_1$ is selected from: hydrogen, methyl group or $—NR_4R_5$, wherein, $R_4$ and $R_5$ are each independently selected from hydrogen, methyl group, ethyl group; or $R_4$ is h, $R_5$ is cyclopentane;

said $R_2$ is F;

said $R_3$ is selected from hydrogen, ethyl group, isopropyl group.

The above pharmaceutically acceptable salt is the acidic addition salt of the compound of the general formula (I), wherein the salt-forming acid include inorganic acid and organic acid, wherein said inorganic acid includes: hydrochloric acid, sulfuric acid, phosphoric acid and methanesulfonic acid, and said organic acid includes acetic acid, trichloroacetic acid, propionic acid, butyric acid, maleic acid, p-toluenesulfonic acid, malic acid, malonic acid, cinnamic acid, citric acid, fumaric acid, camphoric acid, digluconic acid, aspartic acid and tartaric acid.

Preferably, the pharmaceutically acceptable salt of the invention is hydrochloride.

The invention is related to a preparation method of the compound of the general formula (I) preparing the compound (I) from a compound (A) and a Compound (B) through coupling reaction under the action of a palladium catalyst:

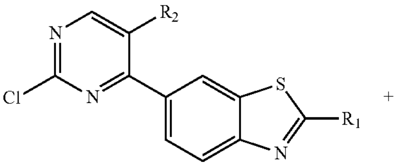

(A)

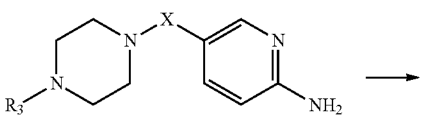

(B)

-continued

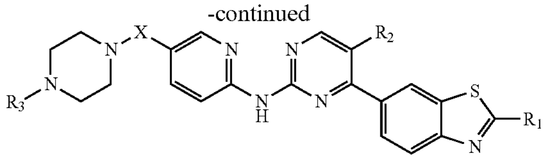

(I)

wherein,

X is selected from O, $(CH_2)_n$, C(O), NH or $S(O)_2$, n is 0 or 1;

$R_1$ is selected from hydrogen, deuterium, halogen, hydroxy group, mercapto group, cyano group, nitro group, $C_1$-$C_8$ alkyl group, halo-$C_1$-$C_8$ alkyl group, $C_1$-$C_8$ alkoxy group, $C_3$-$C_8$ cycloalkyl group, $C_6$-$C_{10}$ aryl group, $C_3$-$C_{10}$ heteroaryl group, $C_4$-$C_8$ heterocyclic group, —$C_{0-8}$-$NR_4R_5$ $R_2$ is selected from hydrogen, deuterium, halogen, hydroxy group, mercapto group, cyano group, nitro group, $C_1$-$C_8$ alkyl group, $C_3$-$C_8$ cycloalkyl group;

$R_3$ is selected from hydrogen, deuterium, $C_1$-$C_8$ alkyl group, halo-$C_1$-$C_8$ alkyl group, $C_1$-$C_8$ alkoxy group, $C_3$-$C_8$ cycloalkyl group, —$C_{0-8}$—$S(O)_2R_6$, —$C_{0-8}$—C(O)$OR_7$;

$R_4$, $R_5$ are each independently selected from hydrogen, deuterium, $C_1$-$C_8$ alkyl group, halo-$C_1$-$C_8$ alkyl group, $C_1$-$C_8$ alkoxy group, $C_3$-$C_8$ cycloalkyl group;

$R_6$, $R_7$ are each independently selected from hydrogen, $C_1$-$C_8$ alkyl group, halo-$C_1$-$C_8$ alkyl group, $C_3$-$C_8$ cycloalkyl group.

Preferably, said reaction is conducted under an argon protection atmosphere; and the reaction temperature is 95-105° C., and preferably the reaction temperature is 100° C.

The invention further discloses a pharmaceutical composition, comprising the abovementioned compound of general formula (I) or a pharmaceutically acceptable salt thereof or an isomer thereof, and a pharmaceutically acceptable carrier.

The pharmaceutically acceptable carrier is referred to an excipient or diluent that does not cause significant irritation to the organism and does not interfere with the biological activity and properties of the compound administered.

The invention is related to the use of the compound or a pharmaceutically acceptable salt thereof in the manufacture of a medicament of CDK6/DYRK2 dual-target inhibitor.

The medicament of CDK6/DYRK2 dual-target inhibitor can be used to treat cancer or tumor related disease.

The invention is related to the use of the compound or a pharmaceutically acceptable salt thereof in the manufacture of a medicament for preventing and/or treating cancer or tumor related disease. The cancer or tumor related disease includes breast cancer, prostate cancer, lung cancer, multiple myeloma, leukemia, gastric cancer, ovarian cancer, colon cancer, liver cancer, pancreatic cancer and human glioma.

The invention is related to the compound of general formula (I) or a pharmaceutically acceptable salt thereof, having CDK6/DYRK2 dual-target inhibitory activity, and showing therapeutic effects on cell malignant proliferation tumor.

The terms in the invention have the following meanings unless otherwise specified.

The term "alkyl group" means a linear or branched saturated hydrocarbon group having the number of carbon atoms.

The term "$C_1$-$C_8$ alkyl group" is referred to a linear or branched saturated hydrocarbon group having 1 to 8 carbon atoms. $C_1$-$C_8$ alkyl group includes but is not limited to methyl group, ethyl group, n-propyl group, isopropyl group, n-butyl group, isobutyl group, tert-butyl group, n-pentyl group, isopentyl group, neopentyl group, n-hexyl group, isohexyl group, 2,2-dimethylbutyl group and 2,3-dimethylbutyl group and the like. The term "$C_1$-$C_3$ alkyl group" is referred to a linear or branched saturated hydrocarbon group having 1 to 3 carbon atoms.

The term "alkoxy group" means O— alkyl group. The term "$C_1$-$C_8$ alkoxy group" is referred to a group having O—$C_1$-$C_8$ alkyl group.

"C(O)" means "—C(O)—", specifically carbonyl group. The term "halogen" is fluorine, chlorine, bromine or iodine. Preferably, it is fluorine, chlorine, bromine.

The term "halo-alkyl group" means an alkyl group having at least one (including one) halogen substituents.

The term "cycloalkyl group" means a saturated monocyclic or polycyclic ring structure consisting of carbon atoms.

The term "$C_3$-$C_8$ cycloalkyl group" is referred to a saturated monocyclic or polycyclic ring structure having in total 3 to 8 atoms. $C_3$-$C_6$ cycloalkyl group includes but is not limited to cyclopropyl group, cyclobutyl group, cyclopentyl group, cyclohexyl group.

The term "cycloalkenyl" is referred to a monocyclic or polycyclic alkyl substituent having at least one cyclic carbon-carbon double bonds.

The term "$C_3$-$C_8$ cycloalkenyl" is referred to a cycloalkenyl having 3 to 8 carbon atoms. $C_3$-$C_8$ cycloalkenyl includes but is not limited to cyclopentenyl group, cyclobutenyl group.

The term "$C_2$-$C_8$ alkenyl" is referred to a linear or branched hydrocarbon group having one or more carbon-carbon double bonds and having 2 to 8 carbon atoms.

The term "$C_2$-$C_8$ alkynyl" is referred to a linear or branched hydrocarbon group having one or more carbon-carbon triple bonds and having 2 to 8 carbon atoms.

The term "$C_6$-$C_{10}$ aryl group" means a monocyclic or fused polycyclic group consisting of 6 to 10 carbon atoms, having a completely conjugated 71 electron system. Typically, it includes but is not limited to phenyl group, naphthyl group.

The term "heteroaryl group" means a monocyclic or fused cyclic group, having one, two, three or four cyclic heteroatoms selected from a group consisting of N, O or S, with the remainder of cyclic atoms being C, further having a completely conjugated π electron system. The term "$C_3$-$C_{10}$ heteroaryl group" is referred to a heteroaryl group having 3 to 10 carbon atoms in its ring. $C_3$-$C_{10}$ heteroaryl group includes but is not limited to pyrrole, furan, thiophene, imidazole, oxazole, thiazole, pyrazole, pyrimidine, pyridine.

The term "heterocyclic group" is heterocycloalkyl group, and means a monocyclic or fused cyclic group having one or more heteroatoms of N, O or S. The term "$C_4$-$C_8$ heterocyclic group" is referred to a heterocyclic group having 4 to 8 carbon atoms in its ring. $C_4$-$C_8$ heterocyclic group includes but is not limited to piperazino group, morpholino group, piperidino group, pyrrolidino group and the like.

Beneficial Effects: Compared with the prior art, the invention has the follow significant characteristics that, the invention discloses a novel compound represented by the general formula (i), which can simultaneously inhibit multiple pathways of cancer, has good treatment effect, low toxicity, good drug metabolism characteristic and is difficult to generate drug resistance, and can be used for manufacturing a medicament for treating cancer or tumor related diseases. The invention also discloses a preparation method of the compound of the general formula (I).

DETAILED DESCRIPTION OF THE INVENTION

Figure 1:
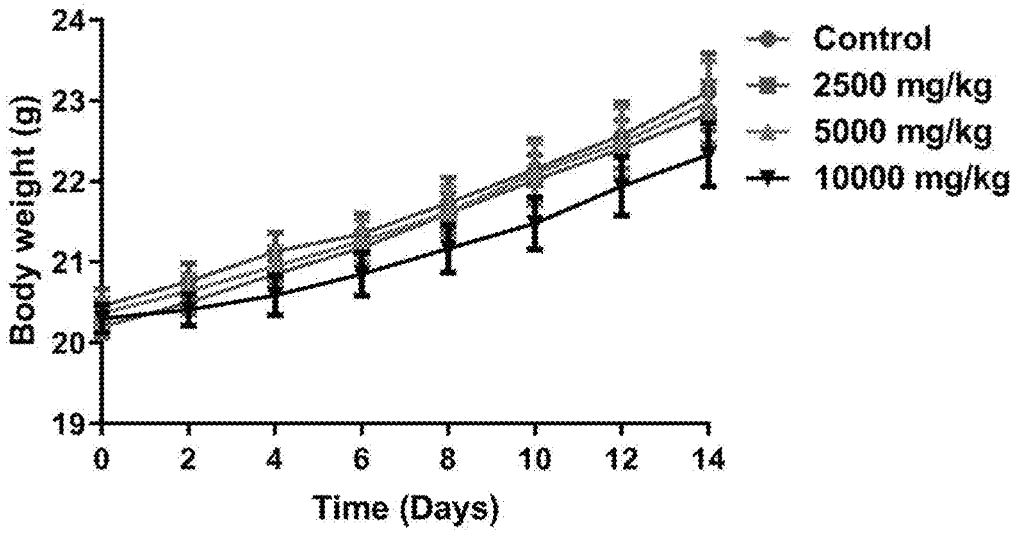
FIG. 1 shows the change in body weight of a mouse in the acute toxicity assay of the invention.

The present application is described in detail below with reference to specific embodiments.

I. Synthesis of Intermediate Reactants

Reactant (A) and reactant (B) can be purchased directly or developed independently, and the cost can be significantly reduced by independent development. The independently developed specific preparation methods of the reactant (A) and the reactant (B) are as follow:

(1) The Synthesis of 6-(2-chloro-5-fluoropyrimidine-4-yl)benzothiazole (A-1)

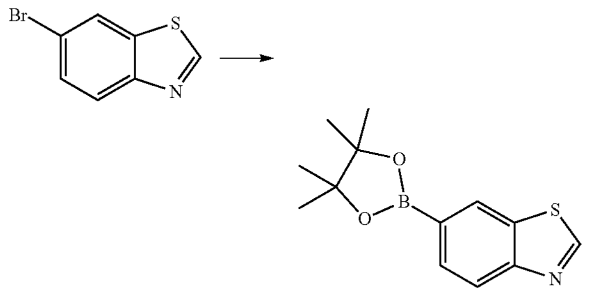

Step 1. The synthesis of 6-(4,4,5,5-tetramethyl-1,3,2-dioxaborolane-2-yl)benzothiazole: 6-bromobenzothiazole (0.43 g, 2.0 mmol) was dissolved in DMF (10 mL). Then pinacol borate (0.53 g, 2.1 mmol), $Pd(dppf)Cl_2$ (22 mg, 0.06 mmol), potassium acetate (0.59 g, 6.0 mmol) were added. The reaction was replaced with argon three times, heated to 80° C., and reacted for 24 h. The mixture was cooled, filtered and concentrated, and purified by flash silica gel column chromatography to obtain Compound 6-(4,4,5,5-tetramethyl-1,3,2-dioxaborolane-2-yl)benzothiazole (0.47 g, 90% yield).

$^1$HNMR (300 MHz, $CDCl_3$) δ 9.07 (s, 1H), 8.46 (s, 1H), 8.14 (d, J=8.2 Hz, 1H), 7.94 (dd, J=8.2, 1.1 Hz, 1H), 1.38 (s, 12H).

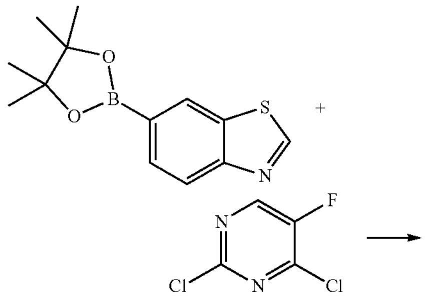

-continued

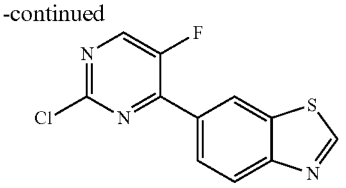

Step 2. The synthesis of 6-(2-chloro-5-fluoropyrimidine-4-yl)benzothiazole (A-1): Compound 2, 4-dichloro-5-fluoropyrimidine (0.23 g, 1.4 mmol) were weighed and added into 250 mL a three-necked flask. Then $Pd(PPh_3)_2Cl_2$(21 mg, 0.03 mmol), sodium carbonate (0.27 g, 2.5 mmol), glyme (10 mL) and $H_2O$ (0.25 mL) were added. The reaction was replaced with argon three times, heated to 80° C. Compound 6-(4,4,5,5-tetramethyl-1,3,2-dioxaborolane-2-yl)benzothiazole (0.26 g, 1.0 mmol) was dissolved in glyme (5 mL), added dropwise into a three-necked flask, and reacted for 16 h. The mixture was cooled, filtered and concentrated, and purified by flash silica gel column chromatography to obtain Compound 6-(2-chloro-5-fluoropyrimidine-4-yl)benzothiazole (0.22 g, 82% yield). $^1$HNMR (300 MHz, $CDCl_3$) δ 9.17 (s, 1H), 8.84 (d, J=1.7 Hz, 1H), 8.58 (d, J=3.1 Hz, 1H), 8.37-8.24 (m, 2H).

(2) The Synthesis of 6-(2-chloro-5-fluoropyrimidine-4-yl)-2-methylbenzothiazole (A-2)

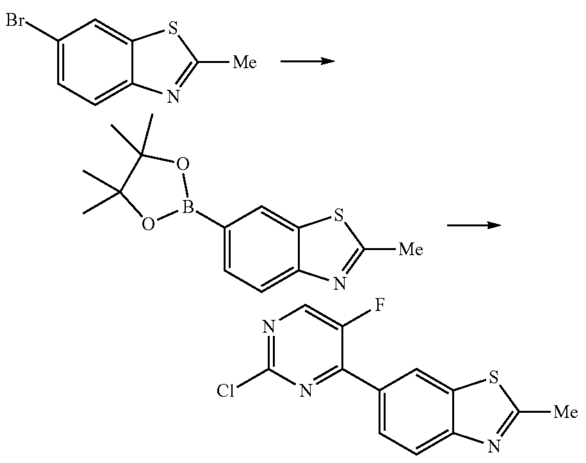

Referring to the synthesis of Compound (A-1), the yields were respectively 90% and 84%. $^1$H NMR (400 MHz, $CDCl_3$) δ 8.70 (d, J=1.9 Hz, 1H), 8.55 (d, J=3.1 Hz, 1H), 8.28-8.25 (m, 1H), 8.07 (d, J=8.6 Hz, 1H), 2.90 (s, 3H).

(3) The Synthesis of 6-(2-chloro-5-fluoropyrimidine-4-yl)-N-cyclopentylbenzothiazole-2-amine (A-3)

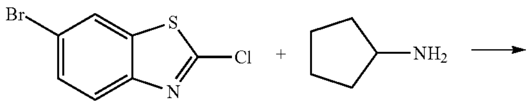

-continued

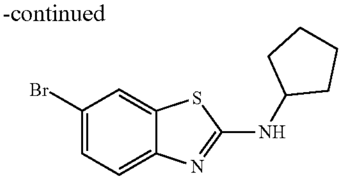

Step 1. The synthesis of 6-bromo-N-cyclopentylbenzothiazole-2-amine: 6-bromo-2-chlorobenzothiazole (0.50 g, 2.0 mmol) was dissolved in DMSO (10 mL), and cyclopentylamine (0.19 g, 2.2 mmol) and N-ethyldiisopropylamine (0.39 g, 3.0 mmol) were added. The reaction was replaced with argon three times, heated to 80° C., and reacted for 12 h. The mixture was cooled, filtered and concentrated, and purified by flash silica gel column chromatography to obtain Compound 6-bromo-N-cyclopentylbenzothiazole-2-amine (0.53 g, 90% yield). $^1$H NMR (400 MHz, $CDCl_3$) δ 7.68 (d, J=1.7 Hz, 1H), 7.38-7.33 (m, 2H), 6.28 (s, 1H), 3.98-3.93 (m, 1H), 2.14-2.04 (m, 2H), 1.72-1.54 (m, 6H).

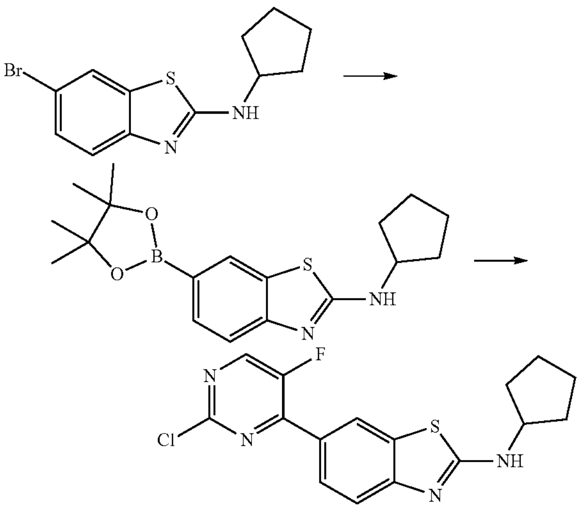

Step 2. The synthesis of 6-(2-chloro-5-fluoropyrimidine-4-yl)-N-cyclopentylbenzothiazole-2-amine (A-3): Referring to the synthesis of Compound (A-1), the yields were respectively 88% and 83%. $^1$H NMR (400 MHz, $CDCl_3$) δ 8.49 (d, J=1.9 Hz, 1H), 8.46 (d, J=3.5 Hz, 1H), 8.17-8.14 (m, 1H), 7.58 (d, J=8.6 Hz, 1H), 5.88 (s, 1H), 4.13-4.07 (m, 1H), 2.19-2.11 (m, 2H), 1.77-1.61 (m, 6H).

(4) The Synthesis of 6-(2-chloro-5-fluoropyrimidine-4-yl)-N,N-dimethylbenzothiazole-2-amine (A-4)

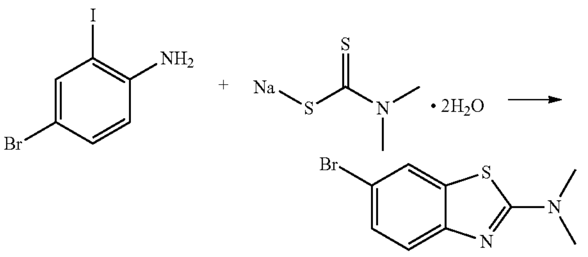

Step 1. The synthesis of 6-bromo-N,N-dimethylbenzothiazole-2-amine: 4-bromo-2-iodoaniline (0.60 g, 2.0 mmol), sodium dimethyldithiocarbamate dihydrate (0.72 g, 4.0 mmol), copper acetate (0.36 g, 2.0 mmol) and potassium carbonate (0.55 g, 4.0 mmol) were weighed and dissolved in DMF (10 mL), heated to 120° C., and reacted for 6 h. The mixture was cooled, filtered and concentrated, and purified by flash silica gel column chromatography to obtain Compound 6-bromo-N,N-dimethylbenzothiazole-2-amine (0.44 g, 85% yield). $^1$H NMR (400 MHz, $CDCl_3$) δ 7.69 (d, J=1.9 Hz, 1H), 7.41-7.35 (m, 2H), 3.20 (s, 6H).

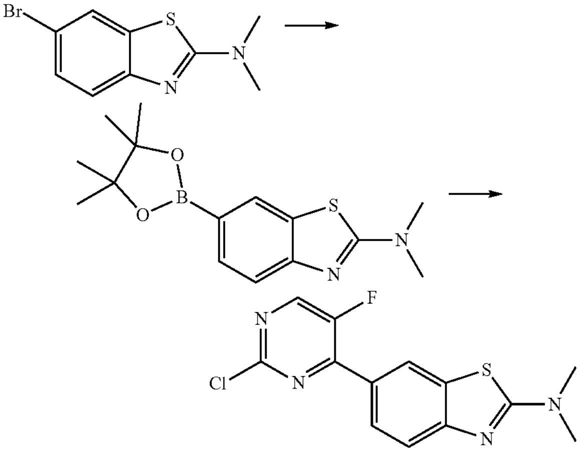

Step 2. The synthesis of 6-(2-chloro-5-fluoropyrimidine-4-yl)-N,N-dimethylbenzothiazole-2 amine (A-4): Referring to the synthesis of Compound (A-1), the yields were 88% and 80%. $^1$H NMR (400 MHz, $CDCl_3$) δ 8.49 (d, J=1.9 Hz, 1H), 8.45 (d, J=3.6 Hz, 1H), 8.17-8.14 (m, 1H), 7.62 (d, J=8.7 Hz, 1H), 3.27 (s, 6H).

(5) The Synthesis of 6-(2-chloro-5-fluoropyrimidine-4-yl)-N,N-diethylbenzothiazole-2-amine (A-5)

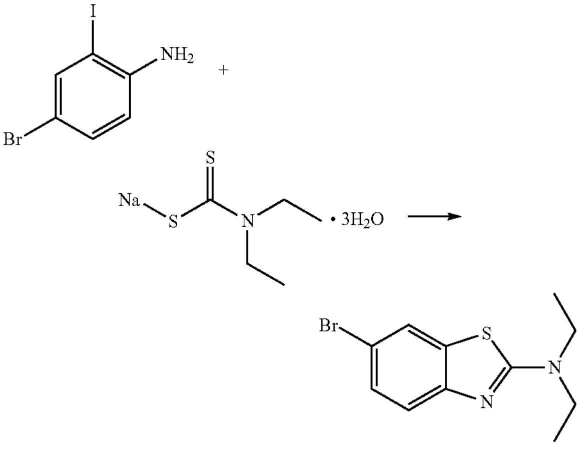

Step 1. The synthesis of 6-bromo-N,N-diethylbenzothiazole-2-amine: 4-bromo-2-iodoaniline (0.60 g, 2.0 mmol), sodium diethyldithiocarbamate trihydrate (0.90 g, 4.0 mmol), copper acetate (0.36 g, 2.0 mmol) and potassium carbonate (0.55 g, 4.0 mmol) were weighed and dissolved in DMF (10 mL), heated to 120° C., and reacted for 6 h. The mixture was cooled, filtered and concentrated, and purified by flash silica gel column chromatography to obtain Compound 6-bromo-N,N-dimethylbenzothiazole-2-amine (0.46 g, 80% yield).

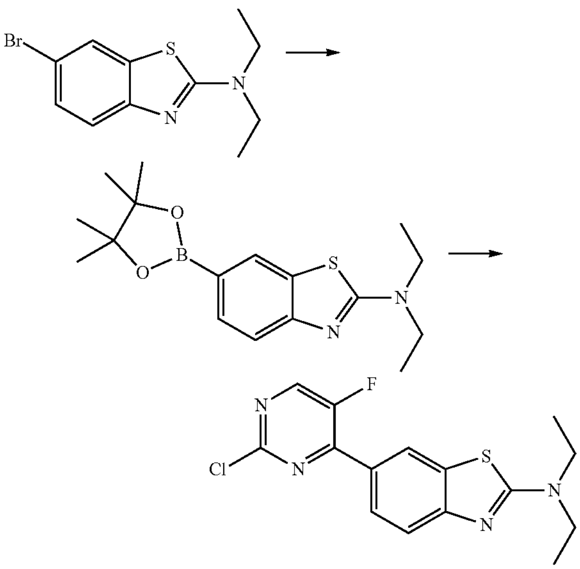

Step 2. The synthesis of 6-(2-chloro-5-fluoropyrimidine-4-yl)-N,N-diethylbenzothiazole-2-amine (A-5): Referring to the synthesis of Compound (A-1), the yields were 90% and 82%. $^1$H NMR (300 MHz, $CDCl_3$) δ 8.44 (dd, J=8.8, 2.7 Hz, 2H), 8.13 (d, J=8.6 Hz, 1H), 7.58 (d, J=8.7 Hz, 1H), 3.61 (q, J=7.2 Hz, 4H), 1.32 (t, J=7.2 Hz, 6H).

(6) The Synthesis of (6-aminopyridine-3-yl)(4-ethylpiperazine-1-yl)ketone (B-1)

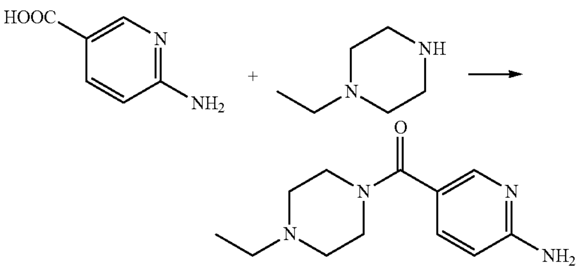

6-aminonicotinic acid (0.28 g, 2.0 mmol), N,N'-carbonyldiimidazole (0.39 g, 2.4 mmol) were weighed and dissolved in DMF(5 mL), and reacted at 70° C. for 10 min. The reaction was stirred at room temperature for 1 h, and N-ethylpiperazine (0.46 g, 4.0 mmol) was added. The reaction was conducted overnight at room temperature, concentrated, and purified by flash silica gel column chromatography to obtain Compound (6-aminopyridine-3-yl)(4-ethylpiperazine-1-yl)ketone (0.40 g, 85% yield). $^1$H NMR (300 MHz, $CDCl_3$) δ 8.19-8.17 (m, 1H), 7.57-7.54 (m, 1H), 6.51-6.48 (m, 0.9 Hz, 1H), 4.79 (s, 2H), 3.73-3.60 (m, 4H), 2.49-2.42 (m, 6H), 1.13-1.08 (m, 3H).

(7) The Synthesis of 5-((4-ethylpiperazine-1-yl)methyl)pyridine-2-amine (B-2)

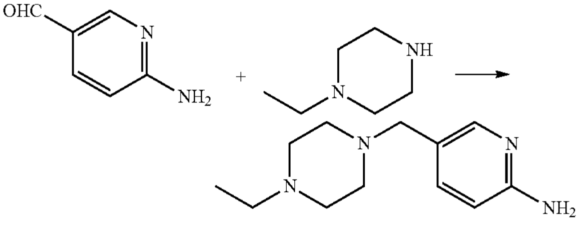

2-amino-5-formylpyridine (0.32 g, 2.6 mmol) and N-ethylpiperazine (0.45 g, 3.9 mmol) was dissolved in 1,2-dichloroethane (20 mL), stirred at room temperature for 2 h. Then sodium triacetylborohydride (0.87 g, 4.1 mmol) was added. The reaction was stirred at room temperature for 8 h. 1 M NaOH (30 mL) was added to quench. The mixture was extracted with DCM (20 mL×3), dried with anhydrous sodium sulfate, concentrated, and then subjected to column chromatography (DCM/MeOH=10:1) to obtain Compound 5-((4-ethylpiperazine-1-yl)methyl)pyridine-2-amine (0.52 g, 91%). $^1$HNMR (300 MHz, $CDCl_3$) δ 7.94 (d, J=2.3 Hz, 1H), 7.40 (dd, J=8.3, 2.4 Hz, 1H), 6.46 (d, J=8.3 Hz, 1H), 4.57 (s, 2H), 3.36 (s, 2H), 2.47-2.37 (m, 10H), 1.07 (t, J=7.2 Hz, 3H).

(8) The Synthesis of tert-butyl 4-((6-aminopyridine-3-yl)methyl)piperazine-1-carboxylate (B-3)

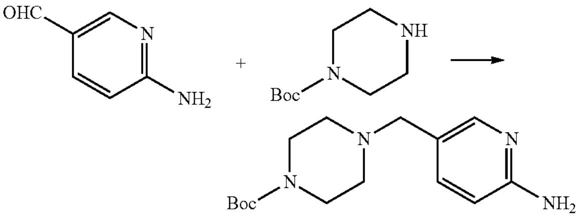

Referring to the synthesis of Compound (B-2), the yield was 89%. $^1$HNMR (300 MHz, $CDCl_3$): δ7.94 (d, J=2.3 Hz, 1H), 7.40 (dd, J=8.4, 2.3 Hz, 1H), 6.48 (d, J=8.4 Hz, 11H), 4.54 (s, 2H), 3.40 (t, J=5.1 Hz, 4H), 3.36 (s, 2H), 2.35 (t, J=5.1 Hz, 4H), 1.45 (s, 9H).

(9) The Synthesis of tert-butyl 4-(6-aminonicotinoyl)piperazine-1-carboxylate (B-4)

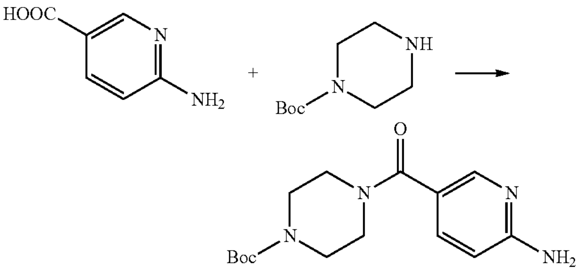

Referring to the synthesis of Compound (B-1), the yield was 87%. $^1H$ NMR (300 MHz, $CDCl_3$) δ 8.18 (d, J=2.2 Hz, 1H), 7.56 (dd, J=8.5, 2.2 Hz, 1H), 6.51 (d, J=8.5 Hz, 1H), 4.76 (s, 2H), 3.65-3.56 (m, 4H), 3.48-3.42 (m, 4H), 1.48 (s, 9H).

(10) The Synthesis of tert-butyl 4-(6-aminopyridine-3-yl)piperazine-1-carboxylate (B-5)

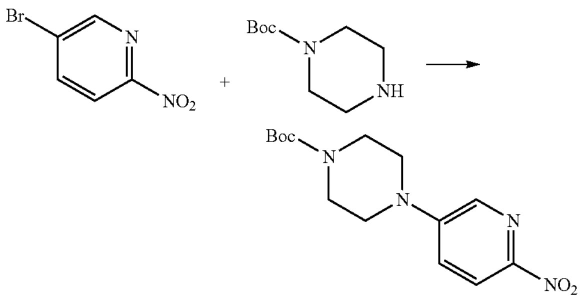

Step 1. The synthesis of tert-butyl 4-(6-nitropyridine-3-yl)piperazine-1-carboxylate: 5-bromo-2-nitropyridine (0.41 g, 2.0 mmol), tert-butylpiperazine-1-carboxylate (0.48 g, 2.6 mmol) and triethylamine (0.41 g, 4.0 mmol) were weighed and dissolved in DMSO(5 mL), heated to 60° C., and reacted for 18 h. The mixture was cooled, filtered and concentrated, and purified by flash silica gel column chromatography to obtain compound tert-butyl 4-(6-nitropyridine-3-yl)piperazine-1-carboxylate (0.49 g, 80% yield). $^1H$ NMR (400 MHz, $CDCl_3$) δ 8.17-8.13 (m, 2H), 7.22 (dd, J=9.2, 3.1 Hz, 1H), 3.66-3.64 (m, 4H), 3.49-3.46 (m, 4H), 1.49 (s, 9H).

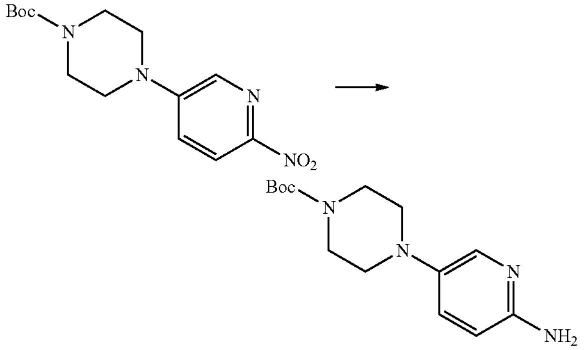

Step 2. The synthesis of tert-butyl 4-(6-aminopyridine-3-yl)piperazine-1-carboxylate: Tert-butyl 4-(6-nitropyridine-3-yl)piperazine-1-carboxylate (0.31 g, 1.0 mmol), reduced iron powder (0.17 g, 3.0 mmol) and ammonium chloride (0.49 g, 9.0 mmol) were weighed and dissolved in 70% ethanol (10 mL), heated to 70° C., and reacted for 6 h. The mixture was cooled, filtered and concentrated, and purified by flash silica gel column chromatography to obtain compound tert-butyl 4-(6-aminopyridine-3-yl)piperazine-1-carboxylate (0.24 g, 85% yield). $^1H$ NMR (300 MHz, $CDCl_3$) δ 7.78 (d, J=2.9 Hz, 1H), 7.17 (dd, J=8.8, 2.9 Hz, 1H), 6.49 (d, J=8.8 Hz, 1H), 4.19 (s, 2H), 3.59-3.55 (m, 4H), 2.98-2.94 (m, 4H), 1.48 (s, 9H).

(11) The Synthesis of 5-((4-(methanesulfonyl)piperazine-1-yl)methyl)pyridine-2-amine (B-6)

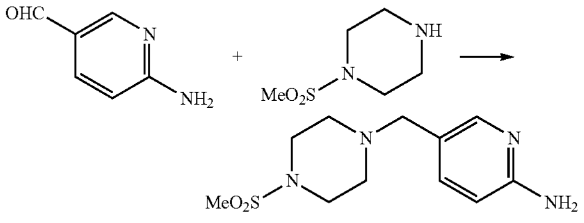

Referring to the synthesis of Compound (B-2), the yield was 90%. $^1H$ NMR (400 MHz, $CDCl_3$) δ 8.10-7.79 (m, 1H), 7.40 (d, J=8.3 Hz, 1H), 6.57 (s, 1H), 4.55 (s, 2H), 3.41 (s, 2H), 3.22 (t, J=4.9 Hz, 4H), 2.77 (s, 3H), 2.53 (t, J=5.0 Hz, 4H).

(12) The Synthesis of ethyl 4-((6-aminopyridine-3-yl)methyl)piperazine-1-carboxylate (B-7)

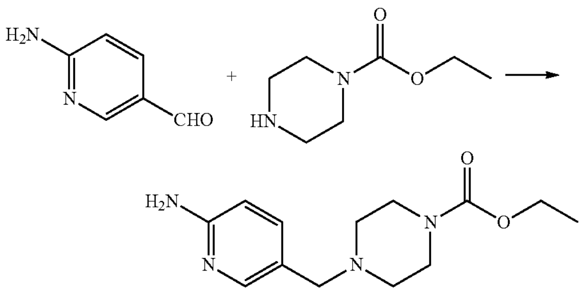

Referring to the synthesis of Compound (B-2), the yield was 86%. $^1H$ NMR (400 MHz, $CDCl_3$) δ 7.87 (d, J=2.2 Hz, 1H), 7.43 (dd, J=8.5, 2.3 Hz, 1H), 6.51 (d, J=8.5 Hz, 1H), 5.71 (s, 2H), 4.12 (q, J=7.1 Hz, 2H), 3.46 (t, J=5.1 Hz, 4H), 3.36 (s, 2H), 2.37 (t, J=5.1 Hz, 4H), 1.25 (t, J=7.1 Hz, 3H).

(13) The Synthesis of 5-((4-isopropylpiperazine-1-yl)methyl)pyridine-2-amine (B-8)

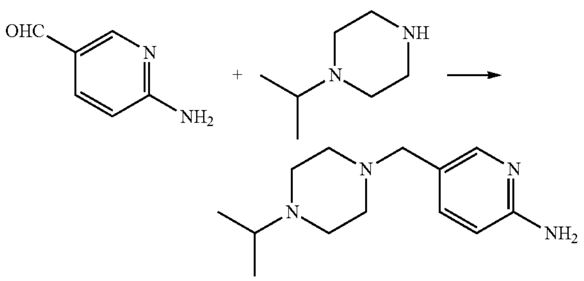

Referring to the synthesis of Compound (B-2), the yield was 81%. $^1H$ NMR (400 MHz, $CDCl_3$) δ 7.88 (d, J=2.2 Hz, 1H), 7.43 (dd, J=8.4, 2.2 Hz, 1H), 6.48 (d, J=8.4 Hz, 1H), 4.95 (s, 2H), 3.39 (s, 2H), 2.88-2.80 (m, 1H), 2.72-2.51 (m, 8H), 1.10 (d, J=6.6 Hz, 6H).

(14) The Synthesis of (6-aminopyridine-3-yl)(4-isopropylpiperazine-1-yl)ketone (B-9)

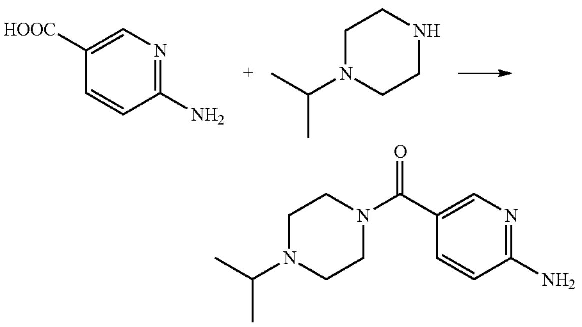

Referring to the synthesis of Compound (B-1), the yield was 85%. H NMR (300 MHz, $CDCl_3$) δ 8.18 (s, 1H), 7.55 (d, J=8.4 Hz, 1H), 6.49 (dd, J=8.6, 2.1 Hz, 1H), 4.86 (s, 2H), 3.67-3.61 (m, 4H), 2.77-2.71 (m, 1H), 2.55-2.51 (m, 4H), 1.05 (d, J=6.0 Hz, 6H).

II. The Synthesis of Compound I-1 to I-53

Example 1

The synthesis of (6-((4-(benzothiazole-6-yl)-5-fluoropyrimidine-2-yl)amino)pyridine-3-yl)(4-ethylpiperazine-1-yl) ketone (I-1):

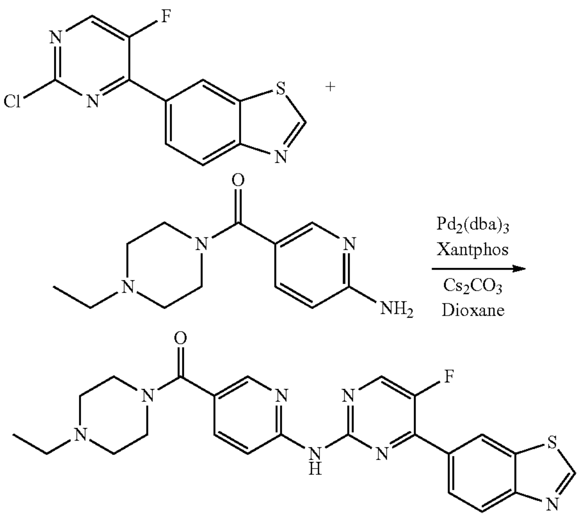

Compound 6-(2-chloro-5-fluoropyrimidine-4-yl)benzothiazole(133 mg, 0.5 mmol) and 6-aminopyridine-3-yl)(4-ethylpiperazine-1-yl)ketone(141 mg, 0.6 mmol) were dissolved in dioxane (5 mL). Then $Pd_2(dba)_3$ (23 mg, 0.025 mmol), Xantphos (58 mg, 0.1 mmol), cesium carbonate (326 mg, 1.0 mmol) were added. The reaction was replaced with argon three times, heated to 100° C., and reacted for 12 h. The mixture was cooled, filtered and concentrated, and subjected to column chromatography (DCM-DCM/MeOH=10:1) to obtain compound (6-((4-(benzothiazole-6-yl)-5-fluoropyrimidine-2-yl)amino)pyridine-3-yl)(4-ethylpiperazine-1-yl)ketone(88 mg, 38% yield). $^1H$ NMR (300 MHz, $CDCl_3$) δ 9.68 (s, 1H), 9.15 (s, 1H), 8.76-8.75 (m, 1H), 8.61-8.58 (m, 2H), 8.52 (dd, J=8.7, 0.9 Hz, 1H), 8.33-8.26 (m, 2H), 7.86 (dd, J=8.7, 2.3 Hz, 1H), 3.80-3.61 (m, 4H), 2.51-2.44 (m, 6H), 1.12 (t, J=7.2 Hz, 3H).

Example 2

The synthesis of 4-(benzothiazole-6-yl)-N-(5-((4-ethylpiperazine-1-yl)methyl)pyridine-2-yl)-5-fluoropyrimidine-2-amine (I-2):

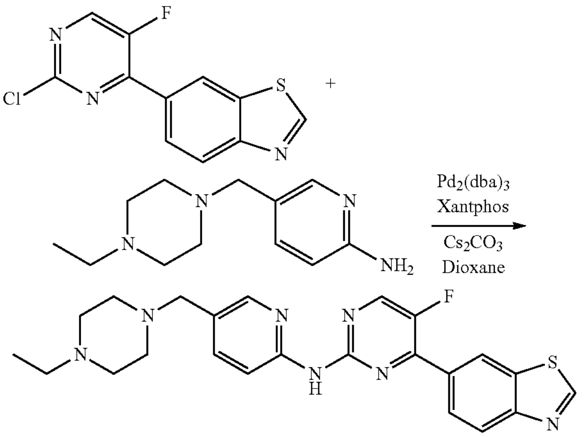

Referring to the synthesis of Compound (I-1), the yield was 43%. $^1H$ NMR (300 MHz, $CDCl_3$) δ 9.15 (s, 1H), 9.11 (s, 1H), 8.78-8.76 (m, 1H), 8.54 (d, J=3.5 Hz, 1H), 8.41 (d, J=8.6 Hz, 1H), 8.35-8.26 (m, 3H), 7.73 (dd, J=8.6, 2.3 Hz, 1H), 3.52 (s, 2H), 2.58-2.47 (m, 10H), 1.14 (t, J=7.2 Hz, 3H).

Example 3

The synthesis of tert-butyl 4-((6-((4-(benzothiazole-6-yl)-5-fluoropyrimidine-2-yl)amino)pyridine-3-yl)methyl)piperazine-1-carboxylate (1-3):

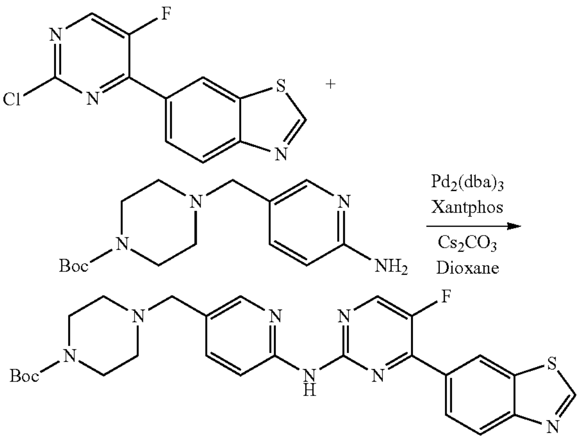

Referring to the synthesis of Compound (I-1), the yield was 52%. $^1H$ NMR (400 MHz, $CDCl_3$) δ 9.14 (s, 1H), 8.83 (s, 1H), 8.77 (d, J=1.5 Hz, 1H), 8.52 (d, J=3.5 Hz, 1H), 8.41 (d, J=8.6 Hz, 1H), 8.34-8.27 (m, 3H), 7.75-7.73 (m, 1H), 3.50 (s, 2H), 3.45-3.43 (m, J=5.2 Hz, 4H), 2.43-2.40 (m, 4H), 1.46 (s, 9H).

Example 4

The synthesis of 4-(benzothiazole-6-yl)-5-fluoro-N-(5-(piperazine-1-ylmethyl)pyridine-2-yl)pyrimidine-2-amine hydrochloride (I-4):

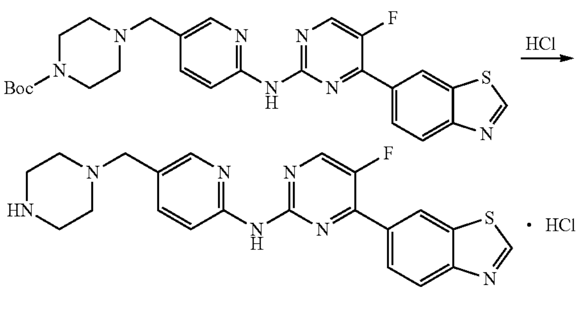

Tert-butyl 4-((6-((4-(benzothiazole-6-yl)-5-fluoropyrimidine-2-yl)amino)pyridine-3-yl)methyl)piperazine-1-carboxylate was dissolved in dichloromethane, and introduced with HCl gas under 0° C. condition and reacted for 2 h. After the reaction was completed, the mixture was concentrated to obtain Compound 4-(benzothiazole-6-yl)-5-fluoro-N-(5-(piperazine-1-ylmethyl)pyridine-2-yl)pyrimidine-2-amine hydrochloride, the yield was 100%.

$^1$H NMR (300 MHz, DMSO-$d_6$) δ 12.17 (s, 1H), 10.08 (s, 1H), 9.62 (s, 1H), 8.95 (t, J=2.7 Hz, 2H), 8.71 (s, 1H), 8.53 (d, J=8.8 Hz, 1H), 8.30 (q, J=8.7 Hz, 2H), 7.99 (d, J=9.0 Hz, 1H), 4.57 (s, 2H), 3.54-3.42 (m, 10H).

Example 5

The synthesis of tert-butyl 4-(6-((4-(benzothiazole-6-yl)-5-fluoropyrimidine-2-yl)amino)nicotinoyl)piperazine-1-carboxylate (I-5):

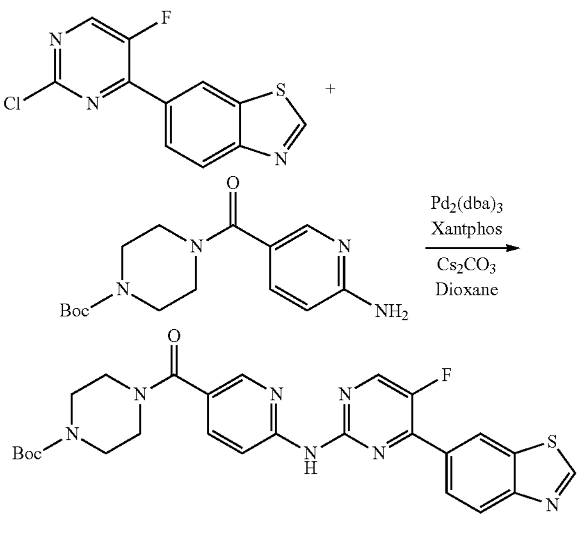

Referring to the synthesis of Compound (I-1), the yield was 52%. $^1$H NMR (400 MHz, $CDCl_3$) δ 9.16 (s, 11H), 8.78-8.78 (m, 11H), 8.52-8.49 (m, 2H), 8.44 (dd, J=2.4, 0.8 Hz, 11H), 8.34-8.28 (m, 3H), 7.84 (dd, J=8.7, 2.3 Hz, 1H), 3.70-3.44 (m, 8H), 1.48 (s, 9H).

Example 6

The synthesis of 6-((4-(benzothiazole-6-yl)-5-fluoropyrimidine-2-yl)amino)pyridine-3-yl)(piperazine-1-yl)ketone hydrochloride (I-6):

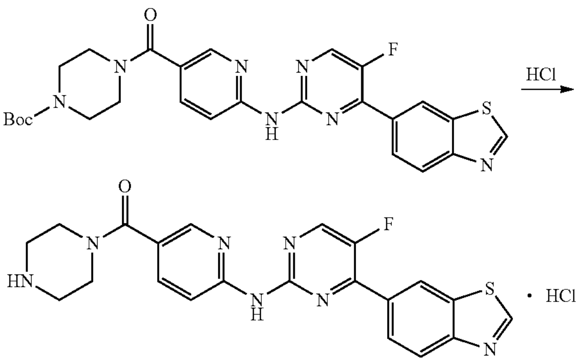

The preparation method of 6-((4-(benzothiazole-6-yl)-5-fluoropyrimidine-2-yl)amino)pyridine-3-yl)(piperazine-1-yl)ketone hydrochloride referred to the synthesis of Compound (1-4), and the yield was 100%.

$^1$H NMR (400 MHz, DMSO-$d_6$) δ 11.25 (s, 1H), 9.60-9.58 (m, 3H), 8.93 (d, J=1.6 Hz, 1H), 8.88 (d, J=3.3 Hz, 1H), 8.51 (d, J=2.2 Hz, 1H), 8.32-8.25 (m, 2H), 8.19-8.09 (m, 2H), 3.79-3.76 (m, 4H), 3.18-3.16 (m, 4H).

Example 7

The synthesis of tert-butyl 4-(6-((4-(benzothiazole-6-yl)-5-fluoropyrimidine-2-yl)amino)pyridine-3-yl)piperazine-1-carboxylate (I-7):

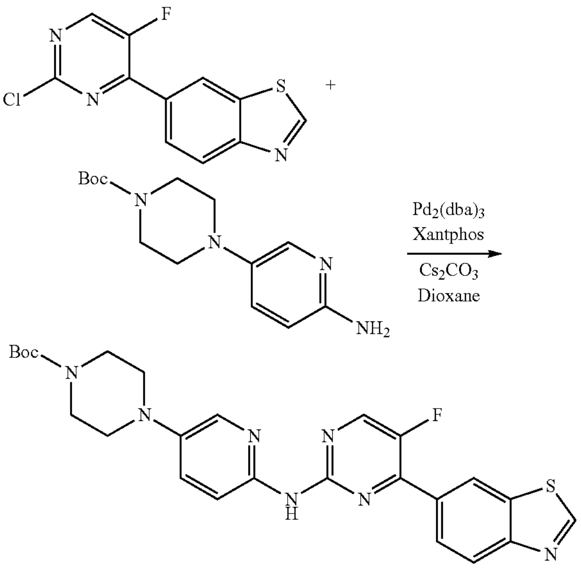

Referring to the synthesis of Compound (1-1), the yield was 47%. $^1$H NMR (400 MHz, $CDCl_3$) δ 9.15 (s, 1H), 8.77-8.76 (m, 1H), 8.45 (d, J=3.4 Hz, 1H), 8.33-8.26 (m, 3H), 8.04-8.02 (m, 2H), 7.38 (dd, J=9.1, 3.0 Hz, 1H), 3.63-3.60 (m, 4H), 3.11-3.09 (m, 4H), 1.49 (s, 9H).

Example 8

The synthesis of 4-(benzothiazole-6-yl)-5-fluoro-N-(5-(piperazine-1-yl)pyridine-2-yl)pyrimidine-2-amine hydrochloride (I-8):

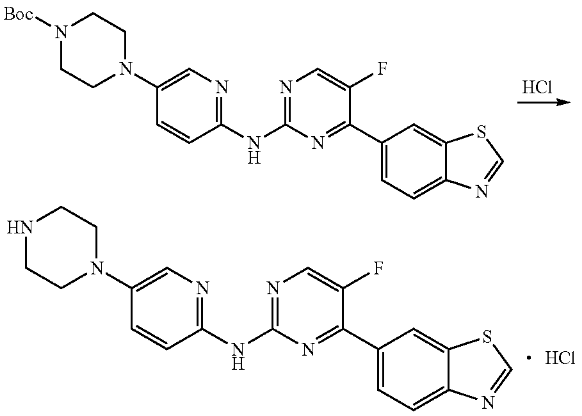

Referring to the synthesis of Compound (I-4), the yield was 100%. $^1$H NMR (400 MHz, DMSO-$d_6$) δ 11.43 (s, 1H), 9.60 (s, 1H), 9.33 (s, 2H), 8.91 (s, 1H), 8.87 (d, J=3.3 Hz, 1H), 8.33-8.23 (m, 2H), 8.07 (d, J=9.4 Hz, 1H), 8.01 (d, J=2.9 Hz, 1H), 7.85 (d, J=9.4 Hz, 1H), 3.44 (t, J=5.1 Hz, 4H), 3.27-3.25 (m, 4H).

Example 9

The synthesis of 4-(benzothiazole-6-yl)-5-fluoro-N-(5-((4-(methanesulfonyl)piperazine-1-yl)methyl)pyridine-2-yl)pyrimidine-2-amine (I-9):

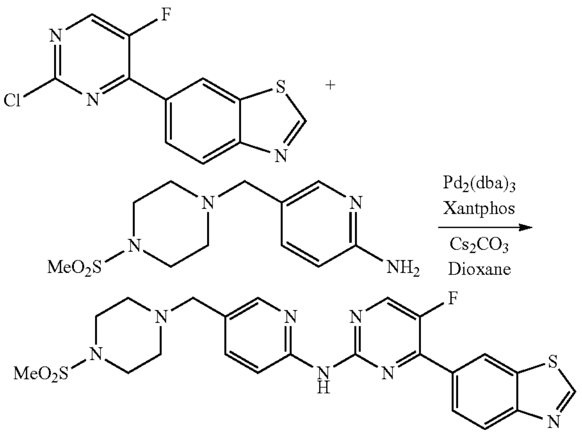

Referring to the synthesis of Compound (I-1), the yield was 45%. $^1$H NMR (400 MHz, $CDCl_3$) δ 9.15 (s, 1H), 8.78-8.77 (m, 1H), 8.48 (d, J=3.4 Hz, 1H), 8.40 (dd, J=8.5, 0.8 Hz, 1H), 8.34-8.29 (m, 2H), 8.25-8.25 (m, 1H), 8.18 (s, 1H), 7.70 (dd, J=8.6, 2.4 Hz, 1H), 3.53 (s, 2H), 3.25 (t, J=4.9 Hz, 4H), 2.78 (s, 3H), 2.58 (t, J=5.0 Hz, 4H).

Example 10

The synthesis of ethyl 4-((6-((4-(benzothiazole-6-yl)-5-fluoropyrimidine-2-yl)amino)pyridine-3-yl)methyl)piperazine-1-carboxylate (I-10):

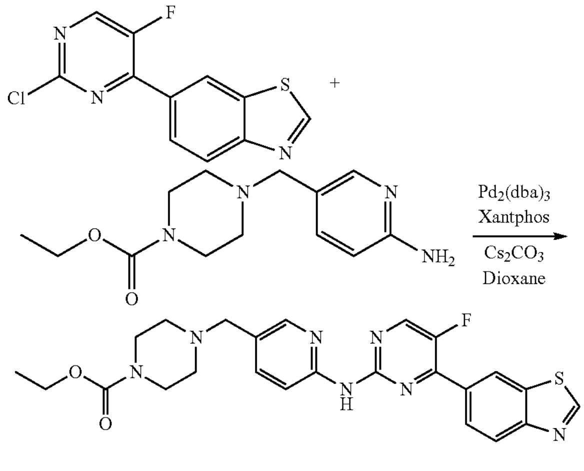

Referring to the synthesis of Compound (I-1), the yield was 55%. H NMR (400 MHz, $CDCl_3$) δ 9.15 (s, 1H), 8.78-8.77 (m, 1H), 8.48 (d, J=3.4 Hz, 1H), 8.39 (dd, J=8.6, 0.8 Hz, 1H), 8.34-8.27 (m, 2H), 8.25-8.24 (m, 2H), 7.72 (dd, J=8.6, 2.3 Hz, 1H), 4.13 (q, J=7.1 Hz, 2H), 3.50-3.47 (m, 6H), 2.42 (t, J=5.0 Hz, 4H), 1.26 (t, J=7.1 Hz, 3H).

Example 11

The synthesis of 4-(benzothiazole-6-yl)-5-fluoro-N-(5-((4-isopropylpiperazine-1-yl)methyl)pyridine-2-yl)pyrimidine-2-amine (I-11):

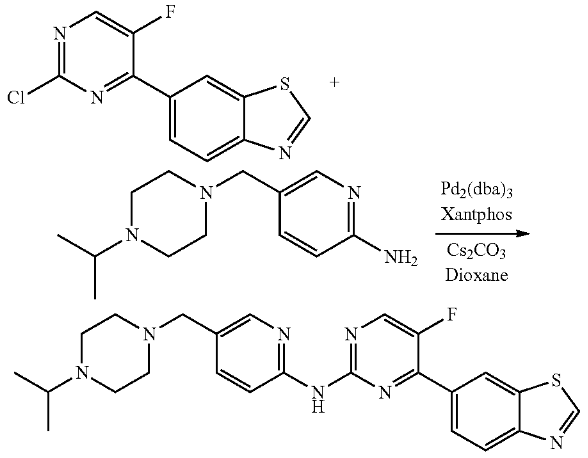

Referring to the synthesis of Compound (I-1), the yield was 48%. $^1$H NMR (400 MHz, $CDCl_3$) δ 9.15 (s, 1H), 8.78 (d, J=1.6 Hz, 1H), 8.48 (d, J=3.5 Hz, 1H), 8.38 (dd, J=8.5, 0.8 Hz, 1H), 8.35-8.32 (m, 1H), 8.30-8.27 (m, 1H), 8.25-8.23 (m, 2H), 7.73 (dd, J=8.6, 2.3 Hz, 1H), 3.50 (s, 2H), 2.68-2.44 (m, 9H), 1.06 (d, J=6.5 Hz, 6H).

Example 12

The synthesis of (4-ethylpiperazine-1-yl)(6-((5-fluoro-4-(2-methylbenzothiazole-6-yl)pyrimidine-2-yl)amino)pyridine-3-yl)ketone (I-12):

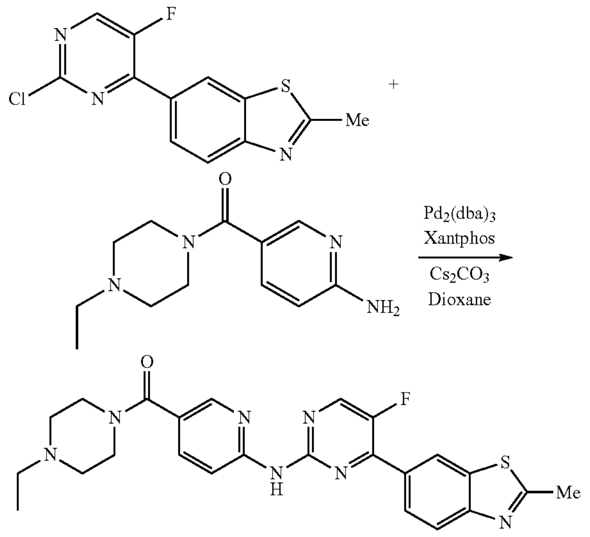

Referring to the synthesis of Compound (I-1), the yield was 40%. (H NMR (400 MHz, $CDCl_3$) δ 9.25 (s, 1H), 8.63 (d, J=1.8 Hz, 1H), 8.56-8.54 (m, 2H), 8.51 (d, J=8.7 Hz, 1H), 8.24 (dt, J=8.7, 1.3 Hz, 1H), 8.09 (d, J=8.6 Hz, 1H), 7.86 (dd, J=8.7, 2.4 Hz, 1H), 3.78-3.64 (m, 4H), 2.90 (s, 3H), 2.51-2.46 (m, 6H), 1.13 (t, J=7.1 Hz, 3H).

Example 13

The synthesis of N-(5-((4-ethylpiperazine-1-yl)methyl) pyridine-2-yl)-5-fluoro-4-(2-methylbenzothiazole-6-yl)pyrimidine-2-amine (1-13):

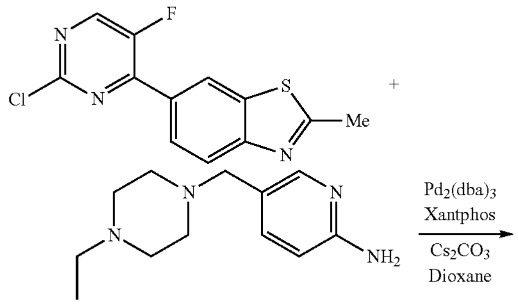

-continued

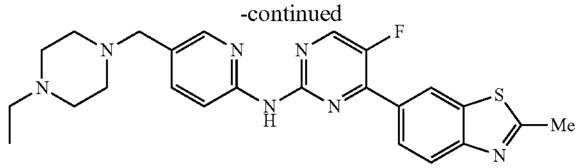

Referring to the synthesis of Compound (I-1), the yield was 52%. $^{1}$H NMR (300 MHz, $CDCl_3$) δ 8.63 (d, J=1.8 Hz, 1H), 8.49-8.47 (m, 2H), 8.38 (d, J=8.6 Hz, 1H), 8.28-8.24 (m, 2H), 8.08 (d, J=8.7 Hz, 1H), 7.72 (dd, J=8.6, 2.3 Hz, 1H), 3.51 (s, 2H), 2.90 (s, 3H), 2.55-2.45 (m, 10H), 1.11 (t, J=7.2 Hz, 3H).

Example 14

The synthesis of tert-butyl 4-((6-((5-fluoro-4-(2-methylbenzothiazole-6-yl)pyrimidine-2-yl)amino)pyridine-3-yl) methyl)piperazine-1-carboxylate (I-14):

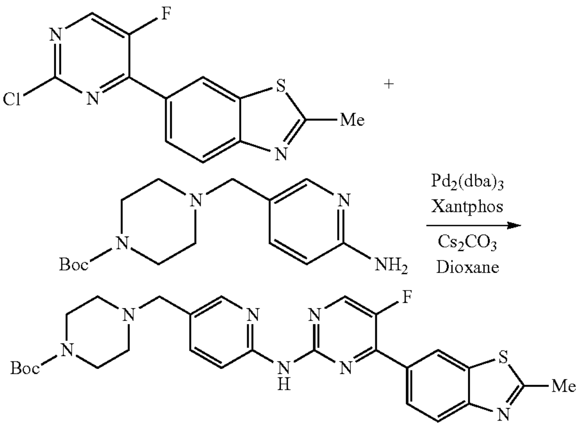

Referring to the synthesis of Compound (1-1), the yield was 55%. $^{1}$H NMR (300 MHz, $CDCl_3$) δ 8.63 (s, 11H), 8.46 (d, J=3.5 Hz, 11H), 8.39 (d, J=8.6 Hz, 11H), 8.32 (s, 1H), 8.27-8.24 (m, 2H), 8.08 (d, J=8.7 Hz, 1H), 7.72 (d, J=8.4 Hz, 1H), 3.49 (s, 2H), 3.43 (t, J=4.8 Hz, 4H), 2.91 (s, 3H), 2.42-2.39 (m, 4H), 1.46 (s, 9H).

Example 15

The synthesis of 5-fluoro-4-(2-methylbenzothiazole-6-yl)-N-(5-(piperazine-1-ylmethyl)pyridine-2-yl)pyrimidine-2-amine hydrochloride (1-15):

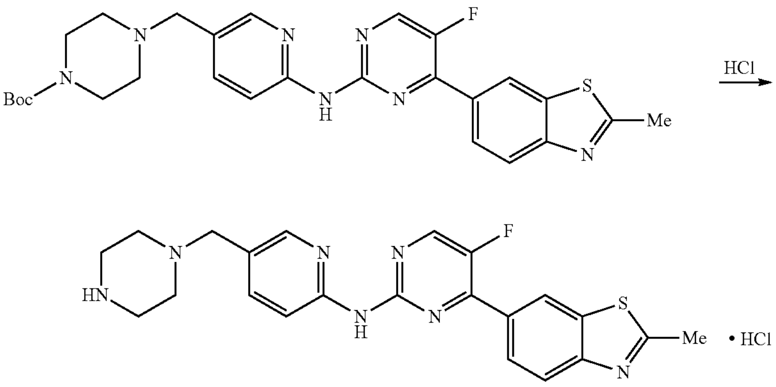

Referring to the synthesis of Compound (1-4), the yield was 100%. H NMR (400 MHz, DMSO-$d_6$) δ 11.67 (s, 1H), 9.90 (s, 2H), 8.89 (d, J=3.3 Hz, 1H), 8.80 (d, J=1.7 Hz, 1H), 8.64 (d, J=2.2 Hz, 1H), 8.40 (dd, J=9.0, 2.2 Hz, 1H), 8.21 (dt, J=8.6, 1.3 Hz, 1H), 8.13 (d, J=8.6 Hz, 11H), 8.04 (d, J=8.9 Hz, 1H), 4.50 (s, 2H), 3.50-3.45 (m, 8H), 2.88 (s, 3H).

Example 16

The synthesis of tert-butyl 4-(6-((5-fluoro-4-(2-methylbenzothiazole-6-yl)pyrimidine-2-yl)amino)nicotinoyl)piperazine-1-carboxylate (I-16):

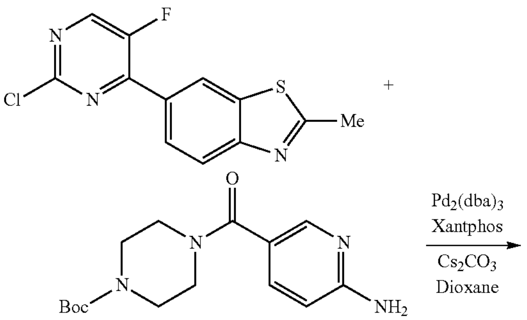

-continued

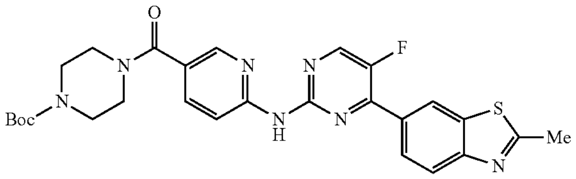

Referring to the synthesis of Compound (I-1), the yield was 40%. $^1$H NMR (400 MHz, $CDCl_3$) δ 9.11 (s, 1H), 8.63 (s, 1H), 8.55-8.51 (m, 3H), 8.24 (d, J=8.6 Hz, 1H), 8.09 (dd, J=8.7, 3.3 Hz, 1H), 7.86 (dt, J=8.9, 2.6 Hz, 1H), 3.67-3.46 (m, 8H), 2.91 (s, 3H), 1.48 (s, 9H).

Example 17

The synthesis of (6-((5-fluoro-4-(2-methylbenzothiazole-6-yl)pyrimidine-2-yl)amino)pyridine-3-yl)(piperazine-1-yl) ketone hydrochloride (I-17):

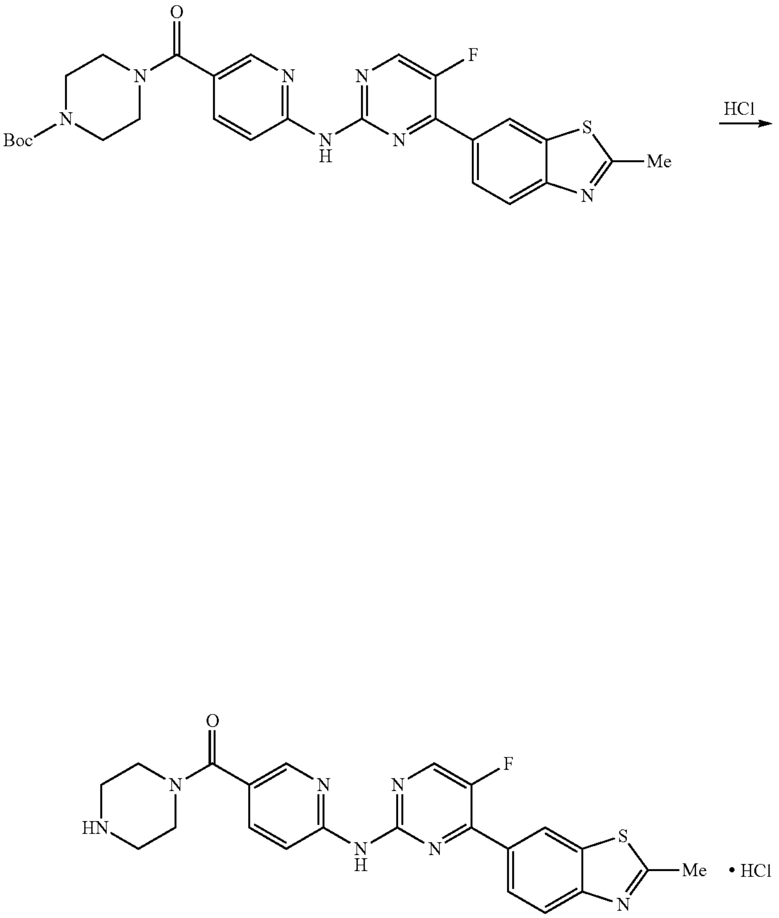

Referring to the synthesis of Compound (I-4), the yield was 100%. H NMR (300 MHz, DMSO-$d_6$) δ 12.04 (s, 1H), 9.85 (s, 2H), 8.92 (d, J=2.9 Hz, 1H), 8.81 (s, 1H), 8.60 (s, 1H), 8.28 (d, J=9.1 Hz, 1H), 8.21 (d, J=8.7 Hz, 1H), 8.13 (d, J=8.6 Hz, 1H), 8.06 (d, J=9.0 Hz, 1H), 3.83-3.77 (m, 4H), 3.20-3.14 (m, 4H), 2.88 (s, 3H).

Example 18

The synthesis of (6-((4-(2-(cyclopentylamino)benzothiazole-6-yl)-5-fluoropyrimidine-2-yl)amino)pyridine-3-yl)(4-ethylpiperazine-1-yl)ketone (1-18):

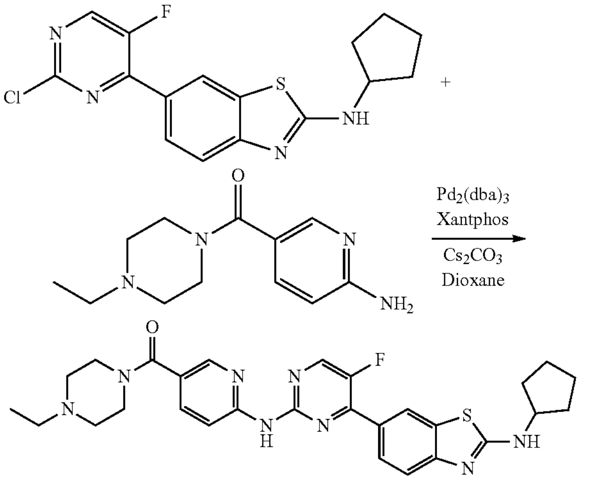

Referring to the synthesis of Compound (I-1), the yield was 45%. $^1$H NMR (400 MHz, $CDCl_3$) δ 8.90 (s, 1H), 8.50 (d, J=8.7 Hz, 1H), 8.46 (d, J=2.2 Hz, 1H), 8.43 (d, J=3.6 Hz, 1H), 8.40 (d, J=1.8 Hz, 1H), 8.07 (dd, J=8.7, 1.8 Hz, 1H), 7.84 (dd, J=8.7, 2.3 Hz, 1H), 7.64 (d, J=8.5 Hz, 1H), 6.08 (s, 1H), 3.80-3.65 (m, 4H), 2.52-2.47 (m, 6H), 2.18-2.12 (m, 2H), 1.81-1.64 (m, 6H), 1.13 (t, J=7.2 Hz, 3H).

Example 19

The synthesis of N-cyclopentyl-6-(2-((5-((4-ethylpiperazine-1-yl)methyl)pyridine-2-yl)amino)-5-fluoropyrimidine-4-yl)benzothiazole-2-amine (I-19):

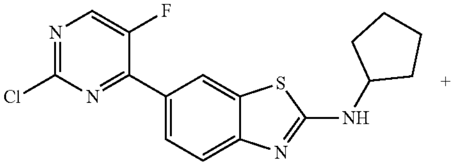

-continued

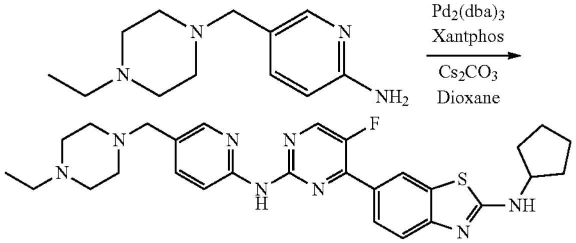

Referring to the synthesis of Compound (I-1), the yield was 51%. $^1$H NMR (400 MHz, $CDCl_3$) δ 8.59 (s, 1H), 8.43-8.35 (m, 3H), 8.23 (d, J=2.2 Hz, 1H), 8.08-8.05 (m, 1H), 7.71 (dd, J=8.6, 2.3 Hz, 1H), 7.64 (d, J=8.6 Hz, 1H), 6.12 (d, J=6.7 Hz, 1H), 4.08-4.04 (m, 1H), 3.50 (s, 2H), 2.54-2.42 (m, 10H), 2.19-2.11 (m, 2H), 1.79-1.64 (m, 6H), 1.10 (t, J=7.2 Hz, 311).

Example 20

The synthesis of tert-butyl 4-((6-((4-(2-(cyclopentylamino)benzothiazole-6-yl)-5-fluoropyrimidine-2-yl)amino)pyridine-3-yl)methyl)piperazine-1-carboxylate (I-20):

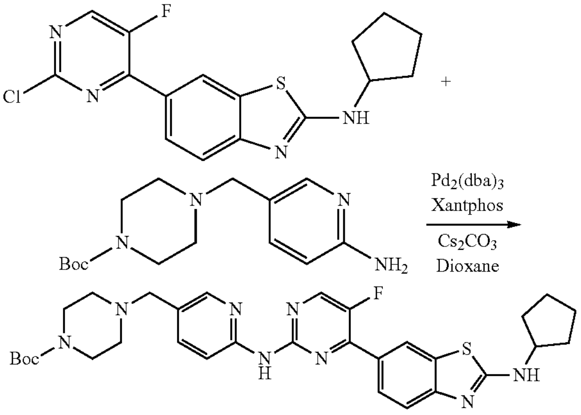

Referring to the synthesis of Compound (I-1), the yield was 57%. $^1$H NMR (400 MHz, $CDCl_3$) δ 8.43-8.40 (m, 2H), 8.38 (d, J=3.7 Hz, 1H), 8.22 (s, 2H), 8.11 (d, J=7.8 Hz, 1H), 7.79 (s, 1H), 7.63 (d, J=8.4 Hz, 1H), 5.71 (s, 1H), 4.13-4.05 (m, 1H), 3.60-3.45 (m, 6H), 2.57-2.43 (m, 4H), 2.20-2.12 (m, 2H), 1.80-1.61 (m, 6H), 1.46 (s, 9H).

Example 21

The synthesis of N-cyclopentyl-6-(5-fluoro-2-((5-(piperazine-1-ylmethyl)pyridine-2-yl)amino)pyrimidine-4-yl)benzothiazole-2-amine hydrochloride (I-21):

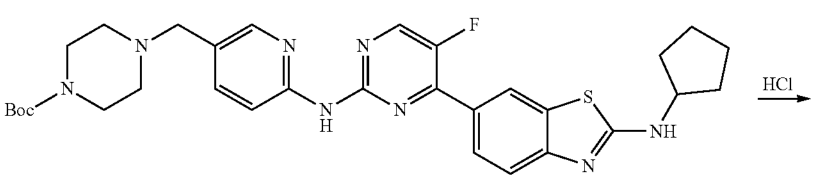

-continued

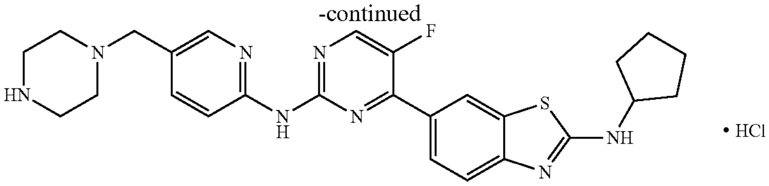

Referring to the synthesis of Compound (1-4), the yield was 100%. $^{1}$H NMR (400 MHz, DMSO-$d_6$) δ 11.31 (s, 1H), 9.80 (s, 2H), 9.40 (s, 1H), 8.79 (d, J=3.6 Hz, 1H), 8.60 (d, J=2.2 Hz, 1H), 8.53 (d, J=1.8 Hz, 1H), 8.32 (dd, J=9.1, 2.2 Hz, 1H), 8.10-8.06 (m, 2H), 7.65 (d, J=8.6 Hz, 1H), 4.44 (s, 2H), 4.29-4.24 (m, 1H), 3.46-3.38 (m, 8H), 3.17 (s, 1H), 2.06-1.99 (m, 2H), 1.73-1.59 (m, 6H).

Example 22

The synthesis of tert-butyl 4-(6-((4-(2-(cyclopentylamino)benzothiazole-6-yl)-5-fluoropyrimidine-2-yl)amino)nicotinoyl)piperazine-1-carboxylate (I-22):

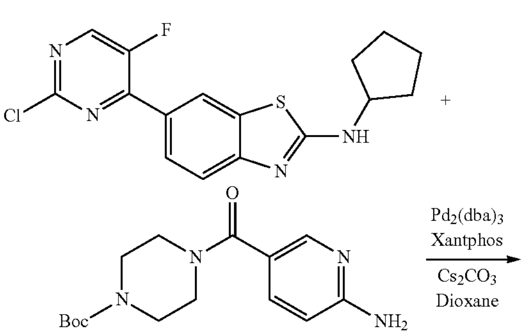

-continued

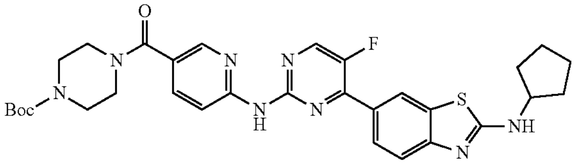

Referring to the synthesis of Compound (I-1), the yield was 53%. $^{1}$H NMR (400 MHz, $CDCl_3$) δ 8.82 (s, 1H), 8.51 (d, J=8.4 Hz, 1H), 8.46-8.41 (m, 3H), 8.09 (d, J=8.3 Hz, 1H), 7.85-7.82 (m, 1H), 7.63 (d, J=8.3 Hz, 1H), 6.20 (s, 1H), 4.09-4.03 (m, 1H), 3.68-3.45 (m, 8H), 2.18-2.12 (m, 2H), 1.80-1.62 (m, 6H), 1.48 (s, 9H).

Example 23

The synthesis of (6-((4-(2-(cyclopentylamino)benzothiazole-6-yl)-5-fluoropyrimidine-2-yl)amino)pyridine-3-yl)(piperazine-1-yl)ketone hydrochloride (I-23):

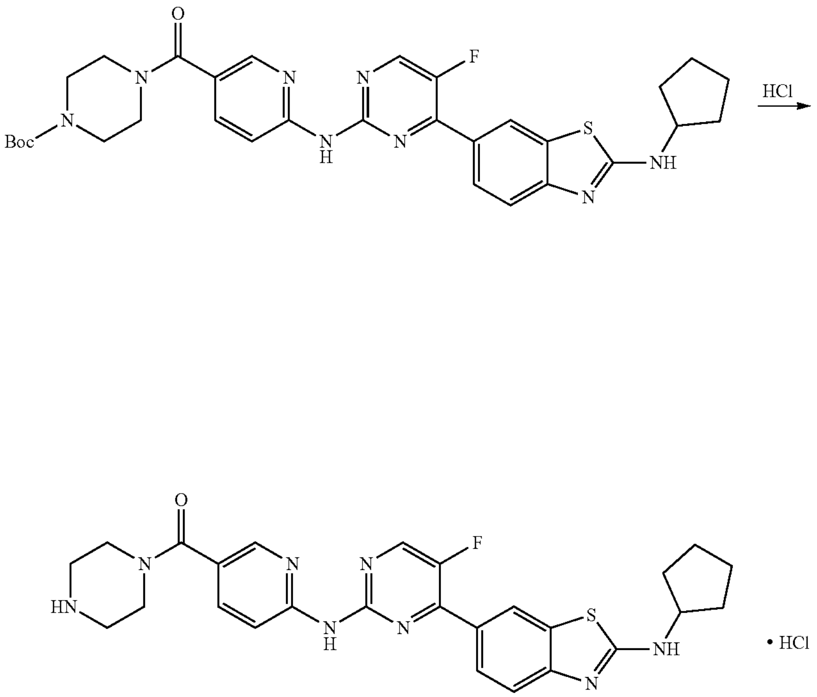

Referring to the synthesis of Compound (I-4), the yield was 100%. $^1$H NMR (400 MHz, DMSO-$d_6$) δ 11.15 (s, 1H), 9.70 (s, 1H), 9.52 (s, 2H), 8.80 (s, 1H), 8.56-8.50 (m, 2H), 8.15-8.09 (m, 3H), 7.69 (d, J=8.6 Hz, 1H), 4.32-4.25 (m, 1H), 3.80-3.74 (m, 4H), 3.33 (s, 1H), 3.20-3.14 (m, 4H), 2.05-1.99 (m, 2H), 1.76-1.59 (m, 6H).

Example 24

The synthesis of ethyl 4-((6-((4-(2-(cyclopentylamino) benzothiazole-6-yl)-5-fluoropyrimidine-2-yl)amino)pyridine-3-yl)methyl)piperazine-1-carboxylate (I-24):

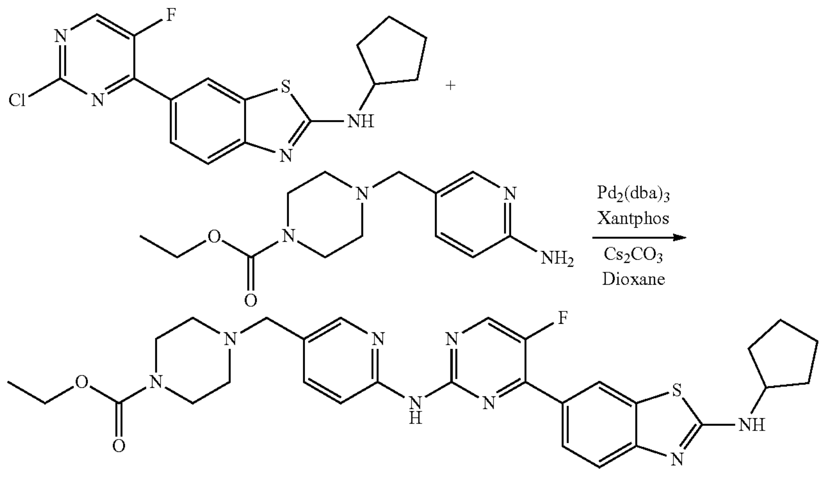

Referring to the synthesis of Compound (I-1), the yield was 56%. $^1$H NMR (400 MHz, $CDCl_3$) δ 8.82 (s, 1H), 8.42-8.38 (m, 3H), 8.25-8.24 (m, 1H), 8.05 (d, J=8.3 Hz, 1H), 7.73 (d, J=8.4 Hz, 1H), 7.64 (d, J=8.3 Hz, 1H), 6.25 (s, 1H), 4.14 (q, J=7.0 Hz, 2H), 4.08-4.02 (m, 1H), 3.54-3.47 (m, 6H), 2.46-2.42 (m, 4H), 2.19-2.11 (m, 2H), 1.79-1.61 (m, 6H), 1.26 (t, J=7.0 Hz, 3H).

Example 25

The synthesis of N-cyclopentyl-6-(5-fluoro-2-((5-((4-(methanesulfonyl)piperazine-1-yl)methyl)pyridine-2-yl) amino)pyrimidine-4-yl)benzothiazole-2-amine (I-25):

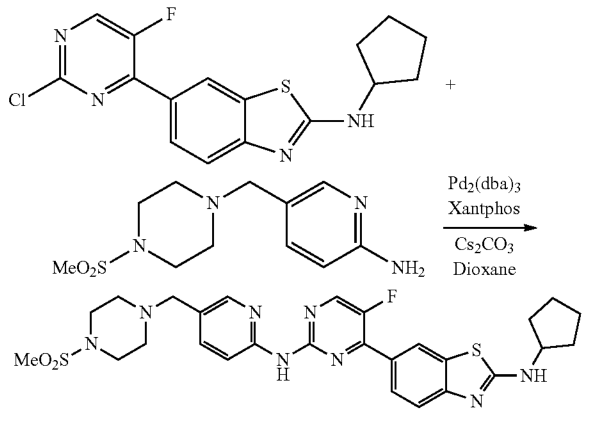

Referring to the synthesis of Compound (I-1), the yield was 53%. $^1$H NMR (400 MHz, $CDCl_3$) δ 8.54 (s, 1H), 8.42-8.39 (m, 3H), 8.24 (d, J=2.3 Hz, 1H), 8.10-8.07 (m, 1H), 7.69 (dd, J=8.6, 2.3 Hz, 1H), 7.64 (d, J=8.6 Hz, 1H), 5.96 (d, J=6.8 Hz, 1H), 4.09-4.04 (m, 1H), 3.52 (s, 2H), 3.25 (t, J=4.9 Hz, 4H), 2.79 (s, 3H), 2.58 (t, J=4.9 Hz, 4H), 2.19-2.11 (m, 2H), 1.80-1.70 (m, 6H).

Example 26

The synthesis of tert-butyl 4-(6-((4-(2-(cyclopentylamino)benzothiazole-6-yl)-5-fluoropyrimidine-2-yl) amino)pyridine-3-yl)piperazine-1-carboxylate (I-26):

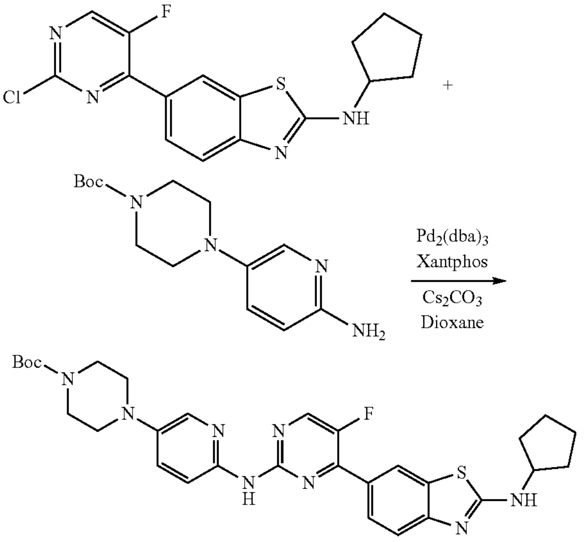

Referring to the synthesis of Compound (I-1), the yield was 44%. $^1$H NMR (400 MHz, $CDCl_3$) δ8.48 (s, 1H), 8.39 (d, J=1.8 Hz, 1H), 8.36 (d, J=3.7 Hz, 1H), 8.31 (d, J=9.1 Hz, 1H), 8.08-8.05 (m, 1H), 8.03 (d, J=2.9 Hz, 1H), 7.63 (d, J=8.5 Hz, 1H), 7.37 (dd, J=9.1, 3.0 Hz, 1H), 6.10 (d, J=6.6 Hz, 1H), 4.08-4.03 (m, 1H), 3.61 (t, J=5.1 Hz, 4H), 3.09 (t, J=5.0 Hz, 4H), 2.17-2.11 (m, 2H), 1.77-1.64 (m, 6H), 1.49 (s, 9H).

Example 27

The synthesis of N-cyclopentyl-6-(5-fluoro-2-((5-(piperazine-1-yl)pyridine-2-yl)amino)pyrimidine-4-yl)benzothiazole-2-amine hydrochloride (I-27):

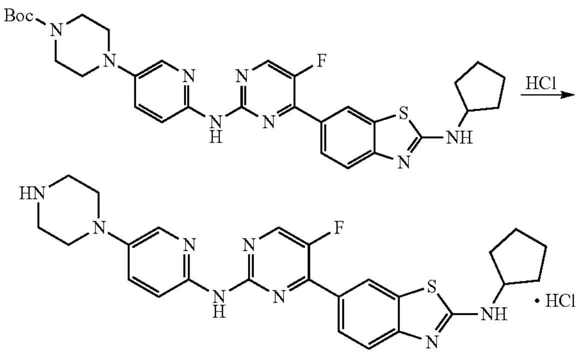

Referring to the synthesis of Compound (I-4), the yield was 100%. $^1$H NMR (400 MHz, DMSO-$d_6$) δ 11.97 (s, 11H), 10.53 (s, 1H), 9.86 (s, 2H), 8.83 (d, J=3.3 Hz, 11H), 8.57 (d, J=1.7 Hz, 1H), 8.27 (dd, J=9.6, 2.6 Hz, 1H), 8.11-8.09 (m, 1H), 8.05 (d, J=2.6 Hz, 1H), 7.86 (d, J=9.5 Hz, 1H), 7.77 (d, J=8.6 Hz, 1H), 4.41-4.35 (m, 1H), 3.52-3.50 (m, 4H), 3.26-3.23 (m, 4H), 2.08-2.02 (m, 2H), 1.76-1.60 (m, 6H).

Example 28

The synthesis of N-cyclopentyl-6-(5-fluoro-2-((5-((4-isopropylpiperazine-1-yl)methyl)pyridine-2-yl)amino)pyrimidine-4-yl)benzothiazole-2-amine (1-28):

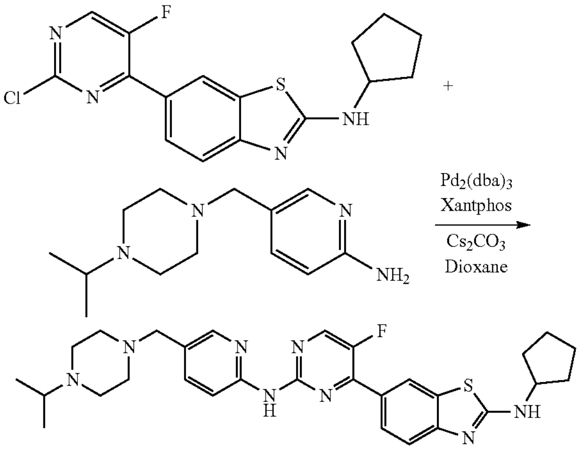

Referring to the synthesis of Compound (I-1), the yield was 50%. $^1$H NMR (400 MHz, $CDCl_3$) δ8.78 (s, 1H), 8.40-8.38 (m, 3H), 8.23 (d, J=2.2 Hz, 1H), 8.05 (dd, J=8.5, 1.8 Hz, 1H), 7.71 (dd, J=8.6, 2.3 Hz, 1H), 7.65 (d, J=8.6 Hz, 1H), 6.32 (d, J=6.2 Hz, 1H), 4.07-4.02 (m, 1H), 3.49 (s, 2H), 2.70-2.55 (m, 9H), 2.18-2.11 (m, 2H), 1.80-1.64 (m, 6H), 1.06 (d, J=6.5 Hz, 6H).

Example 29

The synthesis of (6-((4-(2-(cyclopentylamino)benzothiazole-6-yl)-5-fluoropyrimidine-2-yl)amino)pyridine-3-yl)(4-isopropylpiperazine-1-yl)ketone (1-29):

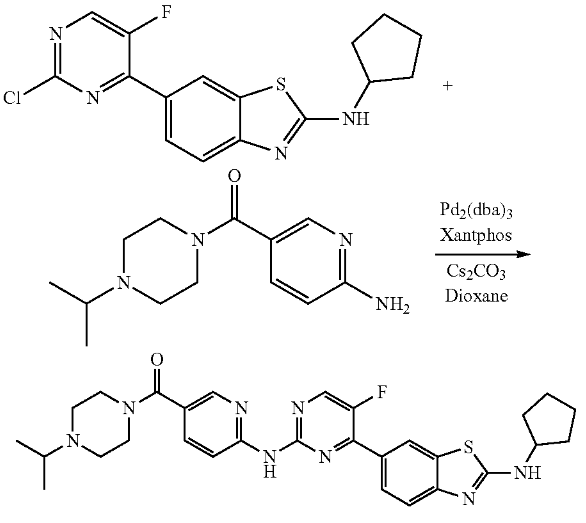

Referring to the synthesis of Compound (I-1), the yield was 48%. $^1$H NMR (400 MHz, $CDCl_3$) δ 9.04 (s, 1H), 8.52-8.39 (m, 4H), 8.05 (dd, J=8.4, 1.9 Hz, 1H), 7.85 (dt, J=8.6, 2.2 Hz, 1H), 7.64 (dd, J=8.6, 1.8 Hz, 1H), 6.19 (s, 1H), 4.09-4.04 (m, 1H), 3.73-3.62 (m, 4H), 2.79-2.75 (m, 1H), 2.60-2.55 (m, 4H), 2.18-2.13 (m, 2H), 1.78-1.64 (m, 6H), 1.08 (d, J=6.6 Hz, 6H).

Example 30

The synthesis of 6-(2-((5-((4-ethylpiperazine-1-yl)methyl)pyridine-2-yl)amino)-5-fluoropyrimidine-4-yl)-N,N-dimethylbenzothiazole-2-amine (I-30):

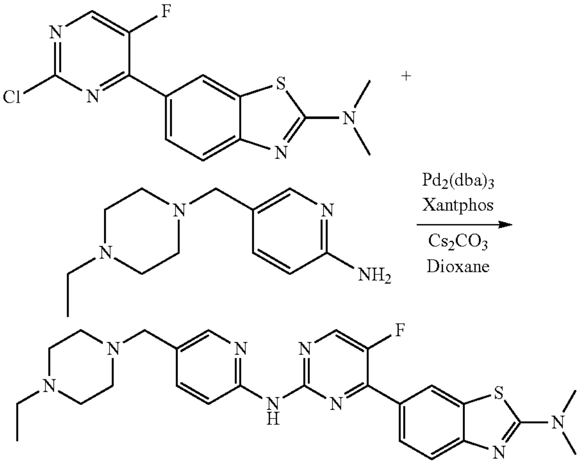

Referring to the synthesis of Compound (I-1), the yield was 42%. $^1$H NMR (400 MHz, $CDCl_3$) δ 8.45 (d, J=1.8 Hz, 1H), 8.38-8.36 (m, 2H), 8.21 (d, J=2.3 Hz, 1H), 8.15 (dt, J=8.7, 1.2 Hz, 1H), 7.94 (s, 1H), 7.71 (dd, J=8.6, 2.3 Hz, 1H), 7.65 (d, J=8.6 Hz, 1H), 3.49 (s, 2H), 3.27 (s, 6H), 2.60-2.36 (m, 10H), 1.09 (t, J=7.2 Hz, 3H).

Example 31

The synthesis of (6-((4-(2-(dimethylamino)benzothiazole-6-yl)-5-fluoropyrimidine-2-yl)amino)pyridine-3-yl)(4-ethylpiperazine-1-yl)ketone (I-31):

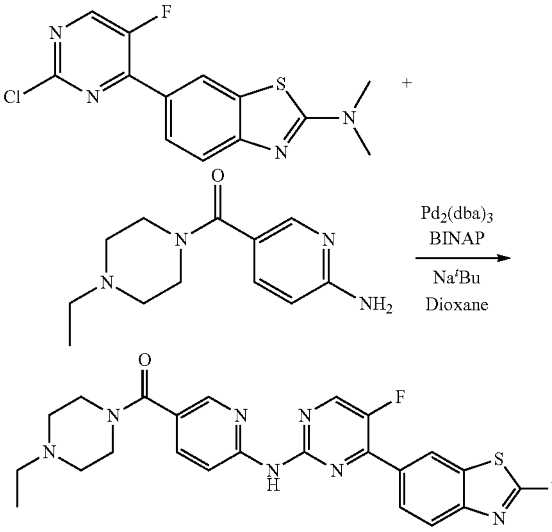

Molecular Weight: 506.6044

6-(2-chloro-5-fluoropyrimidine-4-yl)-N,N-dimethylbenzothiazole-2-amine(154 mg, 0.5 mmol) and 6-aminopyridine-3-yl)(4-ethylpiperazine-1-yl)ketone(141 mg, 0.6 mmol) was dissolved in dioxane (5 mL). Then $Pd_2(dba)_3$ (23 mg, 0.025 mmol), BINAP (31 mg, 0.05 mmol), sodium tert-butoxide (96 mg, 1.0 mmol) were added. The reaction was replaced with argon three times, heated to 100° C., and reacted for 12 h. The mixture was cooled, filtered and concentrated, and subjected to column chromatography (DCM-DCM/MeOH=10:1) to obtain compound (6-((4-(2-(dimethylamino)benzothiazole-6-yl)-5-fluoropyrimidine-2-yl)amino)pyridine-3-yl)(4-ethylpiperazine-1-yl)ketone (139 mg, 55% yield). $^1H$ NMR (400 MHz, DMSO-$d_6$) δ 10.27 (s, 1H), 8.69 (d, J=3.8 Hz, 1H), 8.52 (d, J=2.0 Hz, 1H), 8.35 (d, J=2.4 Hz, 1H), 8.31 (d, J=8.7 Hz, 1H), 8.06 (d, J=8.6 Hz, 1H), 7.86 (dd, J=8.6, 2.4 Hz, 1H), 7.59 (d, J=8.6 Hz, 1H), 3.59-3.47 (m, 4H), 3.21 (s, 6H), 2.44-2.34 (m, 6H), 1.01 (t, J=7.1 Hz, 3H).

Example 32

The synthesis of tert-butyl 4-((6-((4-(2-(dimethylamino)benzothiazole-6-yl)-5-fluoropyrimidine-2-yl)amino)pyridine-3-yl)methyl)piperazine-1-carboxylate (1-32):

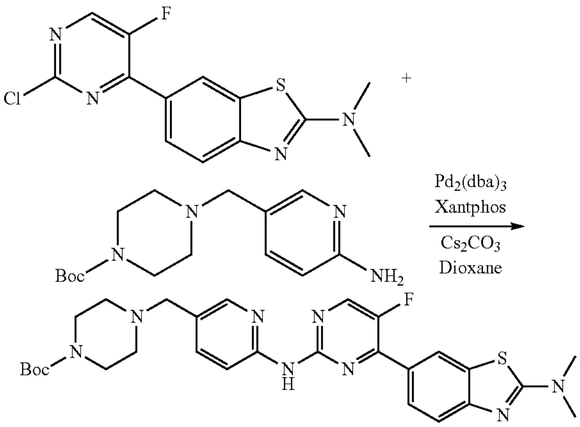

Referring to the synthesis of Compound (I-1), the yield was 48%. $^1H$ NMR (400 MHz, $CDCl_3$) δ 8.45 (d, J=1.8 Hz, 1H), 8.40-8.36 (m, 2H), 8.20 (d, J=2.2 Hz, 1H), 8.15 (dt, J=8.8, 1.2 Hz, 1H), 7.94 (s, 1H), 7.71 (dd, J=8.6, 2.3 Hz, 1H), 7.65 (d, J=8.6 Hz, 1H), 3.48 (s, 2H), 3.45-3.42 (m, 4H), 3.27 (s, 6H), 2.41-2.39 (m, 4H), 1.46 (s, 9H).

Example 33

The synthesis of 6-(5-fluoro-2-((5-(piperazine-1-ylmethyl)pyridine-2-yl)amino)pyrimidine-4-yl)-N,N-dimethylbenzothiazole-2-amine hydrochloride (I-33):

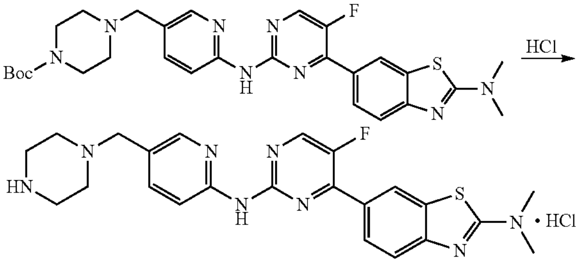

Referring to the synthesis of Compound (1-4), the yield was 100%. $^1H$ NMR (300 MHz, DMSO-$d_6$) δ 11.44 (s, 1H), 9.83 (s, 2H), 8.79 (d, J=2.9 Hz, 1H), 8.59 (d, J=11.9 Hz, 2H), 8.35 (d, J=8.9 Hz, 1H), 8.07 (dd, J=14.1, 8.8 Hz, 2H), 7.65 (d, J=8.6 Hz, 1H), 4.46 (s, 2H), 3.49-3.41 (m, 8H), 3.24 (s, 6H).

Example 34

The synthesis of tert-butyl 4-(6-((4-(2-(dimethylamino)benzothiazole-6-yl)-5-fluoropyrimidine-2-yl)amino)nicotinoyl)piperazine-1-carboxylate (I-34):

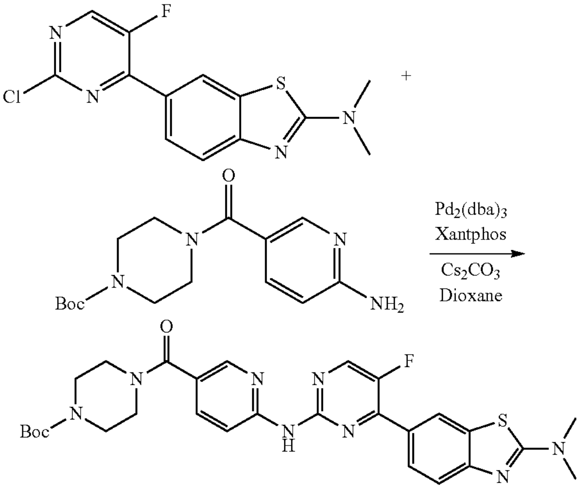

Referring to the synthesis of Compound (1-1), the yield was 50%. $^1H$ NMR (400 MHz, $CDCl_3$) δ 8.91 (s, 1H), 8.53 (dd, J=8.6, 0.8 Hz, 1H), 8.50 (dd, J=2.4, 0.8 Hz, 1H), 8.45 (d, J=3.8 Hz, 1H), 8.44 (d, J=1.8 Hz, 1H), 8.16-8.13 (m, 1H), 7.84 (dd, J=8.7, 2.4 Hz, 1H), 7.66 (d, J=8.6 Hz, 1H), 3.70-3.59 (m, 4H), 3.51-3.46 (m, 4H), 3.27 (s, 6H), 1.48 (s, 9H).

Example 35

The synthesis of (6-((4-(2-(dimethylamino)benzothiazole-6-yl)-5-fluoropyrimidine-2-yl)amino)pyridine-3-yl)(piperazine-1-yl)ketone hydrochloride (I-35):

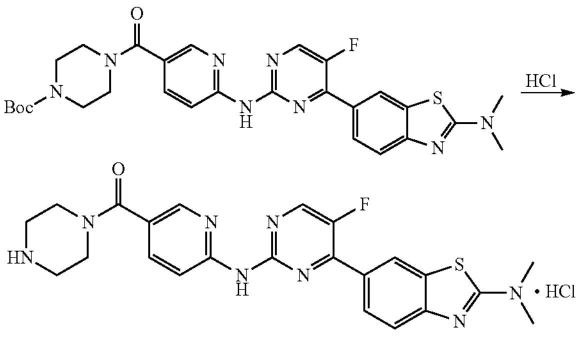

Referring to the synthesis of Compound (I-1), the yield was 100%. H NMR (300 MHz, $CDCl_3$) δ 11.70 (s, 1H), 9.84 (s, 1H), 9.71 (s, 1H), 8.83 (s, 1H), 8.58 (d, J=17.9 Hz, 2H), 8.21 (d, J=8.9 Hz, 1H), 8.14-8.05 (m, 2H), 7.70 (d, J=8.6 Hz, 1H), 3.35-3.32 (m, 4H), 3.28 (s, 6H), 3.20-3.15 (m, 4H).

Example 36

The synthesis of 6-(5-fluoro-2-((5-((4-isopropylpiperazine-1-yl)methyl)pyridine-2-yl)amino)pyrimidine-4-yl)-N,N-dimethylbenzothiazole-2-amine (1-36):

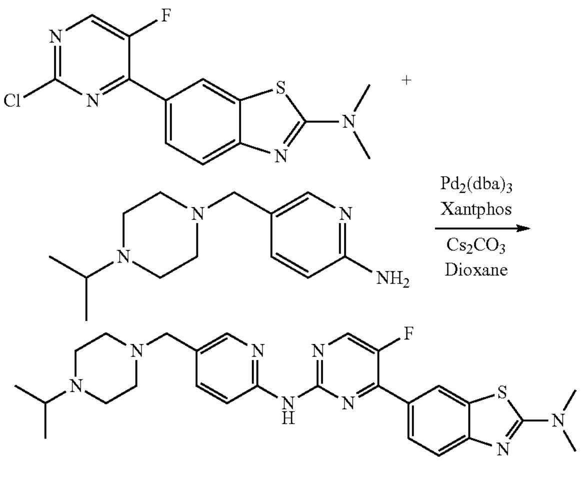

Referring to the synthesis of Compound (I-1), the yield was 52%. $^1$H NMR (400 MHz, $CDCl_3$) δ 8.45 (d, J=1.8 Hz, 1H), 8.38 (dd, J=6.3, 2.4 Hz, 2H), 8.23 (d, J=2.3 Hz, 1H), 8.16-8.14 (m, 2H), 7.71 (dd, J=8.6, 2.3 Hz, 1H), 7.65 (d, J=8.6 Hz, 1H), 3.49 (s, 2H), 3.27 (s, 6H), 2.68-2.54 (m, 9H), 1.05 (d, J=6.5 Hz, 6H).

Example 37

The synthesis of 6-(5-fluoro-2-((5-((4-(methanesulfonyl)piperazine-1-yl)methyl)pyridine-2-yl)amino)pyrimidine-4-yl)-N,N-dimethylbenzothiazole-2-amine (1-37):

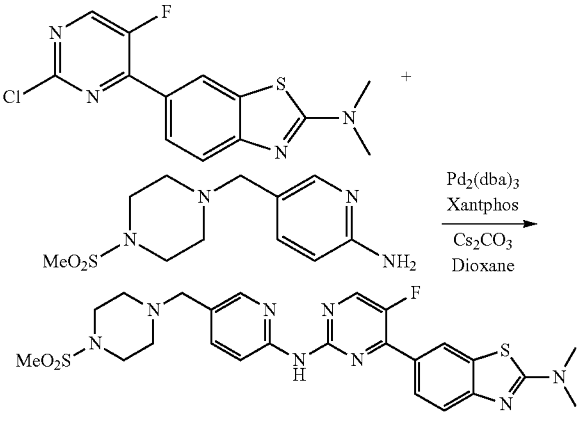

Referring to the synthesis of Compound (I-1), the yield was 43%. $^1$H NMR (400 MHz, $CDCl_3$) δ 8.44-8.35 (m, 3H), 8.21 (d, J=7.7 Hz, 1H), 8.16-8.07 (m, 2H), 7.71 (s, 1H), 7.66-7.61 (m, 1H), 3.55 (s, 2H), 3.29-3.25 (m, 10H), 2.79 (s, 3H), 2.63-2.57 (m, 4H).

Example 38

The synthesis of ethyl 4-((6-((4-(2-(dimethylamino)benzothiazole-6-yl)-5-fluoropyrimidine-2-yl)amino)pyridine-3-yl)methyl)piperazine-1-carboxylate (I-38):

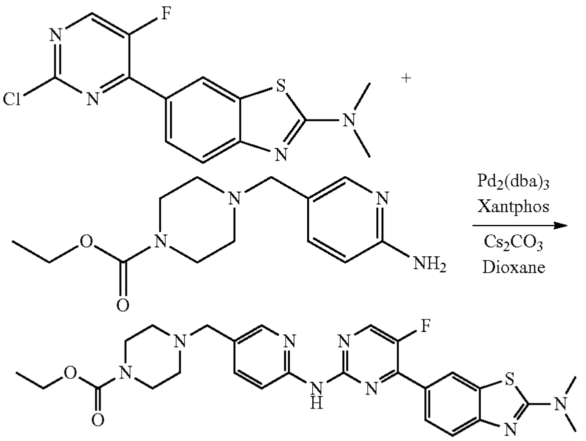

Referring to the synthesis of Compound (I-1), the yield was 53%. $^1$H NMR (400 MHz, $CDCl_3$) δ 8.44-8.36 (m, 3H), 8.31-8.23 (m, 2H), 8.15 (d, J=8.3 Hz, 1H), 7.73 (s, 1H), 7.65 (d, J=8.3 Hz, 1H), 4.13 (q, J=7.1 Hz, 2H), 3.52-3.49 (m, 6H), 3.27 (s, 6H), 2.46-2.41 (m, 4H), 1.26 (t, J=7.3 Hz, 3H).

Example 39

The synthesis of (6-((4-(2-(dimethylamino)benzothiazole-6-yl)-5-fluoropyrimidine-2-yl)amino)pyridine-3-yl)(4-isopropylpiperazine-1-yl)ketone (I-39):

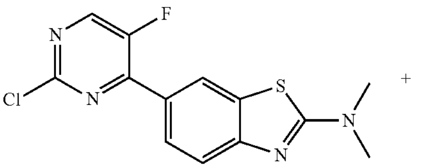

-continued

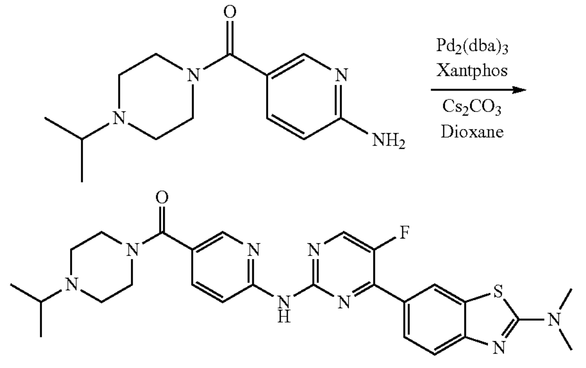

Referring to the synthesis of Compound (I-1), the yield was 44%. $^{1}$H NMR (400 MHz, $CDCl_3$) δ 8.73 (s, 1H), 8.52-8.48 (m, 2H), 8.45-8.44 (m, 2H), 8.16-8.13 (m, 1H), 7.85 (dd, J=8.7, 2.4 Hz, 11H), 7.65 (d, J=8.6 Hz, 11H), 3.75-3.63 (m, 4H), 3.27 (s, 6H), 2.79-2.75 (m, 1H), 2.62-2.55 (m, 4H), 1.08 (d, J=6.5 Hz, 6H).

Example 40

The synthesis of tert-butyl 4-(6-((4-(2-(dimethylamino) benzothiazole-6-yl)-5-fluoropyrimidine-2-yl) amino)pyridine-3-yl)piperazine-1-carboxylate (I-40):

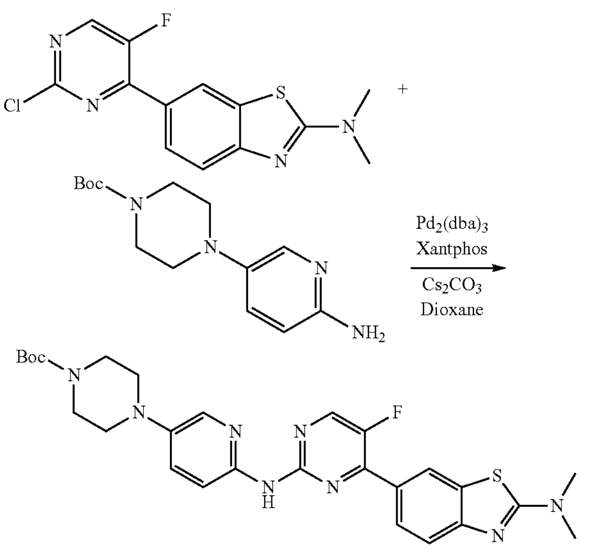

Referring to the synthesis of Compound (I-1), the yield was 40%. H NMR (400 MHz, $CDCl_3$) δ 8.44 (s, 1H), 8.36-8.33 (m, 2H), 8.25 (s, 1H), 8.14 (dd, J=8.7, 1.6 Hz, 1H), 8.00 (d, J=2.8 Hz, 1H), 7.64 (dd, J=8.6, 1.2 Hz, 1H), 7.40 (dd, J=9.3, 2.9 Hz, 1H), 3.61 (t, J=5.0 Hz, 4H), 3.27 (s, 3H), 3.09 (t, J=5.0 Hz, 4H).

Example 41

The synthesis of 6-(5-fluoro-2-((5-(piperazine-1-yl)pyridine-2-yl)amino)pyrimidine-4-yl)-N,N-dimethylbenzothiazole-2-amine hydrochloride (1-41):

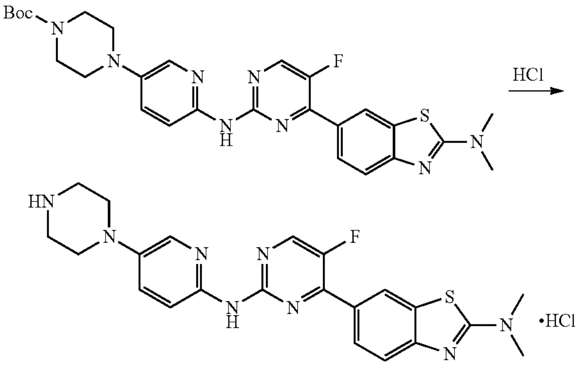

Referring to the synthesis of Compound (I-4), the yield was 100%. H NMR (400 MHz, DMSO-$d_6$) δ 11.99 (s, 1H), 9.77 (s, 2H), 8.81 (d, J=3.5 Hz, 1H), 8.57 (d, J=1.8 Hz, 1H), 8.28 (dd, J=9.7, 2.8 Hz, 1H), 8.12-8.05 (m, 1H), 8.02 (d, J=2.9 Hz, 1H), 7.82 (d, J=9.6 Hz, 1H), 7.69 (d, J=8.6 Hz, 1H), 3.49 (t, J=5.1 Hz, 4H), 3.27 (s, 6H), 3.25-3.23 (m, 4H).

Example 42

The synthesis of (6-((4-(2-(diethylamino)benzothiazole-6-yl)-5-fluoropyrimidine-2-yl)amino)pyridine-3-yl)(4-ethylpiperazine-1-yl)ketone (1-42):

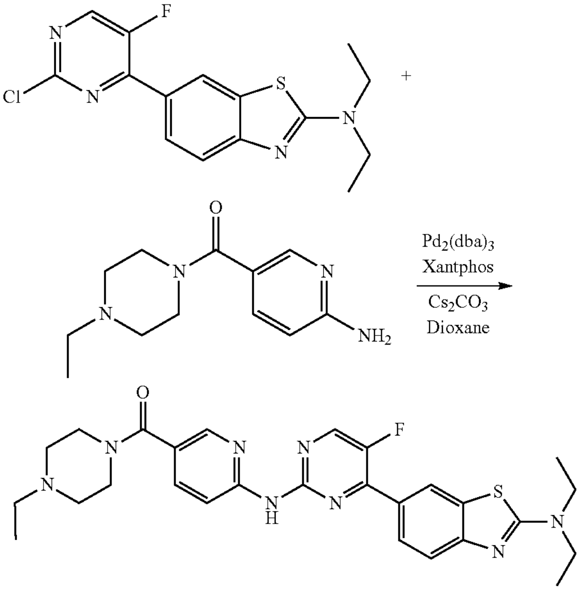

Referring to the synthesis of Compound (I-1), the yield was 44%. $^{1}$H NMR (300 MHz, $CDCl_3$) δ 8.56 (s, 1H), 8.50 (d, J=8.7 Hz, 1H), 8.47 (d, J=2.3 Hz, 1H), 8.43-8.41 (m, 2H), 8.13 (dd, J=8.7, 1.7 Hz, 1H), 7.84 (dd, J=8.7, 2.4 Hz, 1H), 7.62 (d, J=8.6 Hz, 1H), 3.80-3.60 (m, 8H), 2.54-2.47 (m, 6H), 1.33 (t, J=7.1 Hz, 6H), 1.13 (t, J=7.1 Hz, 3H).

Example 43

The synthesis of N,N-diethyl-6-(2-((5-((4-ethylpiperazine-1-yl)methyl)pyridine-2-yl)amino)-5-fluoropyrimidine-4-ylbenzothiazole-2-amine (I-43):

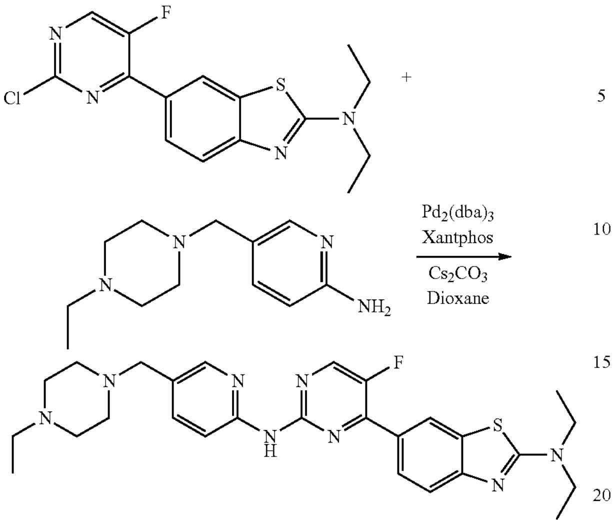

Referring to the synthesis of Compound (I-1), the yield was 38%. $^1$H NMR (400 MHz, $CDCl_3$) δ 8.69 (s, 1H), 8.43-8.39 (m, 3H), 8.29 (d, J=2.3 Hz, 1H), 8.15-8.12 (m, 1H), 7.71 (dd, J=8.6, 2.3 Hz, 1H), 7.62 (d, J=8.6 Hz, 1H), 3.63 (q, J=7.2 Hz, 4H), 3.50 (s, 2H), 2.53-2.42 (m, 10H), 1.33 (t, J=7.1 Hz, 6H), 1.10 (t, J=7.2 Hz, 3H).

Example 44

The synthesis of tert-butyl 4-((6-((4-(2-(diethylamino) benzothiazole-6-yl)-5-fluoropyrimidine-2-yl)amino)pyridine-3-yl)methyl)piperazine-1-carboxylate (I-44):

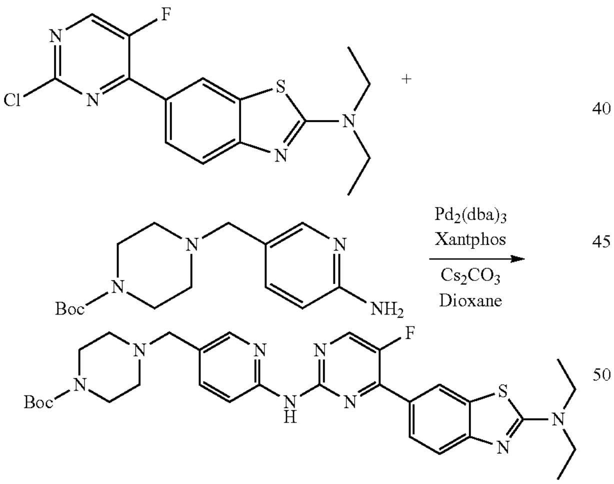

Referring to the synthesis of Compound (I-1), the yield was 48%. $^1$H NMR (400 MHz, $CDCl_3$) δ 8.45 (s, 1H), 8.43-8.39 (m, 3H), 8.26 (d, J=2.2 Hz, 1H), 8.15-8.12 (m, 1H), 7.73 (d, J=8.2 Hz, 1H), 7.62 (d, J=8.6 Hz, 1H), 3.63 (q, J=7.1 Hz, 4H), 3.51 (s, 2H), 3.46-3.44 (m, 4H), 2.44-2.41 (m, 4H), 1.46 (s, 9H), 1.33 (t, J=7.1 Hz, 6H).

Example 45

The synthesis of N,N-diethyl-6-(5-fluoro-2-((5-(piperazine-1-ylmethyl)pyridine-2-yl)amino)pyrimidine-4-yl)benzothiazole-2-amine hydrochloride (I-45):

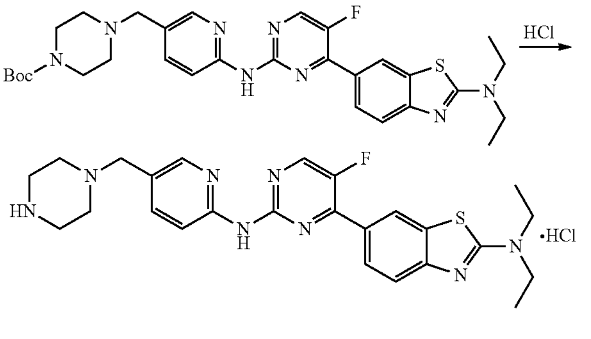

Referring to the synthesis of Compound (I-4), the yield was 100%. $^1$H NMR (400 MHz, DMSO-$d_6$) δ 11.71 (s, 1H), 9.94 (s, 2H), 8.80 (d, J=3.6 Hz, 1H), 8.65 (d, J=2.2 Hz, 1H), 8.56 (d, J=1.8 Hz, 1H), 8.42 (dd, J=8.9, 2.2 Hz, 1H), 8.11-8.08 (m, 1H), 8.01 (d, J=8.9 Hz, 1H), 7.65 (d, J=8.6 Hz, 1H), 4.51 (s, 2H), 3.63 (q, J=7.1 Hz, 4H), 3.50-3.44 (m, 8H), 1.26 (t, J=7.1 Hz, 6H).

Example 46

The synthesis of tert-butyl 4-(6-((4-(2-(diethylamino)benzothiazole-6-yl)-5-fluoropyrimidine-2-yl)amino)nicotinoyl) piperazine-1-carboxylate (1-46):

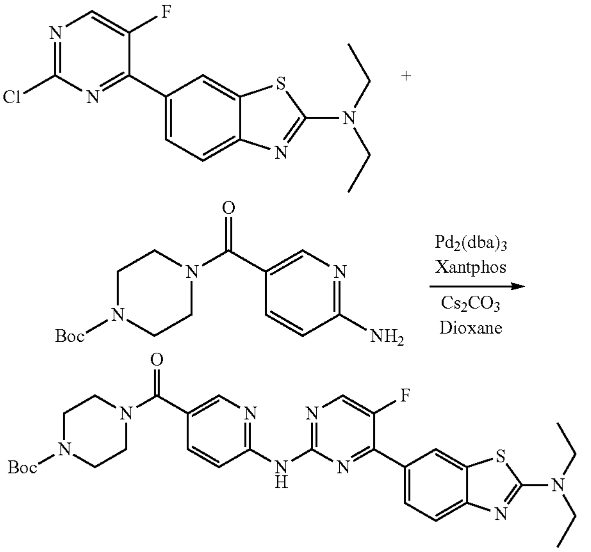

Referring to the synthesis of Compound (I-1), the yield was 40%. $^1$H NMR (400 MHz, $CDCl_3$) δ 8.99 (s, 1H), 8.53 (dd, J=8.7, 0.8 Hz, 1H), 8.51 (dd, J=2.4, 0.9 Hz, 1H), 8.45 (d, J=3.8 Hz, 1H), 8.42 (d, J=1.9 Hz, 1H), 8.15-8.12 (m, 1H), 7.84 (dd, J=8.8, 2.4 Hz, 1H), 7.64 (d, J=8.6 Hz, 11H), 3.67-3.61 (m, 8H), 3.50-3.47 (m, 4H), 1.48 (s, 9H), 1.34 (t, J=7.1 Hz, 6H).

Example 47

The synthesis of (6-((4-(2-(diethylamino)benzothiazole-6-yl)-5-fluoropyrimidine-2-yl)amino)pyridine-3-yl)(piperazine-1-yl)ketone (I-47):

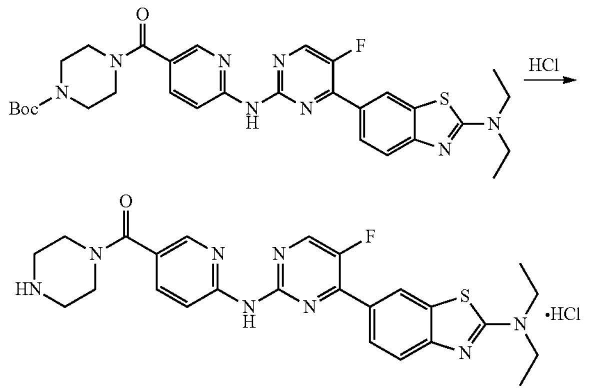

Referring to the synthesis of Compound (I-4), the yield was 100%. $^{1}H$ NMR (400 MHz, DMSO-$d_6$) δ 11.78 (s, 1H), 10.03 (s, 1H), 9.88 (s, 2H), 8.83 (d, J=3.6 Hz, 1H), 8.60 (d, J=1.8 Hz, 1H), 8.58 (d, J=2.1 Hz, 1H), 8.23 (dd, J=8.9, 2.2 Hz, 1H), 8.13-8.07 (m, 2H), 7.71 (d, J=8.6 Hz, 1H), 3.86-3.78 (m, 3H), 3.67 (q, J=7.1 Hz, 4H), 3.19-3.15 (m, 3H), 1.27 (t, J=7.1 Hz, 6H).

Example 48

The synthesis of N,N-diethyl-6-(5-fluoro-2-((5-((4-(methanesulfonyl)piperazine-1-yl)methyl)pyridine-2-yl)amino)pyrimidine-4-yl)benzothiazole-2-amine (I-48):

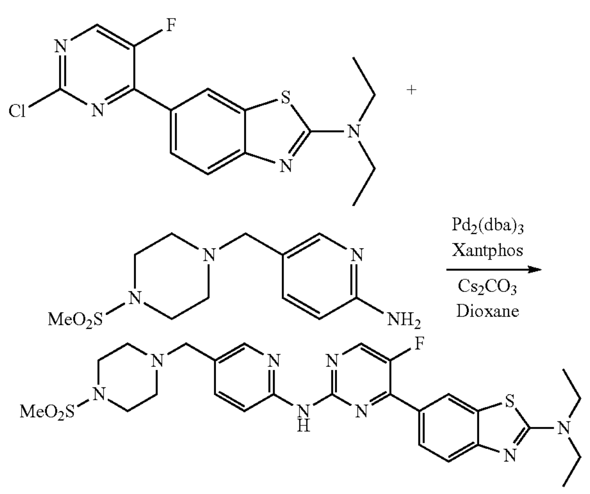

Referring to the synthesis of Compound (I-1), the yield was 44%. $^{1}H$ NMR (300 MHz, $CDCl_3$) δ 8.92 (s, 1H), 8.44-8.42 (m, 3H), 8.32-8.21 (m, 1H), 8.13 (d, J=8.6 Hz, 1H), 7.70 (dd, J=8.6, 2.3 Hz, 1H), 7.62 (d, J=8.7 Hz, 1H), 3.63 (q, J=7.2 Hz, 4H), 3.52 (s, 2H), 3.25 (t, J=4.8 Hz, 3H), 2.78 (s, 3H), 2.58 (t, J=4.7 Hz, 4H), 1.33 (t, J=7.1 Hz, 6H).

Example 49

The synthesis of ethyl 4-((6-((4-(2-(diethylamino)benzothiazole-6-yl)-5-fluoropyrimidine-2-yl)amino)pyridine-3-yl)methyl)piperazine-1-carboxylate (I-49):

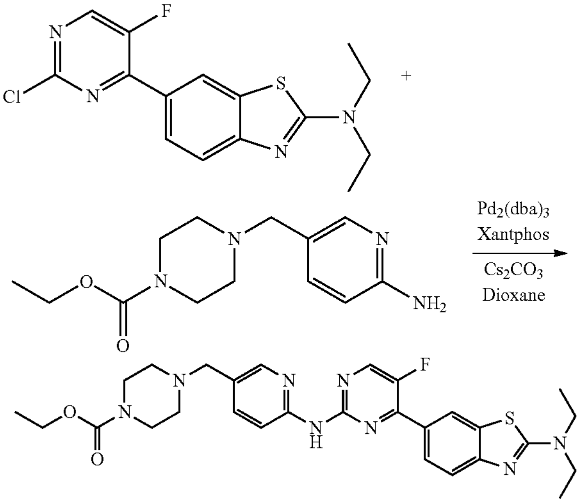

Referring to the synthesis of Compound (I-1), the yield was 50%. $^{1}H$ NMR (300 MHz, $CDCl_3$) δ 8.82 (s, 1H), 8.45-8.42 (m, 3H), 8.30 (d, J=2.2 Hz, 1H), 8.13 (d, J=8.6 Hz, 1H), 7.74 (d, J=8.6 Hz, 1H), 7.62 (d, J=8.6 Hz, 1H), 4.13 (q, J=7.2 Hz, 2H), 3.63 (q, J=7.2 Hz, 4H), 3.53-3.49 (m, 6H), 2.46-2.42 (m, 4H), 1.33 (t, J=7.1 Hz, 6H), 1.26 (t, J=7.1 Hz, 3H).

Example 50

The synthesis of N,N-diethyl-6-5-fluoro-2-((5-((4-isopropylpiperazine-1-yl)methyl)pyridine-2-yl)amino)pyrimidine-4-yl)benzothiazole-2-amine (I-50):

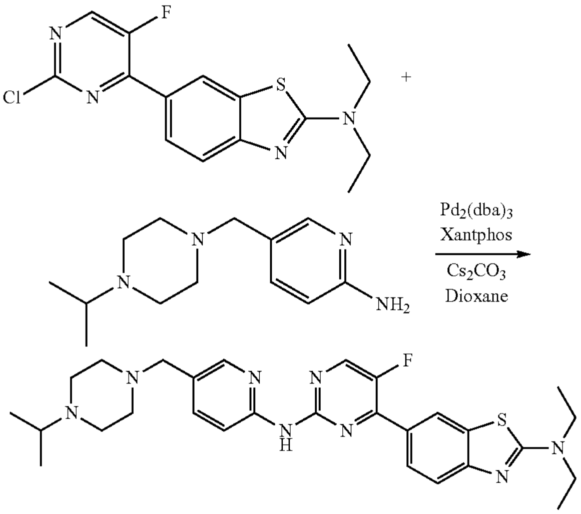

Referring to the synthesis of Compound (I-1), the yield was 48%. $^{1}H$ NMR (300 MHz, $CDCl_3$) δ 9.05 (s, 1H), 8.45-8.40 (m, 3H), 8.32 (d, J=2.3 Hz, 1H), 8.14 (d, J=8.6 Hz, 1H), 7.71 (dd, J=8.7, 2.3 Hz, 1H), 7.61 (d, J=8.7 Hz, 1H), 3.62 (q, J=7.2 Hz, 4H), 3.49 (s, 2H), 2.68-2.55 (m, 9H), 1.32 (t, J=7.1 Hz, 6H), 1.05 (d, J=6.4 Hz, 6H).

Example 51

The synthesis of (6-((4-(2-(diethylamino)benzothiazole-6-yl)-5-fluoropyrimidine-2-yl)amino)pyridine-3-yl)(4-isopropylpiperazine-1-yl)ketone (I-51):

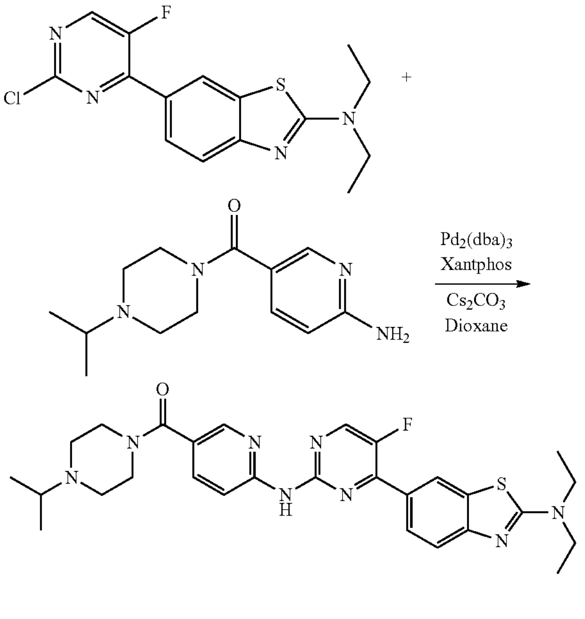

Referring to the synthesis of Compound (I-1), the yield was 47%. $^1$H NMR (300 MHz, $CDCl_3$) δ 9.69 (s, 1H), 8.60 (d, J=2.3 Hz, 1H), 8.54 (d, J=8.7 Hz, 1H), 8.50 (d, J=3.7 Hz, 1H), 8.41 (s, 1H), 8.12 (d, J=8.6 Hz, 1H), 7.86 (dd, J=8.7, 2.3 Hz, 1H), 7.62 (d, J=8.6 Hz, 1H), 3.77-3.59 (m, 8H), 2.78-2.72 (m, 1H), 2.59-2.54 (m, 4H), 1.32 (t, J=7.1 Hz, 6H), 1.07 (d, J=6.4 Hz, 6H).

Example 52

The synthesis of tert-butyl 4-(6-((4-(2-(diethylamino)benzothiazole-6-yl)-5-fluoropyrimidine-2-yl) amino)pyridine-3-yl)piperazine-1-carboxylate (I-52):

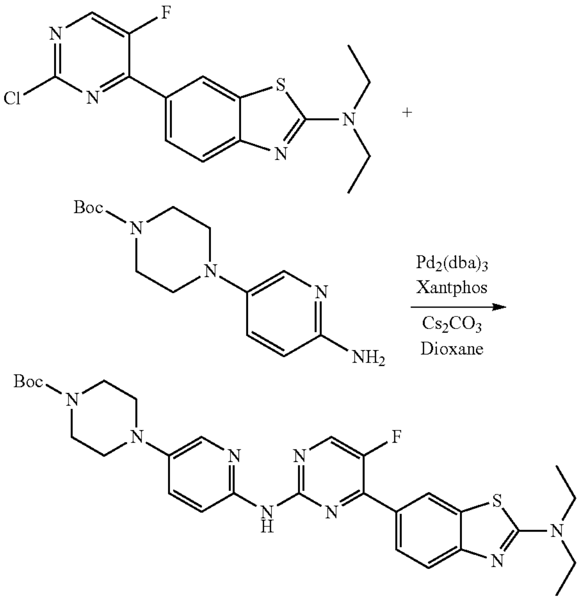

Referring to the synthesis of Compound (I-1), the yield was 49%. $^1$H NMR (300 MHz, $CDCl_3$) δ 8.58 (s, 1H), 8.41 (d, J=1.8 Hz, 1H), 8.37 (d, J=4.0 Hz, 1H), 8.34 (d, J=9.1 Hz, 1H), 8.14-8.10 (m, 1H), 8.06 (d, J=2.9 Hz, 1H), 7.61 (d, J=8.6 Hz, 111), 7.38 (dd, J=9.1, 3.0 Hz, 1H), 3.66-3.58 (m, 8H), 3.09 (t, J=5.1 Hz, 4H), 1.49 (s, 9H), 1.32 (t, J=7.1 Hz, 6H).

Example 53

The synthesis of N,N-diethyl-6-(5-fluoro-2-((5-(piperazine-1-yl)pyridine-2-yl)amino)pyrimidine-4-yl)benzothiazole-2-amine hydrochloride (I-53):

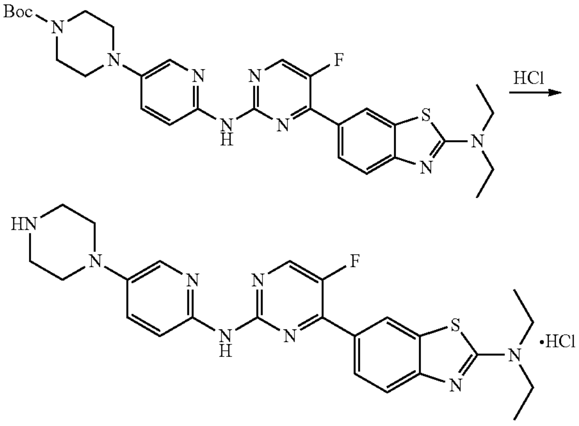

Referring to the synthesis of Compound (I-4), the yield was 100%. H NMR (300 MHz, DMSO-$d_6$) δ 12.15 (s, 1H), 10.04 (s, 2H), 8.79 (s, 1H), 8.57 (s, 1H), 8.34 (d, J=9.3 Hz, 1H), 8.08-8.05 (m, 2H), 7.87 (d, J=8.9 Hz, 1H), 7.71 (d, J=8.4 Hz, 1H), 3.69-3.67 (m, 4H), 3.56-3.53 (m, 4H), 3.27-3.23 (m, 4H), 1.30-1.25 (m, 6H).

The corresponding pharmaceutically acceptable salts in the above examples were reacted by dissolving the main product in dichloromethane and introducing HCl gas at 0° C. for 2 h. After the reaction is completed, the hydrochloride salt is obtain through concentration.

II. Biological Assay

(1) CDK6 Kinase Activity Analysis and Detection Method

In this experiment, the Lance Ultra method from PerkinElmer Co., Ltd. was used for detection. In the test plate, protein kinase, Ulight-labeled polypeptide substrate, ATP, and the compounds were mixed and the reaction was incubated. EDTA was then added to stop the reaction and europium (Eu) chelate-labeled antibody was added for detection. Analysis in this experiment was performed using Envision instrument from PerkinElmer Co., Ltd. in TR-FRET mode. After excitation at a wavelength of 320/340 nm, a fluorescence signal at a wavelength of 665 nm and 615 nm could be emitted. Eu could be transferred to the adjacent fluorescent substance ULight receptor by energy transfer, and then the emitted light was detected.

The measured $IC_{50}$ values are shown in Table 1 below. From the experimental results, it can be seen that the compounds of the examples of the present invention have strong inhibitory activity on CDK6 kinase activity.

TABLE 1

| Measured $IC_{50}$ values on CDK6 kinase activity by the compounds of the invention | |
|---|---|
| Example | IC50 (nM) |
| 1 | 144 |
| 2 | 244 |
| 3 | 272 |
| 4 | 268 |
| 5 | 111 |
| 6 | 104 |
| 7 | >10000 |
| 8 | 129 |
| 9 | >1000 |
| 10 | 169 |
| 11 | 175 |
| 12 | 127 |
| 13 | 210 |
| 14 | >10000 |
| 15 | 464 |
| 16 | 86 |
| 17 | 93 |
| 18 | 90 |
| 19 | 96 |
| 20 | >10000 |
| 21 | 201 |
| 22 | >10000 |
| 23 | 116 |
| 24 | >10000 |
| 25 | >10000 |
| 26 | >1000 |
| 27 | 139 |
| 28 | 132 |
| 29 | 74 |
| 30 | 254 |
| 31 | 18 |
| 32 | >10000 |
| 33 | 59 |
| 34 | >10000 |
| 35 | 41 |
| 36 | 142 |
| 37 | >10000 |
| 38 | >1000 |
| 39 | 57 |
| 40 | >1000 |
| 41 | 61 |
| 42 | 14 |
| 43 | 15 |
| 44 | >1000 |
| 45 | 45 |
| 46 | 443 |
| 47 | 39 |
| 48 | >10000 |
| 49 | >10000 |
| 50 | 31 |
| 51 | 8 |
| 52 | >10000 |
| 53 | 23 |
| / | / |

(2) DYRK2 Kinase Activity Analysis and Detection Method

The DYRK2 kinase inhibitory activity of the compounds of the invention were measured. The method was briefly described as follows (for specific methods, see: Banerjee S, Wei T, Wang J, et al. Inhibition of dual-specificity tyrosine phosphorylation-regulated kinase 2 perturbs 26S proteasome-addicted neoplastic progression[J]. Proceedings of the National Academy of Sciences, 2019, 116(49): 24881-24891):

1) Compounds with different concentrations were added into a 384-well plate, and re-dissolved, followed by the addition of DYRK2 protein, the substrate Woodtide (PubChem CID #166176945) and $^{33}P$-γATP, and the mixture were mixed evenly.

2) The mixture was incubated for 30 minutes at room temperature;

3) 0.5M(3%) orthophosphoric acid solution was added to terminate the reaction, and then the mixture was transferred to P81 plate and washed with 50 mM orthophosphoric acid solution.

4) $IC_{50}$ results were calculated using GraphPad Prism software.

The measured $IC_{50}$ values are shown in Table 2 below. From the experimental results, it can be seen that the compounds of the examples of the present invention have strong inhibitory activity on DYRK2 kinase activity.

TABLE 2

| Measured $IC_{50}$ values on DYRK2 kinase activity by the compounds of the invention | |
|---|---|
| Example | IC50 (nM) |
| 1 | 35 |
| 8 | 85 |
| 11 | 263 |
| 17 | 27 |
| 29 | 106 |
| 31 | 9 |
| 39 | 16 |
| 42 | 14 |
| 43 | 197 |
| 45 | 290 |
| 47 | 39 |
| 51 | 15 |

(3) Determination of Inhibition on the Proliferation of a Variety of Cancer Cells The inhibitory activity of the compounds on the proliferation of 14 cells including human breast cancer (MCF-7), triple negative breast cancer(MDA-MB-231) cell line, multiple myeloma (RPMI8226) cell line, leukemia (K562) cell line, gastric cancer (MGC-803) cell line, ovarian cancer (SK-OV-3) cell line, colon cancer (HT-29) cell line, liver cancer (HepG2) cell line, pancreatic cancer (Panc-1) cell line, human glioma(U251) cell line, lung cancer (A-549), non-small cell lung cancer (NCI-H1299) cell line and prostate cancer (PC-3, Du-145) cell line were determined by the following method.

Experimental Protocol:

The inhibition of the compound on the proliferation of a variety of cancer cells was determined according to the MTT method and the $IC_{50}$ of the half inhibitory concentration of the compound against the cell proliferative activity was obtained.

1) Cells in logarithmic phase were inoculated into 96-well plates at $1\times10^5$ cells/well, and cultured under the condition of 37° C. and 5% $CO_2$ until 90% of the cells were fused. After that, the cells were incubated for 2 h in serum-free DMEM medium, RPMI-1640 medium, L-15 medium, F12K medium, MEM medium, or F-12 medium or IMDM medium to synchronize the cells (the corresponding medium was used for each cell).

2) 100 μL of gradient diluted solution of the test compound with different concentrations was added to the culture plate, and the culture plate was incubated for 72 hours at 37° C. in a 5% $CO_2$ incubator.

3) 4 h before the end of the incubation, 20 μL MTT solution (5 mg/mL) was added to each well. After incubation, the supernatant from each well was discarded, and 150 μL DMSO was added into each well. The solution was oscillated on a cell oscillator for 10 min. After the crystals were fully dissolved, OD570 was measured with a microplate reader. The inhibition rate=(control group OD value−experimental group OD value)/control group OD value×100%.

4) After obtaining the data, the data was fitted with GraphPad Prism 6 to obtain the $IC_{50}$.

The compound of Example 31 (I-31) and the marketed drug CDK4/6 inhibitor Palbociclib were tested for a variety of cancer cell proliferative activities and the measured $IC_{50}$ values are shown in Table 3. It can be seen that Compound I-31 shows inhibitory activity against the proliferation of 14 cells including human breast cancer (MCF-7), triple negative breast cancer (MDA-MB-231) cell line, multiple myeloma (RPM18226) cell line, leukemia (K562) cell line, gastric cancer (MGC-803) cell line, ovarian cancer (SK-OV-3) cell line, colon cancer (HT-29) cell line, liver cancer (HepG2) cell line, pancreatic cancer (Panc-1) cell line, human glioma(U251) cell line, lung cancer (A-549), non-small cell lung cancer (NCI-H1299) cell line and prostate cancer (PC-3, Du-145) cell line, and the inhibitory activities against the proliferation of the 14 cells were significantly stronger than the marketed drug CDK4/6 inhibitor Palbociclib.

TABLE 3

Inhibitory activity $IC_{50}$ of Compound (I) against the proliferation of a variety of cancer cells

| | $IC_{50}$ (μM) | | | | | | |
|---|---|---|---|---|---|---|---|
| Compound | MCF-7 | MDA-MB-231 | RPMI8226 | K-562 | MGC-803 | SK-OV-3 | HT-29 |
| Palbociclib | 4.493 | 4.369 | 2.314 | 2.019 | 4.445 | 4.008 | 3.841 |
| Example 31 | 1.887 | 1.746 | 1.078 | 0.917 | 2.025 | 1.78 | 1.875 |

| | $IC_{50}$ (μM) | | | | | | |
|---|---|---|---|---|---|---|---|
| Compound | HepG2 | NCI-H1299 | A-549 | Panc-1 | U251 | Du-145 | PC-3 |
| Palbociclib | 4.14 | 4.196 | 4.226 | 4.155 | 4.349 | 4.569 | 4.572 |
| Example 31 | 1.545 | 2.131 | 1.641 | 1.926 | 2.149 | 3.302 | 1.069 |

(4) Determination of Acute Toxicity of the Compounds

Test animals: ICR mice; 18-22 g; half male and half female; in total 40.

Dose settings of groups: (1) Control group: Rats were given the same amount of normal saline by gavage, once, for 10 mice, half male and half female in each group; (2) 2500 mg/kg group: The drug was given by gavage to 10 mice, half male and half female, once. (3) 5000 mg/kg group: The drug was given by gavage to 10 mice, half male and half female, once. (4) 10000 mg/kg group: The drug was given by gavage to 10 mice, half male and half female, once.

TABLE 4

Dose settings of groups

| Group | Dose (mg /kg) [Formulation concentration (mg/mL)] | Dosing volume (mL/kg) | Remarks |
|---|---|---|---|
| Control group | — | 40 | Observe the toxicity |
| 2500 mg/kg | 2500 mg/kg 62.5 mg/mL | 40 | Observe the toxicity |
| 5000 mg/kg | 5000 mg/kg 125 mg/mL | 40 | Observe the toxicity |

TABLE 4-continued

Dose settings of groups

| Group | Dose (mg /kg) [Formulation concentration (mg/mL)] | Dosing volume (mL/kg) | Remarks |
|---|---|---|---|
| 10000 mg/kg | 10000 mg/kg 250 mg/mL | 40 | Observe the toxicity |

Laboratory environment: room temperature 24±2° C., relative humidity 60-70%. Observation targets: The test drug (compound prepared in Example 31) was administered once according to the dose shown in Table 4, and the toxicity symptoms and death of the mice were recorded. The dead animals were necropsied. The observation period was 14 days. The results showed that no abnormality was found within 12 h after administration in all groups. No animals died within 24 h of dosing and no animals died after day 14 of dosing. No other obvious abnormalities were observed.

Body weight changes are shown in FIG. 1. No significant toxic effects were observed when 2500 mg/kg, 5000 mg/kg, or 10000 mg/kg were administered intragastrically as compared to the control group.

Figure 2:
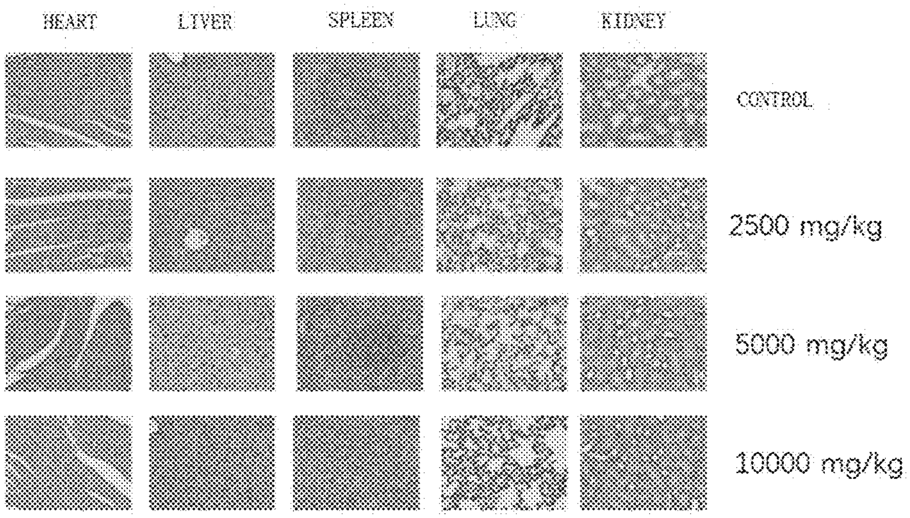
FIG. 2 is a graph showing the results of HE staining in the acute toxicity assay of the invention.

As shown in FIG. 2 by HE staining results, Compound (I-31) prepared in Example 31 showed no significant toxicity to heart, liver, spleen, lung, kidney and other major organs.

(5) Determination of Compound Pharmacokinetics

The tested compound was weighed and placed into a sterile vial, and 250 μL DMSO was added, followed by 10 μL methanesulfonic acid. After dissolution, 4.78 mL of 5% glucose injection was added, and mixed uniformly with ultrasound and shaking to prepare a tested compound solution of 2 mg/mL, which was used as a gavage drug preparation. In addition, 0.5 mL of 2 mg/mL test solution was added with 4.5 mL of 5% glucose injection, and mixed with shaking to prepare 0.2 mg/mL test solution, which was used as an intravenous administration preparation.

Six SD rats were divided into two groups. One was administered via tail vein (1 mg/kg) and the other was administered by gavage (10 mg/kg) with Example 31. blood samples of about 0.25 mL were collected from the posterior orbital venous plexus, in the intravenous injection group 2 min, 5 min, 15 min, 30 min, 1 h, 2 h, 4 h, 6 h, 8 h and 12 h after administration, and in the gavage group 5 min, 15 min, 30 min, 1 h, 2 h, 4 h, 6 h, 8 h, 12 h, and 24 h after administration. The concentrations of Example 31 in plasma samples from SD rats were determined by LC-MS/MS and pharmacokinetic parameters were calculated using WinNolin software, and the results are presented in Table 5.

The results show that the Compound (1-31) of Example 31 of the invention has good metabolism in rats, good absorption and exposure and high bioavailability.

TABLE 5

| Pharmacokinetic Parameter Record | | | | | | | |
|---|---|---|---|---|---|---|---|
| Example | Administration Route | t1/2 (h) | Tmax (h) | Cmax (ng/mL) | AUC0-∞ (hr * ng/mL) | Cl (mL/hr/kg) | F (%) |
| 31 | iv | 2.99 | 0.033 | 974.0 | 1503 | 668.8 | 55.78 |
| | po | 5.08 | 4.00 | 674.3 | 8384 | 1198 | |

(6) Determination of the Anti-Lung Cancer Activity of the Compound

The drugs were Compound (1-31) prepared in Example 31 with the marketed drug CDK4/6 inhibitor Palbociclib. The cell line, human non-small cell lung cancer cell line A-549, was cultured in RPMI-1640 medium containing 10% fetal bovine serum. The test animals were SPF grade BALB/c nude mice; males; five for each group. Drug dose settings are shown in Table 6.

TABLE 6

| Drug dose settings | | | | | |
|---|---|---|---|---|---|
| Group | Test drug | dosage (mg/kg) | Dosing volume (mL/20 g body weight) | Administration route | Observation period (days) |
| Model group | Physiological saline | — | 0.2 | intragastric administration | 21 |
| Example 31 low dose group | Example 31 | 150 | 0.2 | intragastric administration | 21 |
| Example 31 high dose group | Example 31 | 300 | 0.2 | intragastric administration | 21 |
| Positive control drug group | Palbociclib | 150 | 0.2 | intragastric administration | 21 |

Drug Formulation Method:

Example 31 (150 mg/kg): 30 mg of the compound powder to be tested was weighed, dissolved in 2 mL of normal saline, formulated as a 15 mg/mL drug, and administered orally by gavage in a volume of 0.2 mL/20 g.

Example 31 (300 mg/kg): 60 mg of the compound powder to be tested was weighed, dissolved in 2 ml of normal saline, formulated as a 30 mg/mL drug, and administered orally by gavage in a volume of 0.2 mL/20 g.

Palbociclib (150 mg/kg): 30 mg of the compound powder to be tested was weighed, dissolved in 2 mL of normal saline, and prepared into a 15 mg/mL drug for oral gavage administration in a volume of 0.2 mL/20 g.

Experimental method: A nude mouse model of human lung cancer xenografts was established by inoculating human lung cancer cell line A549 under the axillary skin of nude mice. A549 cells in logarithmic phase were inoculated subcutaneously at right axilla of 30 nude mice under sterile condition, and the inoculation amount of cells was $5\times10^6$ cells/mouse. The diameter of xenografts was measured with a vernier caliper. When the tumor grew to about 80 $mm^3$, 20 tumor-bearing nude mice in good growth condition and with uniform tumor size were selected and randomly divided into four groups, five for each group, i.e., the model group, the low-dose group of Example 31 (150 mg/kg), the high-dose group of Example 31 (300 mg/kg), and the positive drug Palbociclib (150 mg/kg) group. Test Drug Example 31 and Palbociclib were intragastrically administered to the low-dose and high-dose groups and the positive drug group, once every 2 days. The model group was intragastrically administered with an equal volume of vehicle control. The antitumor effect of the test substance was dynamically observed by measuring the tumor diameter. Tumor diameters were measured every other day and nude mice were weighed while tumor diameters were measured. The mice were sacrificed on the 22nd day, and the tumor pieces removed by surgery were fixed with 10% formaldehyde and stored in liquid nitrogen for later use.

The experimental results showed that compared with the model group, the relative tumor proliferation rates T/C (%) of the low-dose group of Example 31 (150 mg/kg) and the high-dose group of Example 31 (300 mg/kg) were 44.8% and 35.9%, respectively, and the tumor growth inhibition rates were 55.2% and 64.1%, respectively. When the positive drug Palbociclib was given by gavage at the dose of 150 mg/kg, the relative tumor proliferation rate T/C (%) and tumor inhibition rate were 39.6% and 60.4%, respectively.

Therefore, the test drug prepared in Example 31 had a significant inhibitory effect on the growth of xenografts of human lung cancer A549 in nude mice, and the effect was better than that of the positive control drug Palbociclib.

(7) Determination of the Prostate Cancer (PC3) Activity of the Compound

The drugs were Compound (I-31) prepared in example 31 with the marketed drug CDK4/6 inhibitor Palbociclib. The cell strain was a human prostate cancer PC-3 cell. The test animals were SPF grade BALB/c nude mice; Males; Eight for each group. Drug dose settings are shown in Table 7.

TABLE 7

Drug dose settings

| Group | Test drug | dosage (mg/kg) | Dosing volume (mL/20 g body weight) | Administration route | Observation period (days) |
|---|---|---|---|---|---|
| Model group | Physiological saline | — | 0.2 | intragastric administration | 28 |
| Example 31 low dose group | Example 31 | 100 | 0.2 | intragastric administration | 28 |
| Example 31 high dose group | Example 31 | 200 | 0.2 | intragastric administration | 28 |
| Positive control drug group | Palbociclib | 100 | 0.2 | intragastric administration | 28 |

EXAMPLE

Drug Formulation Method:

Example 31 (100 mg/kg): 20 mg of the compound powder to be tested was weighed, dissolved in 2 mL of normal saline, formulated as a 10 mg/mL drug, and administered orally by gavage in a volume of 0.2 mL/20 g.

Example 31 (200 mg/kg): 40 mg of the compound powder to be tested was weighed, dissolved in 2 ml of normal saline, formulated as a 20 mg/mL drug, and administered orally by gavage in a volume of 0.2 mL/20 g.

Palbociclib (100 mg/kg): 20 mg of the compound powder to be tested was weighed, dissolved in 2 mL of normal saline, and prepared into a 10 mg/mL drug for oral gavage administration in a volume of 0.2 mL/20 g.

Experimental method: A nude mouse model of human prostate cancer xenografts was established by inoculating human prostate cancer PC-3 under the axillary skin of nude mice. PC-3 cells in logarithmic phase were inoculated subcutaneously at right axilla of 40 nude mice under sterile condition, and the inoculation amount of cells was $5\times10^6$ cells/mouse. The diameter of xenografts was measured with a vernier caliper. When the tumor grew to about 90 $mm^3$, 32 tumor-bearing nude mice in good growth condition and with uniform tumor size were selected and randomly divided into four groups, eight for each group, i.e., the model group, the low-dose group of Example 31 (100 mg/kg), the high-dose group of Example 31 (200 mg/kg), and the positive drug Palbociclib (100 mg/kg) group. Test Drug Example 31 and Palbociclib were intragastrically administered to the low-dose and high-dose groups and the positive drug group, once every day. The model group was intragastrically administered with an equal volume of vehicle control. The antitumor effect of the test substance was dynamically observed by measuring the tumor diameter. Tumor diameters were measured every other day and nude mice were weighed while tumor diameters were measured. The mice were sacrificed on the 29th day, and the tumor pieces removed by surgery were fixed with 10% formaldehyde and stored in liquid nitrogen for later use.

The experimental results showed that compared with the model group, the relative tumor proliferation rates T/C (%) of the low-dose group of Example 31 (100 mg/kg) and the high-dose group of Example 31 (200 mg/kg) were 35.7% and 23.4%, respectively, and the tumor growth inhibition rates were 64.3% and 76.6%, respectively. When the positive drug Palbociclib was given by gavage at the dose of 100 mg/kg, the relative tumor proliferation rate T/C (%) and tumor inhibition rate were 35.5% and 64.5%, respectively.

Therefore, the test drug prepared in Example 31 had a significant inhibitory effect on the growth of xenografts of human prostate cancer PC3 in nude mice, and the effect was better than that of the positive control drug Palbociclib.

(8) Determination of the Prostate Cancer (Du-145) Activity of the Compound

The drugs were the compound (I-31) prepared in example 31, the marketed drug CDK4/6 inhibitor Palbociclib and the first-line treatment drug for prostate cancer Enzalutamide. The cell strain is human prostate cancer Du-145 cells. The test animals were SPF grade BALB/c nude mice; males; ten for each group. Drug dose settings are shown in Table 8.

TABLE 8

| Drug dose settings | | | | | |
|---|---|---|---|---|---|
| Group | Test drug | dosage (mg/kg) | Dosing volume (mL/20 g body weight) | Administration route | Observation period (days) |
| Model group | Physiological saline | — | 0.2 | intragastric administration | 49 |
| Example 31 low dose group | Example 31 | 100 | 0.2 | intragastric administration | 49 |
| Example 31 high dose group | Example 31 | 200 | 0.2 | intragastric administration | 49 |
| Positive control drug group1 | Palbociclib | 100 | 0.2 | intragastric administration | 49 |
| Positive control drug group2 | Enzalutamide | 100 | 0.2 | intragastric administration | 49 |

Drug Formulation Method:

Example 31 (100 mg/kg): 20 mg of the compound powder to be tested was weighed, dissolved in 2 mL of normal saline, formulated as a 10 mg/mL drug, and administered orally by gavage in a volume of 0.2 mL/20 g.

Example 31 (200 mg/kg): 40 mg of the compound powder to be tested was weighed, dissolved in 2 ml of normal saline, formulated as a 20 mg/mL drug, and administered orally by gavage in a volume of 0.2 mL/20 g.

Enzalutamide (100 mg/kg): 20 mg of the compound powder to be tested was weighed, dissolved in 2 mL of normal saline, and prepared into a 10 mg/mL drug for oral gavage administration in a volume of 0.2 mL/20 g.

Experimental method: A nude mouse model of human prostate cancer xenografts was established by inoculating human prostate cancer Du-145 under the axillary skin of nude mice. Du-145 cells in logarithmic phase were inoculated subcutaneously at right axilla of 60 nude mice under sterile condition, and the inoculation amount of cells was $5\times10^6$ cells/mouse. The diameter of xenografts was measured with a vernier caliper. When the tumor grew to about 90 $mm^3$, 50 tumor-bearing nude mice in good growth condition and with uniform tumor size were selected and randomly divided into five groups, ten for each group, i.e., the model group, the low-dose group of Example 31 (100 mg/kg), the high-dose group of Example 31 (200 mg/kg), the positive drug Palbociclib (100 mg/kg) group, and the positive drug Enzalutamide (100 mg/kg) group. Test Drug Example 31, Palbociclib and Enzalutamide were intragastrically administered to the low-dose and high-dose groups and the positive drug group, once every day. The model group was intragastrically administered with an equal volume of vehicle control. The antitumor effect of the test substance was dynamically observed by measuring the tumor diameter. Tumor diameters were measured every other day and nude mice were weighed while tumor diameters were measured. On the 35th day, the mice of the control group were sacrificed, and the tumor pieces after surgical stripping were fixed with 10% formaldehyde and stored in liquid nitrogen for later use. The remaining mice were sacrificed on the 49th day, and the tumor pieces after surgical stripping were fixed with 10% formaldehyde and stored in liquid nitrogen for later use.

Figure 3:
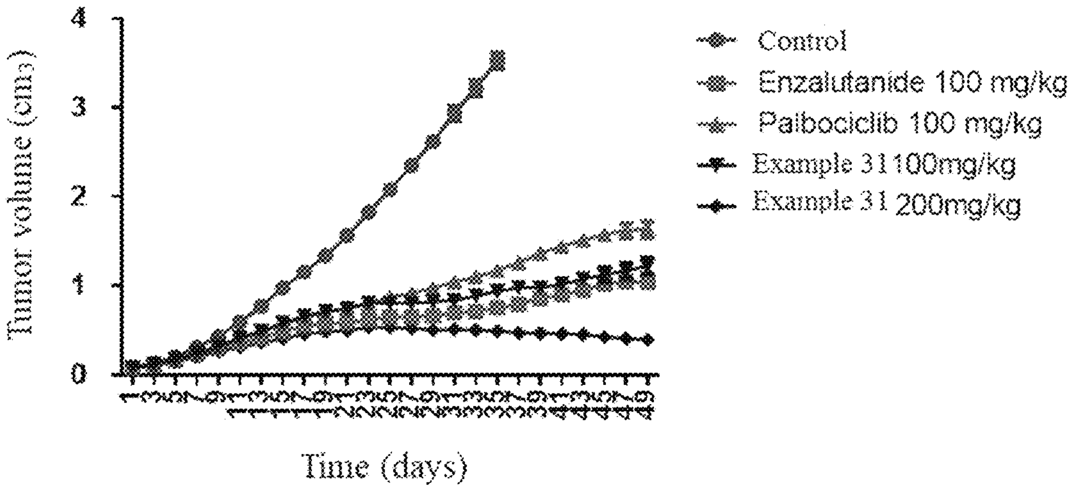
FIG. 3 is a graph of results for prostate cancer tumor volume according to the invention.

The experimental results are shown in FIG. 3: the low dose group of test drug Example 31 (100 mg/kg) exhibited better inhibition on tumor growth than the positive drug Palbociclib (100 mg/kg) group; the low dose group of test drug Example 31 (100 mg/kg) and the positive drug Enzalutamide (100 mg/kg) had similar inhibition effects on tumor growth. Example 31 (200 mg/kg) the high dose group significantly inhibited tumor growth, better than the positive drug Palbociclib(100 mg/kg) group and the positive drug Enzalutamide (100 mg/kg) group, and started to reduce tumor volume on day 31.

Therefore, the test drug prepared in Example 31 has a significant inhibitory effect on the growth of xenografts of nude mice with human prostate cancer Du-145, and the effect is better than that of the positive control drug CDK4/6 inhibitor Palbociclib and the first-line treatment drug of prostate cancer Enzalutamide.

What is claimed:

1. A compound selected from the group consisting of:

I-1

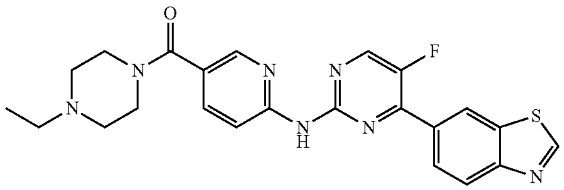

I-8

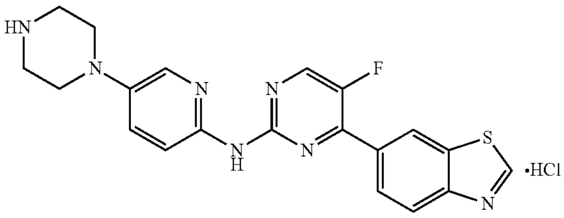

-continued
I-11
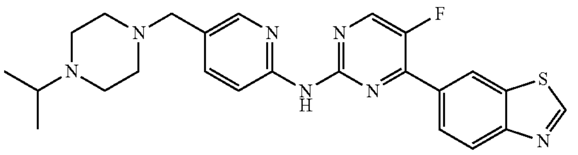
I-17
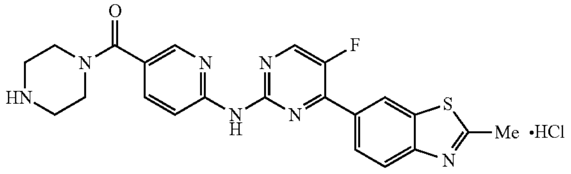
I-29
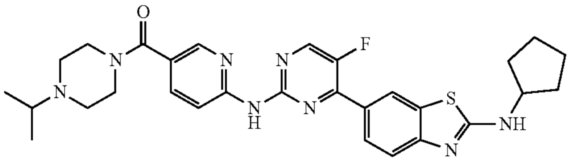
I-31
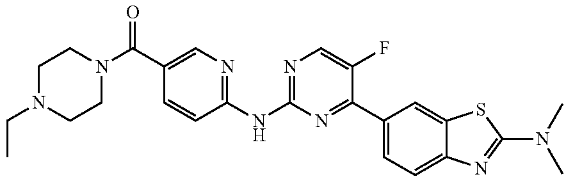
I-39
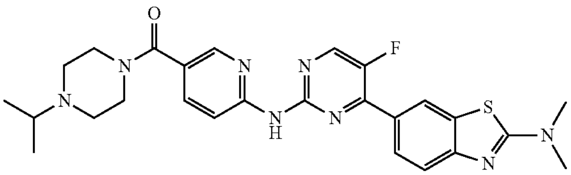
I-42
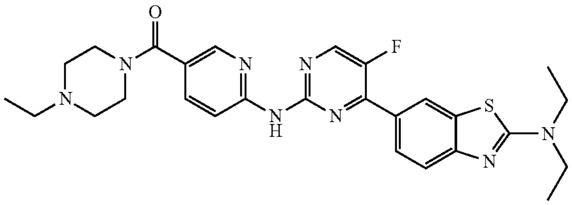
I-43
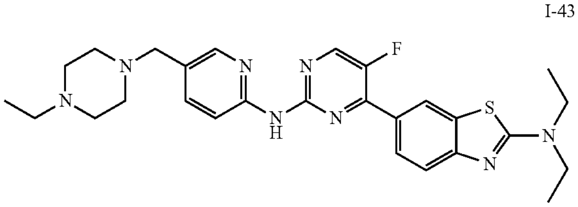
I-45
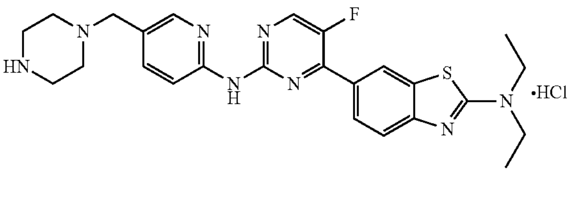
-continued
I-47
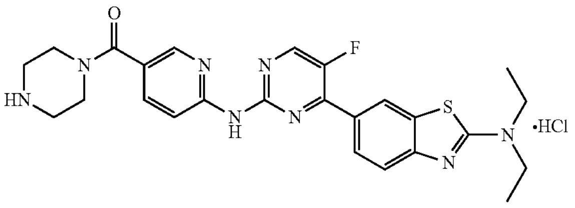
I-51
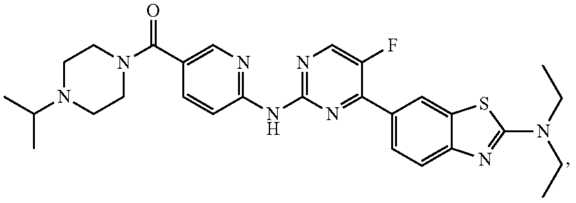
or a pharmaceutically acceptable salt thereof.
2. A dual-target inhibitor of cyclin-dependent kinase 6 (CDK6) and dual-specificity tyrosine phosphorylation-regulated kinase (DYRK2), wherein the dual-target inhibitor is selected from the group consisting of
I-1
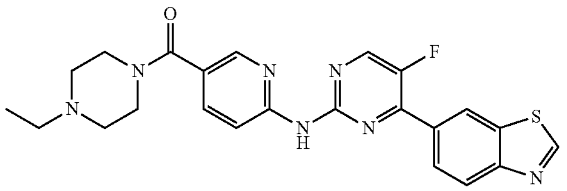
I-8
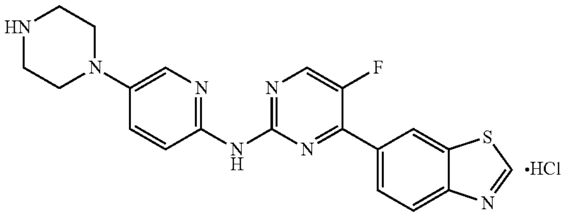
I-11
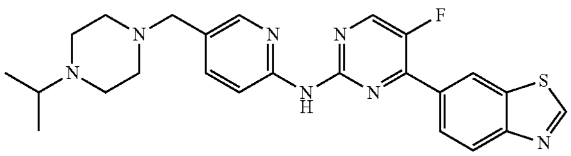
I-17
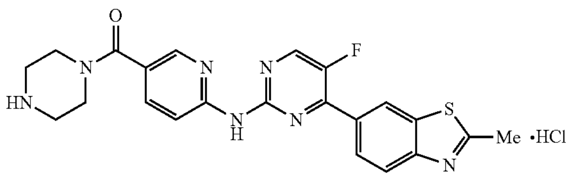

-continued

I-29

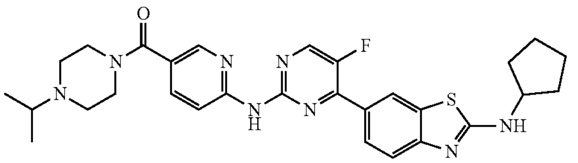

I-31

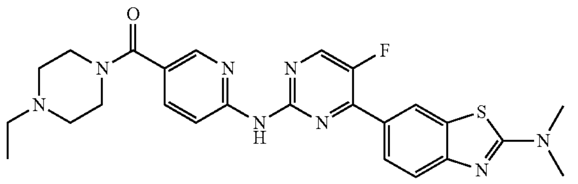

I-39

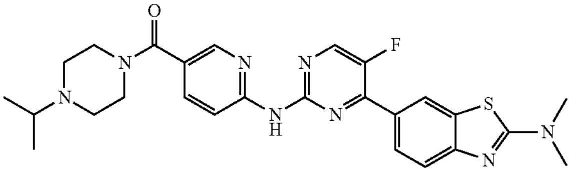

I-42

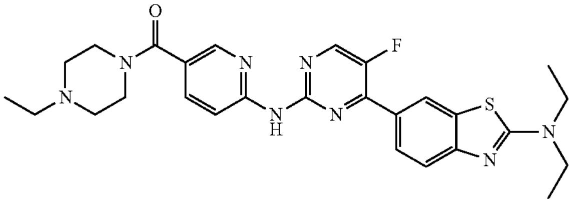

I-43

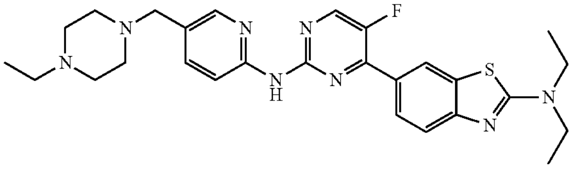

I-45

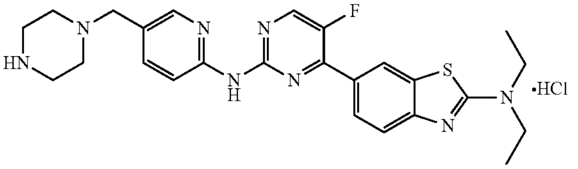

I-47

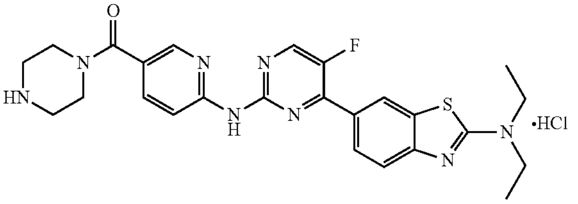

-continued

I-51

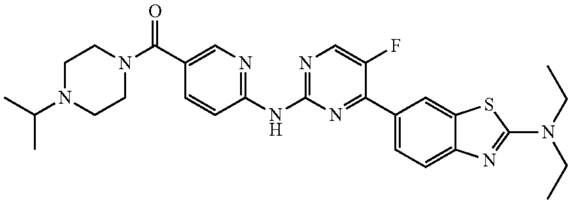

or a pharmaceutically acceptable salt thereof, which simultaneously inhibits CDK6 and DYRK2.

3. The compound or a pharmaceutically acceptable salt thereof according to claim 1, wherein: said pharmaceutically acceptable salt is an acidic addition salt of the said compound, wherein the salt forming acid is selected from an inorganic acid and an organic acid, said inorganic acid is selected from hydrochloric acid, sulfuric acid, phosphoric acid and methanesulfonic acid, said organic acid is selected from acetic acid, trichloroacetic acid, propionic acid, butyric acid, maleic acid, p-toluenesulfonic acid, malic acid, malonic acid, cinnamic acid, citric acid, fumaric acid, camphoric acid, digluconic acid, aspartic acid and tartaric acid.

4. A pharmaceutical composition comprising a compound of claim 1, or a pharmaceutically acceptable salt thereof, and a pharmaceutically acceptable carrier.

5. A method of treating and/or preventing cyclin-dependent kinase 6 (CDK6) and dual-specificity tyrosine phosphorylation-regulated kinase (DYRK2)-related cancer and/or tumor, wherein the CDK6 and DYRK2-related cancer or tumor is one or more of breast cancer, prostate cancer, lung cancer, multiple myeloma, leukemia, gastric cancer, ovarian cancer, colon cancer, liver cancer, pancreatic cancer and human glioma, the method comprising administration of one of the compounds of claim 1 or a pharmaceutically acceptable salt thereof, capable of simultaneously inhibiting CDK6 and DYRK2.

6. A method of reducing drug resistance arising in CDK6 single-target inhibitors that selectively target CDK6, comprising administering the dual-target inhibitor of claim 2.

7. A method of inhibiting the cell proliferation of human breast cancer cells, multiple myeloma cells, leukemia cells, gastric cancer cells, ovarian cancer cells, colon cancer cells, liver cancer cells, pancreatic cancer cells, human glioma cells, lung cancer cells, or prostate cancer cells, comprising administering the dual-target inhibitor of claim 2.

* * * * *